US006943153B1

(12) United States Patent
Manning, Jr. et al.

(10) Patent No.: US 6,943,153 B1
(45) Date of Patent: Sep. 13, 2005

(54) USE OF RECOMBINANT GENE DELIVERY VECTORS FOR TREATING OR PREVENTING DISEASES OF THE EYE

(75) Inventors: William C. Manning, Jr., Redwood City, CA (US); Varavani J. Dwarki, Pittstown, NJ (US); Katherine Rendahl, Berkeley, CA (US); Shangzhen Zhou, Alameda, CA (US); Sheldon S. Miller, Berkeley, CA (US); Fei Wang, Albany, CA (US)

(73) Assignees: The Regents of the University of California, Oakland, CA (US); Chiron Corporation, Emeryville, CA (US)

( * ) Notice: Subject to any disclaimer, the term of this patent is extended or adjusted under 35 U.S.C. 154(b) by 269 days.

(21) Appl. No.: 09/665,493

(22) Filed: Sep. 20, 2000

Related U.S. Application Data

(63) Continuation-in-part of application No. 09/525,956, filed on Mar. 15, 2000, now abandoned.
(60) Provisional application No. 60/124,460, filed on Mar. 15, 1999, and provisional application No. 60/174,984, filed on Jan. 6, 2000.

(51) Int. Cl.[7] ......................... A01N 43/04; A01N 63/00; A61K 31/70; A61K 48/00; A61K 39/23; A61K 39/235
(52) U.S. Cl. ..................... 514/44; 424/93.21; 424/233.1
(58) Field of Search .................... 514/44; 424/93.21, 424/233.1, 9.1, 9.2; 435/325

(56) References Cited

U.S. PATENT DOCUMENTS

| 5,641,749 A | 6/1997 | Yan et al. ....................... 514/12 |
| 5,792,845 A | 8/1998 | O'Reilly et al. ............ 536/23.1 |
| 5,814,618 A | * 9/1998 | Bujard et al. .................. 514/44 |

FOREIGN PATENT DOCUMENTS

| EP | 407 122 A1 | 1/1991 |
| JP | 11100327 | 4/1999 |
| WO | WO 95/26409 | 10/1995 |
| WO | WO 98/13071 | 4/1998 |
| WO | WO 98/51323 | 11/1998 |
| WO | WO 99/16889 | 4/1999 |
| WO | WO 99/36511 A2 | 7/1999 |
| WO | WO 99/45952 | 9/1999 |
| WO | WO 99/66959 A2 | 12/1999 |
| WO | WO 00/01815 | 1/2000 |
| WO | WO 00/15822 | 3/2000 |
| WO | WO 00/54813 A2 | 9/2000 |
| WO | WO 00/71582 A1 | 11/2000 |

OTHER PUBLICATIONS

Auricchio, A. et al. Mol. Therapy. 6(4): 490–494, Oct. 2002.*
Romano et al. Stem Cells, 2000, 18:19–39.*
Ali et al. Br J Opthalmol, vol. 81, Sep. 1997, pp. 795–801.*
Kendall et al. PNAS, vol. 90, Nov. 1993, pp. 10705–10709.*
Tolentino, et al., Vascular Endothelial Growth Factor is Sufficient to Produce Iris Neovasularization and Neovascular Glaucoma in a Nonhuman Primate, Arch Opthalmol, vol. 114, pp. 964–970, Aug. 1996.
Oikawa et al., "Three Novel Synthetic Retinoids, Re 80, Am 580 and Am 80, all Exhibit Anti–Angiogenic Activity in vivo" *European Journal of Pharmacology* 249:113–116, 1993.
Luthert and Chong, "Photoreceptor Rescue" *Eye* 12:591–596, 1998.
Fotsis et al., "The Endogenous Oestrogen Metabolite 2–Methoxyoestradiol Inhibits Angiogenesis and Suppresses Tumour Growth" *Nature* 368:237–239, Mar. 17, 1994.
Akimoto et al., "Adenovirally Expressed Basic Fibroblast Growth Factor Rescues Photoreceptor Cells in RCS Rats" *Investigative Ophthalmology and Visual Science* 40(2):273–279, Feb. 1999.
Peterson et al., "Enhanced Survival of Photoreceptors in p23h Mutant Rhodopsin Transgenic Rats by Adeno–Associated Virus (AAV) –Madiated Delivery of Neurotrophic Genes" *IOVS* 39:S1117, Mar. 15, 1998.
Shafiee et al., "Thrombospondin Peptides Inhibit Angiogenesis in Retinal Explant Assay and Rat Model of Retinopathy of Prematurity" *IOVS* 38:S984, 1997.
Smith et al., "Inhibition of Retinal Neovascularization with an IGF–1 Receptor Antagonist" *IOVS* 39(4):S450, Mar. 15, 1998.
Cayouette and Gravel, "Adenovirus–Mediated Gene Transfer of Ciliary Neurotrophic Factor can Prevent Photoreceptor Degeneration in the Retinal Degeneration (rd) Mouse" *Human Gene Therapy* 8:423–430, Mar. 1, 1997.

* cited by examiner

*Primary Examiner*—Joseph Woitach
*Assistant Examiner*—Thaian N. Ton
(74) *Attorney, Agent, or Firm*—Carol L. Francis; Edward J. Baba; Bozicevic, Field & Francis LLP

(57) ABSTRACT

Gene delivery vectors, such as, for example, recombinant adeno-associated viral vectors, and methods of using such vectors are provided for use in treating or preventing diseases of the eye.

3 Claims, 42 Drawing Sheets

```
ACCATGTAGCGGCCCTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGTTCCTTGTAGTTAAT
GATTAACCCGCCATGCTACTTATCTACGTAGCCATGCTCTAGGGAATTGGCCGCGGAATTTCGACTCTAGGCCATTG
CATACGTTGTATCTATATCATAATATGTACATTTATATTGGCTCATGTCCAATATGACCGCCATGTTGACATTGATT
ATTGACTAGTTATTAATAGTAATCAATTACGGGGTCATTAGTTCATAGCCCATATATGGAGTTCCGCGTTACATAAC
TTACGGTAAATGGCCCGCCTGGCTGACCGCCCAACGACCCCCGCCCATTGACGTCAATAATGACGTATGTTCCCATA
GTAACGCCAATAGGGACTTTCCATTGACGTCAATGGGTGGAGTATTTACGGTAAACTGCCCACTTGGCAGTACATCA
AGTGTATCATATGCCAAGTCCGCCCCCTATTGACGTCAATGACGGTAAATGGCCCGCCTGGCATTATGCCCAGTACA
TGACCTTACGGGACTTTCCTACTTGGCAGTACATCTACGTATTAGTCATCGCTATTACCATGGTGATGCGGTTTTGG
CAGTACACCAATGGGCGTGGATAGCGGTTTGACTCACGGGGATTTCCAAGTCTCCACCCCATTGACGTCAATGGGAG
TTTGTTTTGGCACCAAAATCAACGGGACTTTCCAAAATGTCGTAATAACCCCGCCCCGTTGACGCAAATGGGCGGTA
GGCGTGTACGGTGGGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGCCGGGAACGGTGCATTGGAACGCGGATTCC
CCGTGCCAAGAGTGACGTAAGTACCGCCTATAGACTCTATAGGCACACCCCTTTGGCTCTTATGCATGCTATACTGT
TTTTGGCTTGGGGCCTATACACCCCCGCTCCTTATGCTATAGGTGATGGTATAGCTTAGCCTATAGGTGTGGGTTAT
TGACCATTATTGACCACTCCCTATTGGTGACGATACTTTCCATTACTAATCCATAACATGGCTCTTTGCCACAACT
ATCTCTATTGGCTATATGCCAATACTCTGTCCTTCAGAGACTGACACGGACTCTGTATTTTTACAGGATGGGGTCCA
TTTATTATTTACAAATTCACATATACAACAACGCCGTCCCCCGTGCCCGCAGTTTTTATTAAACATAGCGTGGGATC
TCCGACATCTCGGGTACGTGTTCCGGACATGGGCTCTTCTCCGGTAGCGGCGGAGCTTCCACATCCGAGCCCTGGTC
CCATCCGTCCAGCGGCTCATGGTCGCTCGGCAGCTCCTTGCTCCTAACAGTGGAGGCCAGACTTAGGCACAGCACAA
TGCCCACCACCACCAGTGTGCCGCACAAGGCCGTGGCGGTAGGGTATGTGTCTGAAAATGAGCTCGGAGATTGGGCT
CGCACCTGGACGCAGATGGAAGACTTAAGGCAGCGGCAGAAGAAGATGCAGGCAGCTGAGTTGTTGTATTCTGATAA
GAGTCAGAGGTAACTCCCGTTGCGGTGCTGTTAACGGTGGAGGGCAGTGTAGTCTGAGCAGTACTCGTTGCTGCCGC
GCGCGCCACCAGACATAATAGCTGACAGACTAACAGACTGTTCCTTTCCATGGGTCTTTTCTGCAGTCACCGTCGTC
GACCTAAGAATTCAGGCCTAAGCTTCCTAGGTATCGATCTCGAGCAAGTCTAGAGGGAGACCACAACGGTTTCCCTC
TAGCGGGATCAATTCCGCCCCCCCCCTAACGTTACTGGCCGAAGCCGCTTGGAATAAGGCCGGTGTGCGTTTGTCT
ATATGTTATTTTCCACCATATTGCCGTCTTTTGGCAATGTGAGGGCCCGGAAACCTGGCCCTGTCTTCTTGACGAGC
ATTCCTAGGGGTCTTTCCCCTCTCGCCAAAGGAATGCAAGGTCTGTTGAATGTCGTGAAGGAAGCAGTTCCTCTGGA
AGCTTCTTGAAGACAAACAACGTCTGTAGCGACCCTTTGCAGGCAGCGGAACCCCCCACCTGGCGACAGGTGCCTCT
GCGGCCAAAAGCCACGTGTATAAGATACACCTGCAAAGGCGGCACAACCCCAGTGCCACGTTGTGAGTTGGATAGTT
GTGGAAAGAGTCAAATGGCTCTCCTCAAGCGTATTCAACAAGGGGCTGAAGGATGCCCAGAAGGTACCCCATTGTAT
GGGATCTGATCTGGGGCCTCGGTGCACATGCTTTACATGTGTTTAGTCGAGGTTAAAAAAACGTCTAGGCCCCCCGA
ACCACGGGGACGTGGTTTTCCTTTGAAAAACACGATAATACCATGGCCGCCGGGAGCATCACCACGCTGCCAGCCCT
GCCGGAGGACGGCGGCAGCGGCGCTTTCCCGCCGGGCCACTTCAAGGACCCCAAGCGGCTGTACTGCAAGAACGGGG
GCTTCTTCCTGCGCATCCACCCCGACGGCCGAGTGGACGGGGTCCGCGAGAAGAGCGACCCACACATCAAACTACAA
CTTCAAGCAGAAGAGAGAGGGGTTGTGTCTATCAAAGGAGTGTGTGCAAACCGTTACCTTGCTATGAAAGAAGATGG
AAGATTACTAGCTTCTAAATGTGTTACAGACGAGTGTTTCTTTTTTGAACGATTGGAGTCTAATAACTACAATACTT
ACCGGTCAAGGAAATACACCAGTTGGTATGTGGCACTGAAACGAACTGGGCAGTATAAACTTGGATCCAAAACAGGA
CCTGGGCAGAAAGCTATACTTTTTCTTCCAATGTCTGCTAAGAGCTGATCTTAATGGCAGCATCTGATCTCATTTTA
CATGAAGCTGGTGGCATCCCTGTGACCCCTCCCCAGTGCCTCTCCTGGCCCTGGAAGTTGCCACTCCAGTGCCCACC
AGCCTTGTCCTAATAAAATTAAGTTGCATCATTTTGTCTGACTAGGTGTCCTTCTATAATATTATGGGGTGGAGGGG
GGTGGTATGGAGCAAGGGGCAAGTTGGGAAGACAACCTGTAGGGCCTGCGGGGTCTATTGGGAACCAAGCTGGAGTG
CAGTGGCACAATCTTGGCTCACTGCAATCTCCGCCTCCTGGGTTCAAGCGATTCTCCTGCCTCAGCCTCCCGAGTTG
```

*Fig. 2A*

```
TTGGGATTCCAGGCATGCATGACCAGGCTCAGCTAATTTTTGTTTTTTTGGTAGAGACGGGGTTTCACCATATTGGC
CAGGCTGGTCTCCAACTCCTAATCTCAGGTGATCTACCCACCTTGGCCTCCCAAATTGCTGGGATTACAGGCGTGAA
CCACTGCTCCCTTCCCTGTCCTTCTGATTTTAAAATAACTATACCAGCAGGAGGACGTCCAGACACAGCATAGGCTA
CCTGGCCATGCCCAACCGGTGGGACATTTGAGTTGCTTGCTTGGCACTGTCCTCTCATGCGTTGGGTCCACTCAGTA
GATGCCTGTTGAATTATCGGATCCACTACGCGTTAGAGCTCGCTGATCAGCCTCGACTGTGCCTTCTAGTTGCCAGC
CATCTGTTGTTTGCCCCTCCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGGGGCAGGACAGCAAGGGGGA
GGATTGGGAAGACAATAGCAGGGGGGTGGGCGAAGAACTCCAGCATGAGATCCCCGCGCTGGAGGATCATCCAGCCA
ATTCCCTAGAGCATGGCTACGTAGATAAGTAGCATGGCGGGTTAATCATTAACTACAAGGAACCCCTAGTGATGGAG
TTGGCCACTCCCTCTCTGCGCGCTCGCTCGCTCACTGAGGCCGGGCGACCAAAGGTCGCCCGACGCCCGGGCTTTGC
CCGGGCGGCCTCAGTGAGCGAGCGAGCGCGCAGGGGGTGGGCGAAGAACTCCAGCATGAGATCCCCGCGCTGGAGGA
TCATCCAGCCGGCGTCCCGGAAAACGATTCCGAAGCCCAACCTTTCATAGAAGGCGGCGGTGGAATCGAAATCTCGT
GATGGCAGGTTGGGCGTCGCTTGGTCGGTCATTTCGAACCCCAGAGTCCCGCTCAGAAGAACTCGTCAAGAAGGCGA
TAGAAGGCGATGCGCTGCGAATCGGGAGCGGCGATACCGTAAAGCACGAGGAAGCGGTCAGCCCATTCGCCGCCAAG
CTCTTCAGCAATATCACGGGTAGCCAACGCTATGTCCTGATAGCGGTCCGCCACACCCAGCCGGCCACAGTCGATGA
ATCCAGAAAAGCGGCCATTTTCCACCATGATATTCGGCAAGCAGGCATCGCCATGGGTCACGACGAGATCCTCGCCG
TCGGGCATGCGCGCCTTGAGCCTGGCGAACAGTTCGGCTGGCGCGAGCCCCTGATGCTCTTCGTCCAGATCATCCTG
ATCGACAAGACCGGCTTCCATCCGAGTACGTGCTCGCTCGATGCGATGTTTCGCTTGGTGGTCGAATGGGCAGGTAG
CCGGATCAAGCGTATGCAGCCGCCGCATTGCATCAGCCATGATGGATACTTTCTCGGCAGGAGCAAGGTGAGATGAC
AGGAGATCCTGCCCCGGCACTTCGCCCAATAGCAGCCAGTCCCTTCCCGCTTCAGTGACAACGTCGAGCACAGCTGC
GCAAGGAACGCCCGTCGTGGCCAGCCACGATAGCCGCGCTGCCTCGTCCTGCAGTTCATTCAGGGCACCGGACAGGT
CGGTCTTGACAAAAAGAACCGGGCGCCCCTGCGCTGACAGCCGGAACACGGCGGCATCAGAGCAGCCGATTGTCTGT
TGTGCCCAGTCATAGCCGAATAGCCTCTCCACCCAAGCGGCCGGAGAACCTGCGTGCAATCCATCTTGTTCAATCAT
GCGAAACGATCCTCATCCTGTCTCTTGATCAGATCTTGATCCCCTGCGCCATCAGATCCTTGGCGGCAAGAAAGCCA
TCCAGTTTACTTTGCAGGGCTTCCCAACCTTACCAGAGGGCGCCCCAGCTGGCAATTCCGGTTCGCTTGCTGTCCAT
AAAACCGCCCAGTCTAGCTATCGCCATGTAAGCCCACTGCAAGCTACCTGCTTTCTCTTTGCGCTTGCGTTTTCCCT
TGTCCAGATAGCCCAGTAGCTGACATTCATCCGGGGTCAGCACCGTTTCTGCGGACTGGCTTTCTACGTGTTCCGCT
TCCTTTAGCAGCCCTTGCGCCCTGAGTGCTTGCGGCAGCGTGAAGCTGTCAATTCCGCGTTAAATTTTTGTTAAATC
AGCTCATTTTTTAACCAATAGGCCGAAATCGGCAAAATCCCTTATAAATCAAAAGAATAGCCCGAGATAGGGTTGAG
TGTTGTTCCAGTTTGGAACAAGAGTCCACTATTAAAGAACGTGGACTCCAACGTCAAAGGGCGAAAAACCGTCTATC
AGGGCGATGGCGGATCAGCTTATGCGGTGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAAGAGTTGGTAGCTCTTGATCCGG
CAAACAAACCACCGCTGGTAGCGGCGGTTTTTTGTTTGCAAGCAGCAGATTACGCGCAGAAAAAAAGGATCTCAAGA
AGATCCTTTGATCTTTTCTTACTGAACGGTGATCCCCACCGGAATT
```

*Fig. 2B*

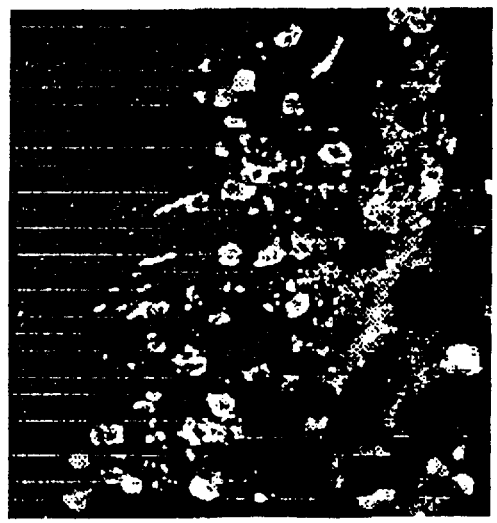
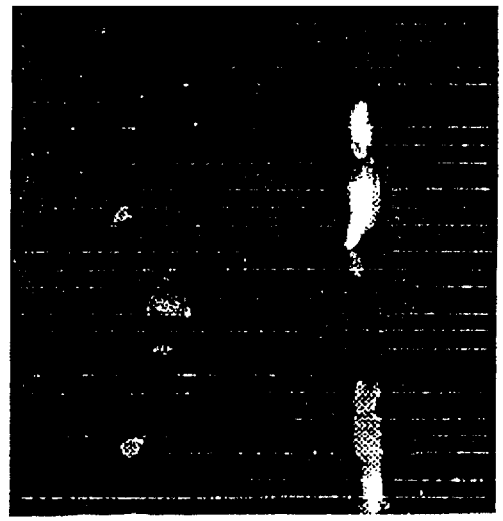
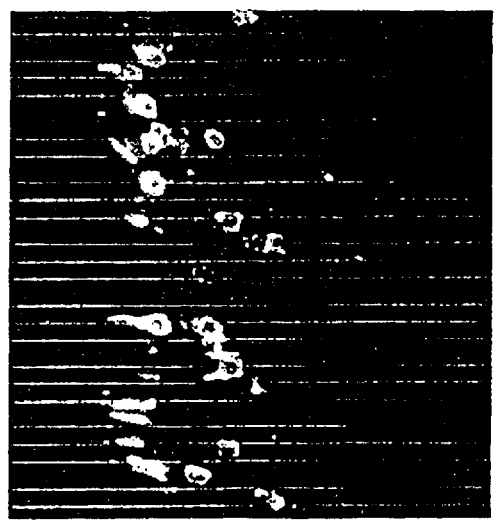
photoreceptors
bipolar cells
ganglion cells
Fig. 15

Nucleotide Sequence of pD10-VEGFuc

```
AAAACTTGCGGCCGCGGAATTTCGACTCTAGGCCATTGCATACGTTGTATCTATATCATAATATGTACATTTATATTGGCTCATGTCCAATATGACCGCCA
TGTTGACATTGATTATTGACTAGTTATTAATAGTAATCAATTACGGGGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTCCGCCCCCTATTGACGTCAATGACGGTAAATGGCCCGCC
TGGCATTATGCCCAGTACATGACCTTACGGGACTTTCCTACTTGGCAGTACATCTACGTATTAGTCATCGCTATTACCATGGTGATGCGGTTTTGGCAGTA
CACCAATGGGCGTGGATAGCGGTTTGACTCACGGGGATTTCCAAGTCTCCACCCCATTGACGTCAATGGGAGTTTGTTTTGGCACCAAAATCAACGGGACT
TTCCAAAATGTCGTAATAACCCCGCCCCGTTGACGCAAATGGGCGGTAGGCGTGTACGGTGGGAGGTCTATATAAGCAGAGCTCGTTTAGTGAACCGTCAG
ATCGCCTGGAGACGCCATCCACGCTGTTTTGACCTCCATAGAAGACACCGGGACCGATCCAGCCTCCGCGGCCGGGAACGGTGCATTGGAACGCGGATTCC
CCGTGCCAAGAGTGACGTAAGTACCGCCTATAGACTCTATAGGCACACCCCTTTGGCTCTTATGCATGCTATACTGTTTTTGGCTTGGGGCCTATACACCC
CCGCTCCTTATGCTATAGGTGATGGTATAGCTTAGCCTATAGGTGTGGGTTATTGACCATTATTGACCACTCCCCTATTGGTGACGATACTTTCCATTACT
AATCCATAACATGGCTCTTTGCCACAACTATCTCTATTGGCTATATGCCAATACTCTGTCCTTCAGAGACTGACACGGACTCTGTATTTTTACAGGATGGG
GTCCATTTATTATTTACAAATTCACATATACAACAACGCCGTCCCCCGTGCCCGCAGTTTTTATTAAACATAGCGTGGGATCTCCGACATCTCGGGTACGT
GTTCCGGACATGGGCTCTTCTCCGGTAGCGGCGGAGCTTCCACATCCGAGCCCTGGTCCCATCCGTCCAGCGGCTCATGGTCGCTCGGCAGCTCCTTGCTC
CTAACAGTGGAGGCCAGACTTAGGCACAGCACAATGCCCACCACCACCAGTGTGCCGCACAAGGCCGTGGCGGTAGGGTATGTGTCTGAAAATGAGCTCGG
AGATTGGGCTCGCACCTGGACGCAGATGGAAGACTTAAGGCAGCGGCAGAAGAAGATGCAGGCAGCTGAGTTGTTGTATTCTGATAAGAGTCAGAGGTAAC
TCCCGTTGCGGTGCTGTTAACGGTGGAGGGCAGTGTAGTCTGAGCAGTACTCGTTGCTGCCGCGCGCCACCAGACATAATAGCTGACAGACTAACAGAC
TGTTCCTTTCCATGGGTCTTTTCTGCAGTCACCGTCGTCGACCTAAGAATTCGCCCTTCGAAACCATGAACTTTCTGCTGTCTTGGGTGCATTGGAGCCTT
GCCTTGCTGCTCTACCTCCACCATGCCAAGTGGTCCCAGGCTGCACCCATGGCAGAAGGAGGAGGGCAGAATCATCACGAAGTGGTGAAGTTCATGGATGT
CTATCAGCGCAGCTACTGCCATCCAATCGAGACCCTGGTGGACATCTTCCAGGAGTACCCTGATGAGATCGAGTACATCTTCAAGCCATCCTGTGTGCCCC
TGATGCGATGCGGGGGCTGCTGCAATGACGAGGGCCTGGAGTGTGTGCCCACTGAGGAGTCCAACATCACCATGCAGATTATGCGGATCAAACCTCACCAA
GGCCAGCACATAGGAGAGATGAGCTTCCTACAGCACAACAAATGTGAATGCAGACCAAAGAAAGATAGAGCAAGACAAGAAAATCCCTGTGGGCCTTGCTC
AGAGCGGAGAAAGCATTTGTTTGTACAAGATCCGCAGACGTGTAAATGTTCCTGCAAAAACACAGACTCGCGTTGCAAGGCGAGGCAGCTTGAGTTAAACG
AACGTACTTGCAGATGTGACAAGCCGAGGCGGTGAGCCGGGCAGGAGGAAGGAGCCTCCCTCAGGGTTTCGGGAACCAGATCTCTCACCAGGAAAGACTGA
TACAGAAAGGGCGAATTCAGGCCTAAGCTTCCTAGGTATCGATCTCGAGCAAGTCTAGAAAGCCATGGATATCGGATCCACTACGCGTTAGAGCTCGCTGA
TCAGCCTCGACTGTGCCTTCTAGTTGCCAGCCATCTGTTGTTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGGGTGGGGCAGGACAGCAAGGGGGAGGATTGGGAAGACAATA
GCAGGGGGTGGGCGAAGAACTCCAGCATGAGATCCCCGCGCTGGAGGATCATCCAGCTAGCAAGTCCCATCAGTGATGGAGTTGGCCACTCCCTCTCTGC
GCGCTCGCTCGCTCACTGAGGCCGGGCGACCAAAGGTCGCCCGACGCCCGGGCTTTGCCCGGGCGGCCTCAGTGAGCGAGCGAGCGCGCCAGCGATTCTCT
TGTTTGCTCCAGACTCTCAGGCAATGACCTGATAGCCTTTGTAGAGACCTCTCAAAAATAGCTACCCTCTCCGGCATGAATTTATCAGCTAGAACGGTTGA
ATATCATATTGATGGTGATTTGACTGTCTCCGGCCTTTCTCACCCGTTTGAATCTTTACCTACACATTACTCAGGCATTGCATTTAAAATATATGAGGGTT
CTAAAAATTTTTATCCTTGCGTTGAAATAAAGGCTTCTCCCGCAAAAGTATTACAGGGTCATAATGTTTTTGGTACAACCGATTTAGCTTTATGCTCTGAG
GCTTTATTGCTTAATTTTGCTAATTCTTTGCCTTGCCTGTATGATTTATTGGATGTTGGAATTCCTGATGCGGTATTTTCTCCTTACGCATCTGTGCGGTA
TTTCACACCGCATATGGTGCACTCTCAGTACAATCTGCTCTGATGCCGCATAGTTAAGCCAGCCCCGACACCCGCCAACACCCGCTGACGCGCCCTGACGG
GCTTGTCTGCTCCCGGCATCCGCTTACAGACAAGCTGTGACCGTCTCCGGGAGCTGCATGTGTCAGAGGTTTTCACCGTCATCACCGAAACGCGCGAGACG
AAAGGGCCTCGTGATACGCCTATTTTTATAGGTTAATGTCATGATAATAATGGTTTCTTAGACGTCAGGTGGCACTTTTCGGGGAAATGTGCGCGGAACCC
CTATTTGTTTATTTTTCTAAATACATTCAAATATGTATCCGCTCATGAGACAATAACCCTGATAAATGCTTCAATAATATTGAAAAAGGAAGAGTATGAGT
```

Fig. 22A

```
ATTCAACATTTCCGTGTCGCCCTTATTCCCTTTTTTGCGGCATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGTAACTCGCCTTGATCGTTGGGAACCGGAGCTGAATGAAGCCA
TACCAAACGACGAGCGTGACACCACGATGCCTGTAGCAATGGCAACAACGTTGCGCAAACTATTAACTGGCGAACTACTTACTCTAGCTTCCCGGCAACAA
TTAATAGACTGGATGGAGGCGGATAAAGTTGCAGGACCACTTCTGCGCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTCCTTCTAGTGTAGCCGTAGTTAGGCCACCACTTCAAGAAC
TCTGTAGCACCGCCTACATACCTCGCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATGCTCGTCAGGGGGGCGGAGCCTATGGAAAAA
CGCCAGCAACGCGGCCTTTTTACGGTTCCTGGCCTTTTGCTGGCCTTTTGCTCACATGTTCTTTCCTGCGTTATCCCCTGATTCTGTGGATAACCGTATTA
CCGCCTTTGAGTGAGCTGATACCGCTCGCCGCAGCCGAACGACCGAGCGCAGCGAGTCAGTGAGCGAGGAAGCGGAAGAGCGCCCAATACGCAAACCGCCT
CTCCCCGCGCGTTGGCCGATTCATTAATGCAGCTGGCGCGCTCGCTCGCTCACTGAGGCCGCCCGGGCAAAGCCCGGGCGTCGGGCGACCTTTGGTCGCCC
GGCCTCAGTGAGCGAGCGAGCGCGCAGAGAGGGAGTGGCCAACTCCATCACTGAT
```

Fig. 22B

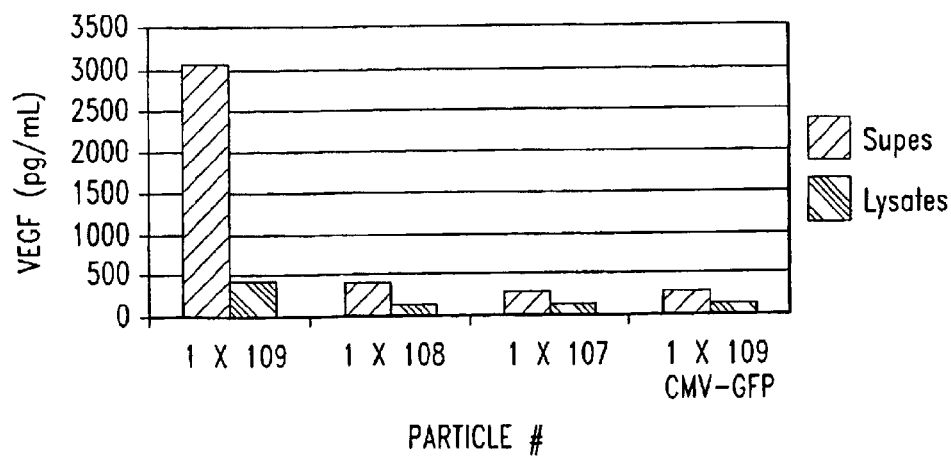

Fig. 23

Nucleotide Sequence of pD10-SFlt-1

```
AAAACTTGCGGCCGCGGAATTTCGACTCTAGGCCATTGCATACGTTGTATCTATATCATAATATGTACATTTATATTGGCTCATGTCCAATATGACCGC
CATGTTGACATTGATTATTGACTAGTTATTAATAGTAATCAATTACGGGGTCATTAGTTCATAGCCCATATATGGAGTTCCGCGTTACATAACTTACGG
TAAATGGCCCGCCTGGCTGACCGCCCAACGACCCCCGCCCATTGACGTCAATAATGACGTATGTTCCCATAGTAACGCCAATAGGGACTTTCCATTGAC
GTCAATGGGTGGAGTATTTACGGTAAACTGCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATTAGTCATCGCTATTACCATGGTGATGCGGT
TTTGGCAGTACACCAATGGGCGTGGATAGCGGTTTGACTCACGGGGATTTCCAAGTCTCCACCCCATTGACGTCAATGGGAGTTTGTTTTGGCACCAAA
ATCAACGGGACTTTCCAAAATGTCGTAATAACCCCGCCCCGTTGACGCAAATGGGCGGTAGGCGTGTACGGTGGGAGGTCTATATAAGCAGAGCTCGTT
TAGTGAACCGTCAGATCGCCTGGAGACGCCATCCACGCTGTTTTGACCTCCATAGAAGACACCGGGACCGATCCAGCCTCCGCGGCCGGGAACGGTGCA
TTGGAACGCGGATTCCCCGTGCCAAGAGTGACGTAAGTACCGCCTATAGACTCTATAGGCACACCCCTTTGGCTCTTATGCATGCTATACTGTTTTTGG
CTTGGGGCCTATACACCCCCGCTCCTTATGCTATAGGTGATGGTATAGCTTAGCCTATAGGTGTGGGTTATTGACCATTATTGACCACTCCCCTATTGG
TGACGATACTTTCCATTACTAATCCATAACATGGCTCTTTGCCACAACTATCTCTATTGGCTATATGCCAATACTCTGTCCTTCAGAGACTGACACGGA
CTCTGTATTTTTACAGGATGGGGTCCATTTATTATTTACAAATTCACATATACAACAACGCCGTCCCCCGTGCCCGCAGTTTTTATTAAACATAGCGTG
GGATCTCCGACATCTCGGGTACGTGTTCCGGACATGGGCTCTTCTCCGGTAGCGGCGGAGCTTCCACATCCGAGCCCTGGTCCCATCCGTCCAGCGGCT
CATGGTCGCTCGGCAGCTCCTTGCTCCTAACAGTGGAGGCCAGACTTAGGCACAGCACAATGCCCACCACCACCAGTGTGCCGCACAAGGCCGTGGCGG
TAGGGTATGTGTCTGAAAATGAGCTCGGAGATTGGGCTCGCACCTGGACGCAGATGGAAGACTTAAGGCAGCGGCAGAAGAAGATGCAGGCAGCTGAGT
TGTTGTATTCTGATAAGAGTCAGAGGTAACTCCCGTTGCGGTGCTGTTAACGGTGGAGGGCAGTGTAGTCTGAGCAGTACTCGTTGCTGCCGCGCGCGC
CACCAGACATAATAGCTGACAGACTAACAGACTGTTCCTTTCCATGGGTCTTTTCTGCAGTCACCGTCGTCGACCTAAGAATTCGCCCTTTCACCATGG
TCAGCTACTGGGACACCGGGGTCCTGCTGTGCGCGCTGCTCAGCTGTCTGCTTCTCACAGGATCTAGTTCAGGTTCAAAATTAAAAGATCCTGAACTGA
GTTTAAAAGGCACCCAGCACATCATGCAAGCAGGCCAGACACTGCATCTCCAATGCAGGGGGGAAGCAGCCCATAAATGGTCTTTGCCTGAAATGGTGA
GTAAGGAAAGCGAAAGGCTGAGCATAACTAAATCTGCCTGTGGAAGAAATGGCAAACAATTCTGCAGTACTTTAACCTTGAACACAGCTCAAGCAAACC
ACACTGGCTTCTACAGCTGCAAATATCTAGCTGTACCTACTTCAAAGAAGAAGGAAACAGAATCTGCAATCTATATATTTATTAGTGATACAGGTAGAC
CTTTCGTAGAGATGTACAGTGAAATCCCCGAAATTATACACATGACTGAAGGAAGGGAGCTCGTCATTCCCTGCCGGGTTACGTCACCTAACATCACTG
TTACTTTAAAAAAGTTTCCACTTGACACTTTGATCCCTGATGGAAAACGCATAATCTGGGACAGTAGAAAGGGCTTCATCATATCAAATGCAACGTACA
AAGAAATAGGGCTTCTGACCTGTGAAGCAACAGTCAATGGGCATTTGTATAAGCAAACTATCTCACACATCGACAAACCAATACAATCATAGATGTCC
AAATAAGCACACCACGCCCAGTCAAATTACTTAGAGGCCATACTCTTGTCCTCAATTGTACTGCTACCACTCCCTTGAACACGAGAGTTCAAATGACCT
GGAGTTACCCTGATGAAAAAAATAAGAGAGCTTCCGTAAGGCGACGAATTGACCAAAGCAATTCCCATGCCAACATATTCTACAGTGTTCTTACTATTG
ACAAAATGCAGAACAAAGACAAAGGACTTTATACTTGTCGTGTAAGGAGTGGACCATCATTCAAATCTGTTAACACCTCAGTGCATATATATGATAAAG
CATTCATCACTGTGAAACATCGAAAACAGCAGGTGCTTGAAACCGTAGCTGGCAAGCGGTCTTACCGGCTCTCTATGAAAGTGAAGGCATTTCCCTCGC
CGGAAGTTGTATGGTTAAAAGATGGGTTACCTGCGACTGAGAAATCTGCTCGCTATTTGACTCGTGGCTACTCGTTAATTATCAAGGACGTAACTGAAG
AGGATGCAGGGAATTATACAATCTTGCTGAGCATAAAACAGTCAAATGTGTTTAAAAACCTCACTGCCACTCTAATTGTCAATGTGAAACCCCAGATTT
ACGAAAAGGCCGTGTCATCGTTTCCAGACCCCGGCTCTCTACCCACTGGGCAGCAGACAAATCCTGACTTGTACCGCATATGGTATCCCTCAACCTACAA
TCAAGTGGTTCTGGCACCCCTGTAACCATAATCATTCCGAAGCAAGGTGTGACTTTTGTTCCAATAATGAAGAGTCCTTTATCCTGGATGCTGACAGCA
ACATGGGAAACAGAATTGAGAGCATCACTCAGCGCATGGCAATAATAGAAGGAAAGAATAAGATGGCTAGCACCTTGGTTGTGGCTGACTCTAGAATTT
CTGGAATCTACATTTGCATAGCTTCCAATAAAGTTGGGACTGTGGGAAGAAACATAAGCTTTTATATCACAGATGTGCCAAATGGGTTTCATGTTAACT
TGGAAAAAAATGCCGACGGAAGGAGAGGACCTGAAACTGTCTTGCACAGTTAACAAGTTCTTATACAGAGACGTTACTTGGATTTTACTGCGGACAGTTA
ATAACAGAACAATGCACTACAGTATTAGCAAGCAAAAAATGGCCATCACTAAGGAGCACTCCATCACTCTTAATCTTACCATCATGAATGTTTCCCTGC
AAGATTCAGGCACCTATGCCTGCAGAGCCAGGAATGTATACACAGGGGAAGAAATCCTCAGAAGAAAGAAATTACAATCAGAGGTGAGCACTGCAACA
AAAAGGCTGTTTTCTCTCGGATCTCCAAATTTAAAAGCACAAGGAATGATTGTACCACACAAAGTAATGTAAAACATTAAAGGACTCATTAAAAAGTAA
CAGTTGTCTCATATCATCTTGATTTATTGTCACTGTTGCTAACTTTCAGGCTCAAGGGCGAATTCAGGCCTAAGCTTCCTAGGTATCGATCTCGAGCAA
GTCTAGAAAGCCATGGATATCGGATCCACTACGCGTTAGAGCTCGCTGATCAGCCTCGACTGTGCCTTCTAGTTGCCAGCCATCTGTTGTTTGCCCCTC
```

*Fig. 28A*

```
CCCCGTGCCTTCCTTGACCCTGGAAGGTGCCACTCCCACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGGGGGGTGGGCGAAGAACTCCAGCATGAGATCCCCGCGCTGGA
GGATCATCCAGCTAGCAAGTCCCATCAGTGATGGAGTTGGCCACTCCCTCTCTGCGCGCTCGCTCGCTCACTGAGGCCGGGCGACCAAAGGTCGCCCGA
CGCCCGGGCTTTGCCCGGGCGGCCTCAGTGAGCGAGCGAGCGCGCCAGCGATTCTCTTGTTTGCTCCAGACTCTCAGGCAATGACCTGATAGCCTTTGT
AGAGACCTCTCAAAAATAGCTACCCTCTCCGGCATGAATTTATCAGCTAGAACGGTTGAATATCATATTGATGGTGATTTGACTGTCTCCGGCCTTTCT
CACCCGTTTGAATCTTTACCTACACATTACTCAGGCATTGCATTTAAAATATATGAGGGTTCTAAAAATTTTTATCCTTGCGTTGAAATAAAGGCTTCT
CCCGCAAAAGTATTACAGGGTCATAATGTTTTTGGTACAACCGATTTAGCTTTATGCTCTGAGGCTTTATTGCTTAATTTTGCTAATTCTTTGCCTTGC
CTGTATGATTTATTGGATGTTGGAATTCCTGATGCGGTATTTTCTCCTTACGCATCTGTGCGGTATTTCACACCGCATATGGTGCACTCTCAGTACAAT
CTGCTCTGATGCCGCATAGTTAAGCCAGCCCCGACACCCGCCAACACCCGCTGACGCGCCCTGACGGGCTTGTCTGCTCCCGGCATCCGCTTACAGACA
AGCTGTGACCGTCTCCGGGAGCTGCATGTGTCAGAGGTTTTCACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAATGTGCGCGGAACCCCTATTTGTTTATTTTTCTAAATACATTC
AAATATGTATCCGCTCATGAGACAATAACCCTGATAAATGCTTCAATAATATTGAAAAAGGAAGAGTATGAGTATTCAACATTTCCGTGTCGCCCTTAT
TCCCTTTTTTGCGGCATTTTGCCTTCCTGTTTTTGCTCACCCAGAAACGCTGGTGAAAGTAAAAGATGCTGAAGATCAGTTGGGTGCACGAGTGGGTTA
CATCGAACTGGATCTCAACAGCGGTAAGATCCTTGAGAGTTTTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCTCAGAATGACTTGGTTGAGTACTCACCAGTCACAGAAAAGCA
TCTTACGGATGGCATGACAGTAAGAGAATTATGCAGTGCTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGGGAACCGGAGCTGAATGAAGCCATACCAAACGACGAGCG
TGACACCACGATGCCTGTAGCAATGGCAACAACGTTGCGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATTGCTGATAAATCTGGAGCCGGTGAGCGTGGGTCTCGCGG
TATCATTGCAGCACTGGGGCCAGATGGTAAGCCCTCCCGTATCGTAGTTATCTACACGACGGGGAGTCAGGCAACTATGGATGAACGAAATAGACAGAT
CGCTGAGATAGGTGCCTCACTGATTAAGCATTGGTAACTGTCAGACCAAGTTTACTCATATATACTTTAGATTGATTTAAAACTTCATTTTTAATTTAA
AAGGATCTAGGTGAAGATCCTTTTTGATAATCTCATGACCAAAATCCCTTAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACACCGAACTGAGATACCTACAGCG
TGAGCTATGAGAAAGCGCCACGCTTCCCGAAGGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGAGGAAGCGGAAGAGCGCCCAATACG
CAAACCGCCTCTCCCCGCGCGTTGGCCGATTCATTAATGCAGCTGGCGCGCTCGCTCGCTCACTGAGGCCGCCCGGGCAAAGCCCGGGCGTCGGGCGAC
CTTTGGTCGCCCGGCCTCAGTGAGCGAGCGAGCGCGCAGAGAGGGAGTGGCCAACTCCATCACTGAT
```

*Fig. 28B*

HumanFGF-20 atggctcccttagccgaagtcggggggctttctgggcggcctggagggcttgggccagcag
M  A  P  L  A  E  V  G  G  F  L  G  G  L  E  G  L  G  Q  Q gtgggttcgcatttcctgttgcctcctgccggggagcggccgccgctgctgggcgagcgc
V  G  S  H  F  L  L  P  P  A  G  E  R  P  P  L  L  G  E  R aggagcgcggcggagcggagcgcgcgcggcgggccgggggctgcgcagctggcgcacctg
R  S  A  A  E  R  S  A  R  G  G  P  G  A  A  Q  L  A  H  L cacggcatcctgcgccgccggcagctctattgccgcaccggcttccacctgcagatcctg
H  G  I  L  R  R  R  Q  L  Y  C  R  T  G  F  H  L  Q  I  L cccgacggcagcgtgcagggcaccccggcaggaccacagcctcttcggtatcttggaattc
P  D  G  S  V  Q  G  T  R  Q  D  H  S  L  F  G  I  L  E  F atcagtgtggcagtgggactggtcagtattagaggtgtggacagtggtctctatcttgga
I  S  V  A  V  G  L  V  S  I  R  G  V  D  S  G  L  Y  L  G atgaatgacaaaggagaactctatggatcagagaaacttacttccgaatgcatctttagg
M  N  D  K  G  E  L  Y  G  S  E  K  L  T  S  E  C  I  F  R gagcagtttgaagagaactggtataacacctattcatctaacatatataaacatggagac
E  Q  F  E  E  N  W  Y  N  T  Y  S  S  N  I  Y  K  H  G  D actggccgcaggtattttgtggcacttaacaaagacggaactccaagagatggcgccagg
T  G  R  R  Y  F  V  A  L  N  K  D  G  T  P  R  D  G  A  R tccaagaggcatcagaaatttacacatttcttacctagaccagtggatccagaaagagtt
S  K  R  H  Q  K  F  T  H  F  L  P  R  P  V  D  P  E  R  V ccagaattgtacaaggacctactgatgtacacttga
P  E  L  Y  K  D  L  L  M  Y  T

*Fig. 29*

Mouse FGF-21 cDNA in pGEM-T gagcgcagccctgatggaatggatgagatctagagttgggaccctgggactgtgggtccg    SEQ ID NO: 6
       M  E  W  M  R  S  R  V  G  T  L  G  L  W  V  R    SEQ ID NO: 7 actgctgctggctgtcttcctgctgggggtctaccaagcatacccccatccctgactccag
 L  L  L  A  V  F  L  L  G  V  Y  Q  A  Y  P  I  P  D  S  S ccccctcctccagtttgggggtcaagtccggcagaggtacctctacacagatgacgacca
 P  L  L  Q  F  G  G  Q  V  R  Q  R  Y  L  Y  T  D  D  D  Q agacactgaagcccacctggagatcagggaggatggaacagtggtaggcgcagcacaccg
 D  T  E  A  H  L  E  I  R  E  D  G  T  V  V  G  A  A  H  R cagtccagaaagtctcctggagctcaaagccttgaagccaggggtcattcaaatcctggg
 S  P  E  S  L  L  E  L  K  A  L  K  P  G  V  I  Q  I  L  G tgtcaaagcctctaggtttctttgccaacagccagatggagctctctatggatcgcctca
 V  K  A  S  R  F  L  C  Q  Q  P  D  G  A  L  Y  G  S  P  H ctttgatcctgaggcctgcagcttcagagaactgctgctggaggacggttacaatgtgta
 F  D  P  E  A  C  S  F  R  E  L  L  E  D  G  Y  N  V  Y ccagtctgaagcccatggcctgcccctgcgtctgcctcagaaggactccccaaaccagga
 Q  S  E  A  H  G  L  P  L  R  L  P  Q  K  D  S  P  N  Q  D tgcaacatcctggggacctgtgcgcttcctgcccatgccaggcctgctccacgagcccca
 A  T  S  W  G  P  V  R  F  L  P  M  P  G  L  L  H  E  P  Q agaccaagcaggattcctgccccagagcccccagatgtgggctcctctgacccctgag
 D  Q  A  G  F  L  P  P  E  P  P  D  V  G  S  S·D  P  L  S catggtagagcctttacagggccgaagccccagctatgcgtcctgactcttcctgaatc
 M  V  E  P  L  Q  G  R  S  P  S  Y  A  S

*Fig. 30*

```
AAAACTTGCGGCCGCGGAATTTCGACTCTAGGCCATTGCATACGTTGTATCTATATCATAATATGTACATTTATATTGGCTCATGTCCAATATGACC
GCCATGTTGACATTGATTATTGACTAGTTATTAATAGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATGACGTATGTTCCCATAGTAACGCCAATAGGGACTTTCC
ATTGACGTCAATGGGTGGAGTATTTACGGTAAACTGCCCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTGGCAGTACATCTACGTATTAGTCATCGCTATTACCATG
GTGATGCGGTTTTGGCAGTACACCAATGGGCGTGGATAGCGGTTTGACTCACGGGGATTTCCAAGTCTCCACCCCATTGACGTCAATGGGAGTTTGT
TTTGGCACCAAAATCAACGGGACTTTCCAAAATGTCGTAATAACCCCGCCCCGTTGACGCAAATGGGCGGTAGGCGTGTACGGTGGGAGGTCTATAT
AAGCAGAGCTCGTTTAGTGAACCGTCAGATCGCCTGGAGACGCCATCCACGCTGTTTTGACCTCCATAGAAGACACCGGGACCGATCCAGCCTCCGC
GGCCGGGAACGGTGCATTGGAACGCGGATTCCCCGTGCCAAGAGTGACGTAAGTACCGCCTATAGACTCTATAGGCACACCCCTTTGGCTCTTATGC
ATGCTATACTGTTTTTGGCTTGGGGCCTATACACCCCCGCTCCTTATGCTATAGGTGATGGTATAGCTTAGCCTATAGGTGTGGGTTATTGACCATT
ATTGACCACTCCCCTATTGGTGACGATACTTTCCATTACTAATCCATAACATGGCTCTTTGCCACAACTATCTCTATTGGCTATATGCCAATACTCT
GTCCTTCAGAGACTGACACGGACTCTGTATTTTTACAGGATGGGGTCCATTTATTATTTACAAATTCACATATACAACAACGCCGTCCCCCGTGCCC
GCAGTTTTTATTAAACATAGCGTGGGATCTCCGACATCTCGGGTACGTGTTCCGGACATGGGCTCTTCTCGGGTAGCGGCGGAGCTTCCACATCCGA
GCCCTGGTCCCATCCGTCAGCGGCTCATGGTCGCTCGGCAGCTCCTTGCTCCTAACAGTGGAGGCCAGACTTAGGCACAGCACAATGCCCACCACC
ACCAGTGTGCCGCACAAGGCCGTGGCGGTAGGGTATGTGTCTGAAAATGAGCTCGGAGATTGGGCTCGCACCTGGACGCAGATGGAAGACTTAAGGC
AGCGGCAGAAGAAGATGCAGGCAGCTGAGTTGTTGTATTCTGATAAGAGTCAGAGGTAACTCCCGTTGCGGTGCTGTTAACGGTGGAGGGCAGTGTA
GTCTGAGCAGTACTCGTTGCTGCCGCGCGCGCCACCAGACATAATAGCTGACAGACTAACAGACTGTTCCTTTCCATGGGTCTTTTCTGCAGTCACC
GTCGTCGACCTAAGAATTCAGGTATGGCTGCTGGTTCTATCACTACCCTGCCAGCTCTGCCAGAAGACGGTGGTTCTGGTGCCTTCCCACCAGGTCA
CTTCAAAGACCCAAAACGTCTGTACTGCAAAAACGGTGGTTTCTTCCTGCGCATCCACCCCGACGGCCGAGTGGACGGGGTCCGCGAGAAGAGCGAC
CCACACATCAAACTACAACTTCAAGCAGAAGAGAGGGGTTGTGTCTATCAAAGGAGTGTGTGCAAACCGTTACCTTGCTATGAAAGAAGATGGAA
GATTACTAGCTTCTAAATGTGTTACAGACGAGTGTTTCTTTTTTGAACGATTGGAGTCTAATAACTACAATACTTACCGGTCAAGGAAATACACCAG
TTGGTATGTGGCACTGAAACGAACTGGGCAGTATAAACTTGGATCCAAAACAGGACCTGGGCAGAAAGCTATACTTTTTCTTCCAATGTCTGCTAAG
AGCTGATCTTAATGGCAGCATCTGATCTCATTTTACATGAAGCTTCCTAGGTATCGATCTCGAGCAAGTCTAGAAAGCCATGGATATCGGATCCACT
ACGCGTTAGAGCTCGCTGATCAGCCTCGACTGTGCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTCATTCTATTCTGGGGGGTGGGGTGGGCAGGACA
GCAAGGGGGAGGATTGGGAAGACAATAGCAGGGGGGTGGGCGAAGAACTCCAGCATGAGATCCCCGCGCTGGAGGATCATCCAGCTAGCAAGTCCCA
TCAGTGATGGAGTTGGCCACTCCCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCCAGCGATTCTCTTGTTTGCTCCAGACTCTCAGGCAATGACCTGATAGCCTTTGTAGAGACCTCTCAAAAATAGC
TACCCTCTCCGGCATGAATTTATCAGCTAGAACGGTTGAATATCATATTGATGGTGATTTGACTGTCTCCGGCCTTTCTCACCCGTTTGAATCTTTA
CCTACACATTACTCAGGCATTGCATTTAAAATATATGAGGGTTCTAAAAATTTTTATCCTTGCGTTGAAATAAAGGCTTCTCCCGCAAAAGTATTAC
AGGGTCATAATGTTTTTGGTACAACCGATTTAGCTTTATGCTCTGAGGCTTTATTGCTTAATTTTGCTAATTCTTTGCCTTGCCTGTATGATTTATT
GGATGTTGGAATTCCTGATGCGGTATTTTCTCCTTACGCATCTGTGCGGTATTTCACACCGCATATGGTGCACTCTCAGTACAATC
```

Fig. 32A

```
TGCTCTGATGCCGCATAGTTAAGCCAGCCCCGACACCCGCCAACACCCGCTGACGCGCCCTGACGGGCTTGTCTGCTCCCGGCATCCGCTTACAGAC
AAGCTGTGACCGTCTCCGGGAGCTGCATGTGTCAGAGGTTTTCACCGTCATCACCGAAACGCGCGAGACGAAAGGGCCTCGTGATACGCCTATTTTT
ATAGGTTAATGTCATGATAATAATGGTTTCTTAGACGTCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATGTACCCGTCAAGAAGGCGATAGAAGGCGATGCGCTGCGAATC
GGGAGCGGCGATACCGTAAAGCACGAGGAAGCGGTCAGCCCATTCGCTTCAGCAATATCACGGGTAGCCAACGCTATGTCCTGATAGCGGTCCGCCA
CACCCAGCCGGCCACAGTCGATGAATCCAGAAAAGCGGCCATTTTCCACCATGATATTCGGCAAGCAGGCATCGCCATGGGTCACGACGAGATCCTC
GCCGTCGGGCATGCGCGCCTTGAGCCTGGCGAACAGTTCGGCTGGCGCGAGCCCCTGATGCTCTTCGTCCAGATCATCCTGATCGACAAGACCGGCT
TCCATCCGAGTACGTGCTCGCTCGATGCGATGTTTCGCTTGGTGGTCGAATGGGCAGGTAGCCGGATCAAGCGTATGCAGCCGCCGCATTGCATCAG
CCATGATGGATACTTTCTCGGCAGGAGCAAGGTGAGATGACAGGAGATCCTGCCCCGGCACTTCGCCCAATAGCAGCCAGTCCCTTCCCGCTTCAGT
GACAACGTCGAGCACAGCTGCGCAAGGAACGCCCGTCGTGGCCAGCCACGATAGCCGCGCTGCCTCGTCCTGCAGTTCATTCAGGGGCACCGGACAGG
TCGGTCTTGACAAAAAGAACCGGGCGCCCCTGCGCTGACAGCCGGAACACGGCGGCATCAGAGCAGCCGATTGTCTGTTGTGCCCAGTCATAGCCGA
ATAGCCTCTCCACCCAAGCGGCCGGAGAACCTGCGTGCAATCCATCTTGTTCAATCATGCGAAACGATCCTCATCCTGTCTCTTGATCAGATCTTGA
TCCCCTGCGCCATCAGATCCTTGGCGGCAAGAAAGCCATCCAGTTTACTTTGCAGGGCTTCCCAACCTTACCAGAGGGCGCCCCAGCTGGCAATTCC
GGTTCGCTTGCTGTCCATAAAACCGCCCAGTCTAGCTATCGCCATGTAAGCCCACTGCAAGCTACCTGCTTTCTCTTTGCGCTTGCGTTTTCCCTTG
TCCAGATAGCCCAGTAGCTGACATTCATCCGGGGTCAGCACCGTTTCTGCGGACTGGCTTTCTACGTGTTCCGCTTCCTTTAGCAGCCCTTGCGCCC
TGAGTGCTTGCGGCAGCGTGAAGCTGTCAATTCCGCGTTAAATTTTTGTTAAATCAGCTCATTTTTTAACCAATAGGCCGAAATCGGCAAAATCCCT
TATAAATCAAAAGAATAGCCCGAGATAGGGTTGAGTGTTGTTCCAGTTTGGAACAAGAGTCCACTATTAAAGAACGTGGACTCCAACGTCAAAGGGC
GAAAAACCGTCTATCAGGGCGATGGCGGATCAGCTTATGCGGTGTGAAATACCGCACAGATGCGTAAGGAGAAAATACCGCATCAGGCGCTCTTCCG
CTTCCTCGCTCACTGACTCGCTGCGCTCGGTCGTTCGGCTGCGGCGAGCGGTATCAGCTCACTCAAAGGCGGTAATACGGTTATCCACAGAATCAGG
GGATAACGCAGGAAAGAACATGCGGCGCGCCACATGTGAGCAAAAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGACAGTATTTGGTATCTGCGCTCTGCTGAAGCCAGTTACCTTCGGAAAA
AGAGTTGGTAGCTCTTGATCCGGCAAACAAACCACCGCTGGTAGCGGCGGTTTTTTGTTTGCAAGCAGCAGATTACGCGCAGAAAAAAAGGATCTCA
AGAAGATCCTTTGATCTTTTCTTACTGAACGGTGATCCCCACCGGAATTGCGGCCCATGTTCTTTCCTGCGTTATCCCCTGATTCTGTGGATAACCG
TATTACCGCCTTTGAGTGAGCTGATACCGCTCGCCGCAGCCGAACGACCGAGCGCAGCGAGTCAGTGAGCGAGGAAGCGGAAGAGCGCCCAATACGC
AAACCGCCTCTCCCCGCGCGTTGGCCGATTCATTAATGCAGCTGGCGCGCTCGCTCGCTCACTGAGGCCGCCCGGGCAAAGCCCGGGCGTCGGGCGA
CCTTTGGTCGCCCGGCCTCAGTGAGCGAGCGAGCGCGCAGAGAGGGAGTGGCCAACTCCATCACTGAT
```

*Fig. 32B*

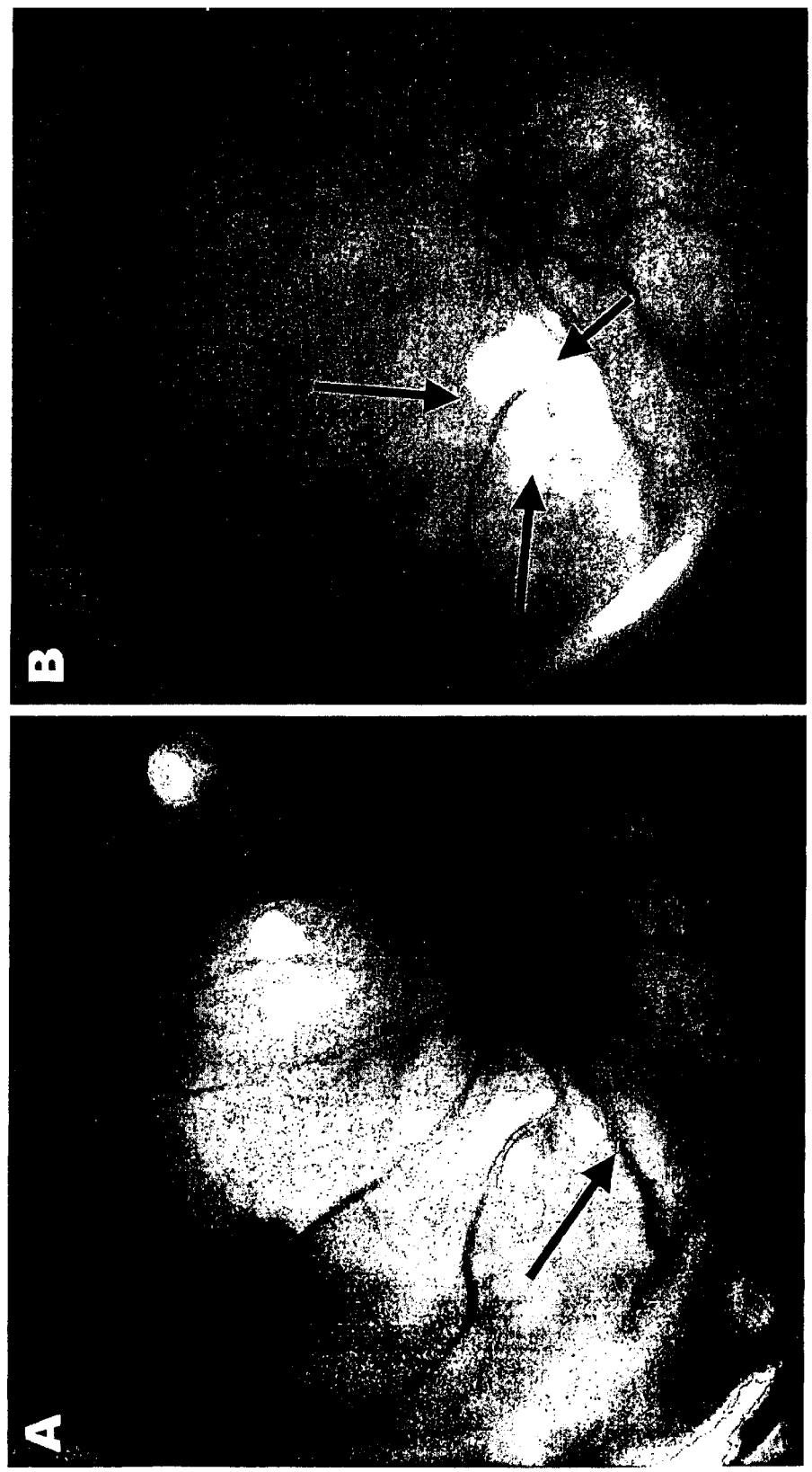
Figure 35. Fluorescein Angiography

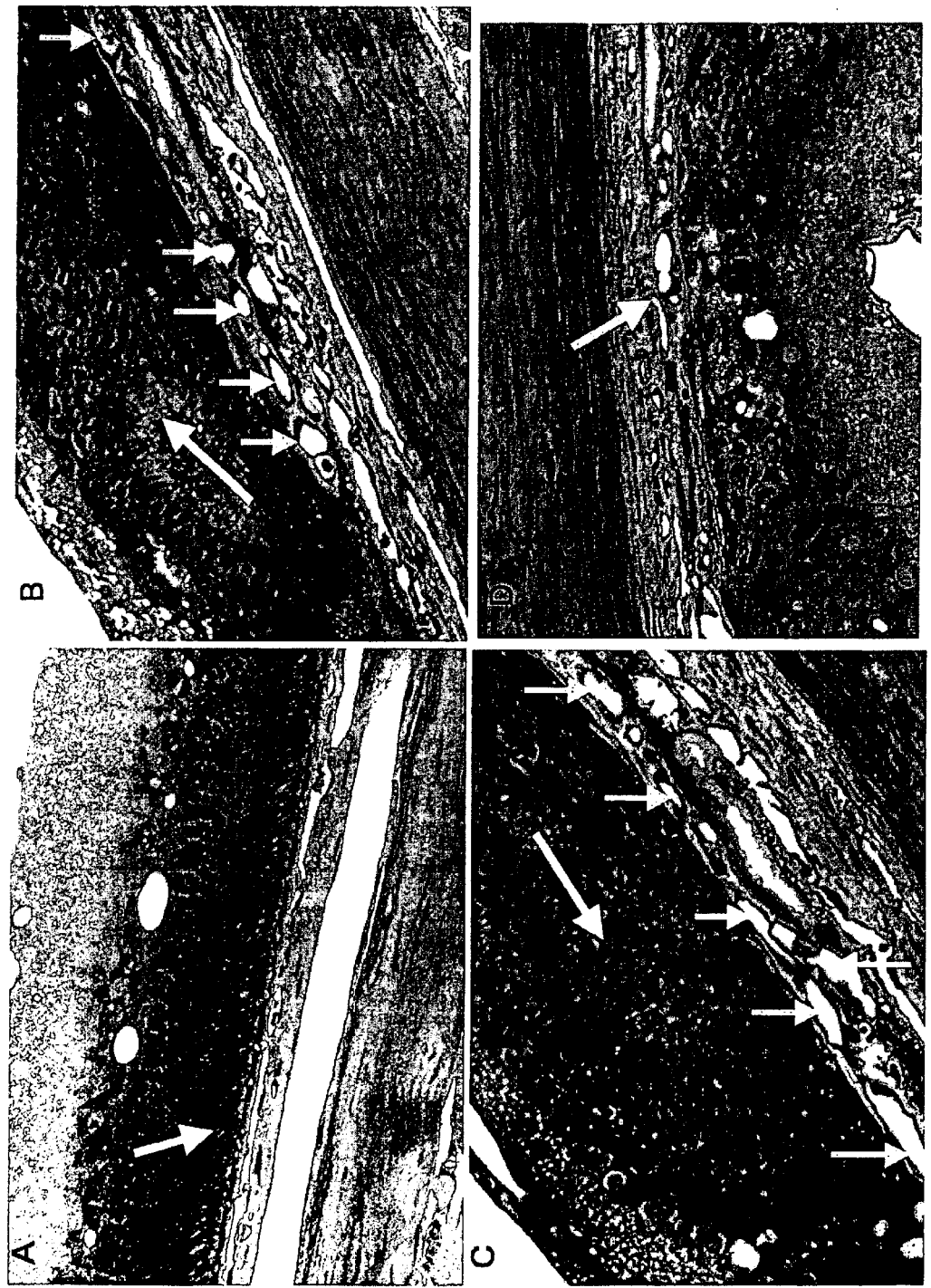
Figure 36. Epoxy Sections

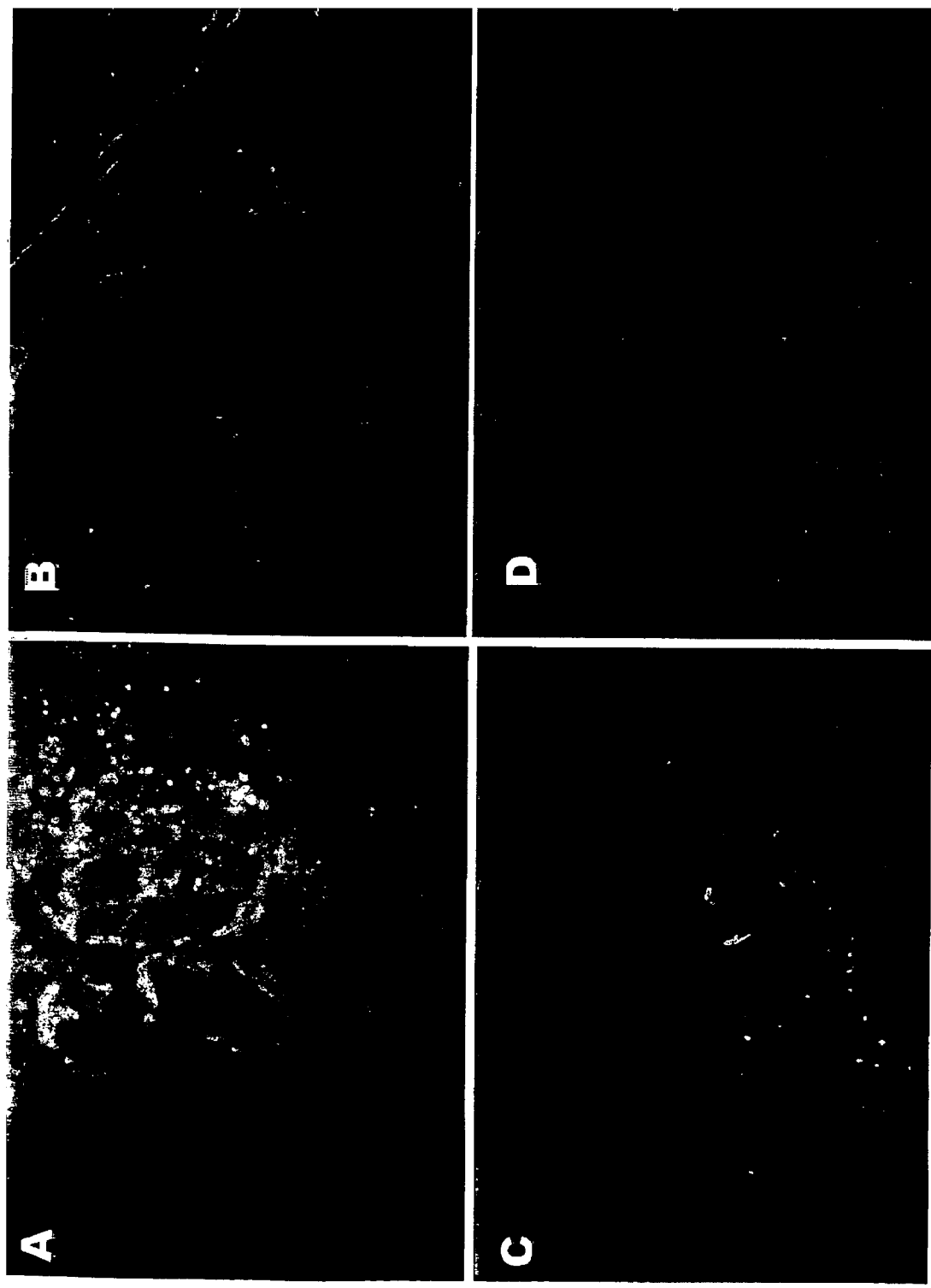
Figure 37. Lectin and BrdU staining

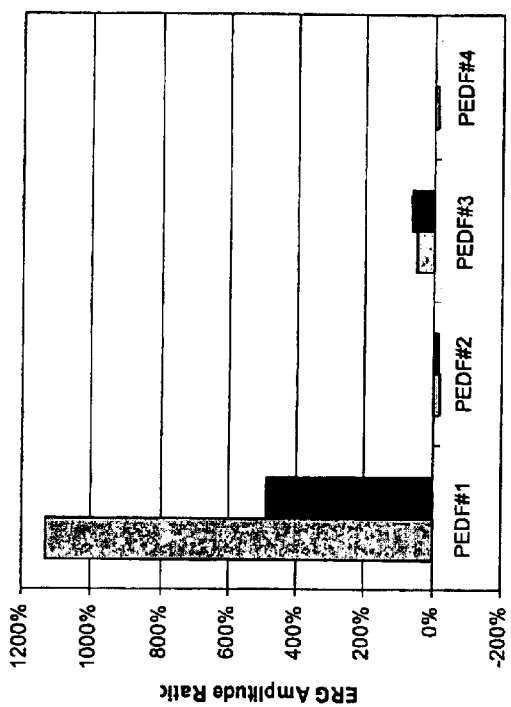
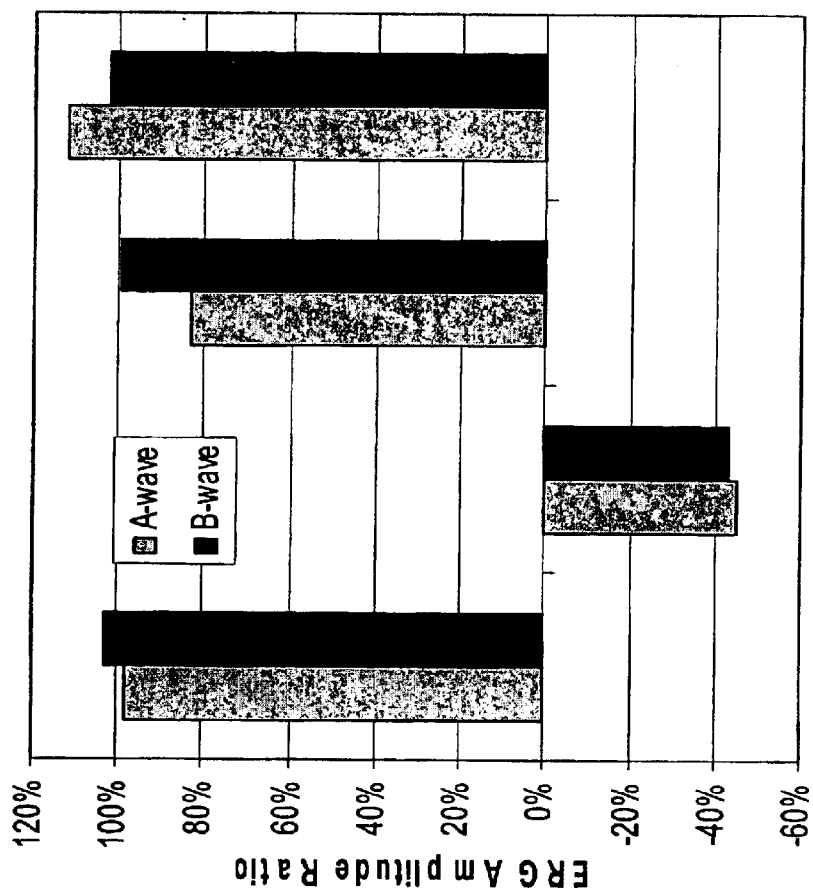

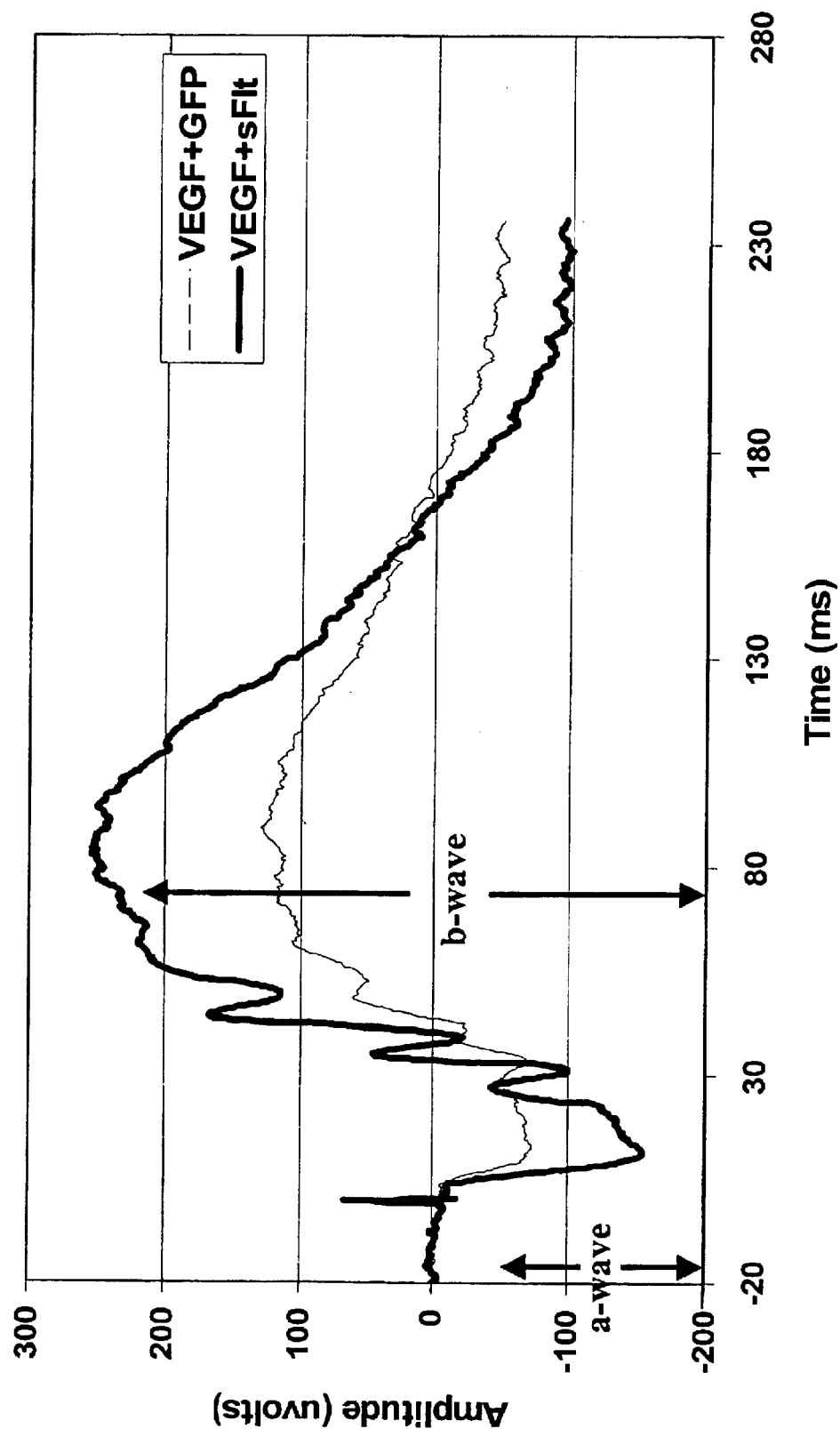
Figure 39. ERG of 070900 Rat#4 on 082300 (6 wk)

USE OF RECOMBINANT GENE DELIVERY VECTORS FOR TREATING OR PREVENTING DISEASES OF THE EYE

CROSS-REFERENCE TO RELATED APPLICATIONS

This application is a continuation-in-part of U.S. patent application Ser. No. 09/525,956, filed Mar. 15, 2000, now abandoned, which application claims priority to U.S. Provisional Application No. 60/124,460, filed Mar. 15, 1999, and U.S. Provisional Application No. 60/174,984, filed Jan. 6, 2000, all of which applications are incorporated by reference in their entirety.

TECHNICAL FIELD

The present invention relates generally to compositions and methods for treating diseases of the eye, and more specifically, to the use of various gene delivery vectors which direct the expression of selected gene products suitable for treating or preventing diseases of the eye.

BACKGROUND OF THE INVENTION

Eye diseases represent a significant health problem in the United States and world-wide. Presently, over 80 million Americans are affected with potentially blinding eye disease, with 1.1 million being legally blind. Twelve million individuals suffer from some degree of visual impairment that cannot be corrected. The total economic impact of eye disease is also very significant. In 1981, the estimated economic impact of visual impairment on the U.S. economy was 14 billion per year. By 1995, this impact had grown to an estimated 38.4 billion (National Eye Institute NIH).

A wide variety of eye diseases can cause visual impairment, including for example, macular degeneration, diabetic retinopathies, inherited retinal degeneration such as retinitis pigmentosa, glaucoma, retinal detachment or injury and retinopathies (whether inherited, induced by surgery, trauma, a toxic compound or agent, or, photically).

One structure in the eye that can be particularly affected by disease is the retina. Briefly, the retina, which is found at the back of the eye, is a specialized light-sensitive tissue that contains photoreceptor cells (rods and cones) and neurons connected to a neural network for the processing of visual information (see FIG. 10). This information is sent to the brain for decoding into a visual image.

The retina depends on cells of the adjacent retinal pigment epithelium (RPE) for support of its metabolic functions. Photoreceptors in the retina, perhaps because of their huge energy requirements and highly differentiated state, are sensitive to a variety of genetic and environmental insults. The retina is thus susceptible to an array of diseases that result in visual loss or complete blindness.

Retinitis pigmentosa (RP), which results in the destruction of photoreceptor cells, the RPE, and choroid typify inherited retinal degenerations. This group of debilitating conditions affects approximately 100,000 people in the United States.

A great deal of the progress made in addressing this important clinical problem has depended on advances in research on photoreceptor cell biology, molecular biology, molecular genetics, and biochemistry over the past two decades. Animal models of hereditary retinal disease have been vital in helping unravel the specific genetic and biochemical defects that underlie abnormalities in human retinal diseases. It now seems clear that both genetic and clinical heterogeneity underlie many hereditary retinal diseases.

The leading cause of visual loss in the elderly is Age-related Macular Degeneration (AMD). The social and economic impact of this disease in the United States is increasing. The macula is a structure near the center of the retina that contains the fovea. This specialized portion of the retina is responsible for the high-resolution vision that permits activities such as reading. The loss of central vision in AMD is devastating. Degenerative changes to the macula (maculopathy) can occur at almost any time in life but are much more prevalent with advancing age. With growth in the aged population, AMD will become a more prevalent cause of blindness than both diabetic retinopathy and glaucoma combined. Laser treatment has been shown to reduce the risk of extensive macular scarring from the "wet" or neovascular form of the disease. The effects of this treatment are short-lived, however, due to recurrent choroidal neovascularization. Thus, there are presently no effective treatments in clinical use for the vast majority of AMD patients.

Other diseases of the eye, such as glaucoma, are also major public health problems in the United States. In particular, blindness from glaucoma is believed to impose significant costs annually on the U.S. Government in Social Security benefits, lost tax revenues, and healthcare expenditures.

Briefly, glaucoma is not a uniform disease but rather a heterogeneous group of disorders that share a distinct type of optic nerve damage that leads to loss of visual function. The disease is manifest as a progressive optic neuropathy that, if left untreated, leads to blindness. It is estimated that as many as 3 million Americans have glaucoma and, of these, as many as 120,000 are blind as a result. Furthermore, it is the number one cause of blindness in African-Americans. Its most prevalent form, primary open-angle glaucoma, can be insidious. This form usually begins in midlife and progresses slowly but relentlessly. If detected early, disease progression can frequently be arrested or slowed with medical and surgical treatment.

Glaucoma can involve several tissues in the front and back of the eye. Commonly, but not always, glaucoma begins with a defect in the front of the eye. Fluid in the anterior portion of the eye, the aqueous humor, forms a circulatory system that brings nutrients and supplies to various tissues. Aqueous humor enters the anterior chamber via the ciliary body epithelium (inflow), flows through the anterior segment bathing the lens, iris, and cornea, and then leaves the eye via specialized tissues known as the trabecular meshwork and Schlemm's canal to flow into the venous system. Intraocular pressure is maintained vis-à-vis a balance between fluid secretion and fluid outflow. Almost all glaucomas are associated with defects that interfere with aqueous humor outflow and, hence, lead to a rise in intraocular pressure. The consequence of this impairment in outflow and elevation in intraocular pressure is that optic nerve function is compromised. The result is a distinctive optic nerve atrophy, which clinically is characterized by excavation and cupping of the optic nerve, indicative of loss of optic nerve axons.

Primary open-angle glaucoma is, by convention, characterized by relatively high intraocular pressures believed to arise from a blockage of the outflow drainage channel or trabecular meshwork in the front of the eye. However, another form of primary open-angle glaucoma, normal-tension glaucoma, is characterized by a severe optic neuropathy in the absence of abnormally high intraocular pressure. Patients with normal-tension glaucoma have pressures within the normal range, albeit often in the high normal range. Both these forms of primary open-angle glaucoma are considered to be late-onset diseases in that, clinically, the disease first presents itself around midlife or later. However, among African-Americans, the disease may begin earlier than middle age. In contrast, juvenile open-angle glaucoma is a primary glaucoma that affects children and young adults. Clinically, this rare form of glaucoma is distinguished from primary open-angle glaucoma not only by its earlier onset but also by the very high intraocular pressure associated with this disease. Angle-closure glaucoma is a mechanical form of the disease caused by contact of the iris with the trabecular meshwork, resulting in blockage of the drainage channels that allow fluid to escape from the eye. This form of glaucoma can be treated effectively in the very early stages with laser surgery. Congenital and other developmental glaucomas in children tend to be severe and can be very challenging to treat successfully. Secondary glaucomas result from other ocular diseases that impair the outflow of aqueous humor from the eye and include pigmentary glaucoma, pseudoexfoliative glaucoma, and glaucomas resulting from trauma and inflammatory diseases. Blockage of the outflow channels by new blood vessels (neovascular glaucoma) can occur in people with retinal vascular disease, particularly diabetic retinopathy.

Primary open-angle glaucoma can be insidious. It usually begins in midlife and progresses slowly but relentlessly. If detected, disease progression can frequently be arrested or slowed with medical and surgical treatment. However, without treatment, the disease can result in absolute irreversible blindness. In many cases, even when patients have received adequate treatment (e.g., drugs to lower intraocular pressure), optic nerve degeneration and loss of vision continues relentlessly.

The present invention provides compositions and methods for treating and preventing a number of diseases of the eye, including for example, retinal diseases and degenerations such as RP and AMD, as well as other diseases such as neovascular disease. The present invention also provides other, related advantages.

SUMMARY OF THE INVENTION

Briefly stated, the present invention provides compositions and methods for treating, preventing, or, inhibiting diseases of the eye. Within one aspect of the present invention, methods are provided for treating or preventing diseases of the eye comprising the step of intraocularly administering a gene delivery vector which directs the expression of one or more neurotrophic factors, or, anti-angiogenic factors, such that the disease of the eye is treated or prevented. Within related aspects of the present invention, gene delivery vectors are provided which direct the expression of one or more neurotrophic factors such as FGF, as well as gene therapy vectors which direct the expression of one or more anti-angiogenic factors. Within certain embodiments of the invention, a viral promoter (e.g., CMV) or an inducible promoter (e.g., tet) is utilized to drive the expression of the neurotrophic factor.

Representative examples of gene delivery vectors suitable for use within the present invention may be generated from viruses such as retroviruses (e.g., FIV or HIV), herpesviruses, adenoviruses, adeno-associated viruses, and alphaviruses, or from non-viral vectors.

Utilizing the methods and gene delivery vectors provided herein a wide variety of diseases of the eye may be readily treated or prevented, including for example, glaucoma, macular degeneration, diabetic retinopathies, inherited retinal degeneration such as retinitis pigmentosa, retinal detachment or injury and retinopathies (whether inherited, induced by surgery, trauma, a toxic compound or agent, or, photically). Similarly, a wide variety of neurotrophic factors may be utilized (either alone or in combination) within the context of the present invention, including for example, NGF, BDNF, CNTF, NT-3, NT-4, FGF-2, FGF-5, FGF-18, FGF-20 and FGF-21.

Within certain embodiments of the invention, it is preferred that the gene delivery vector be utilized to deliver and express an anti-angiogenic factor for the treatment, prevention, or, inhibition of diabetic retinopathy, wet AMD, and other neovascular diseases of the eye (e.g., ROP). Within other embodiments it is desirable that the gene delivery vector be utilized to deliver and express a neurotrophic growth factor to treat, prevent, or, inhibit diseases of the eye, such as, for example, glaucoma, retinitis pigmentosa, and dry AMD. Within yet other embodiments, it may be desirable to utilize either a gene delivery vector which expresses both an anti-angiogenic molecule and a neurotrophic growth factor, or two separate vectors which independently express such factors, in the treatment, prevention, or inhibition of an eye disease (e.g., for diabetic retinopathy).

Within further embodiments of the invention, the above-mentioned methods utilizing gene delivery vectors may be administered along with other methods or therapeutic regimens, including for example, photodynamic therapy (e.g., for wet AMD), laser photocoagulation (e.g., for diabetic retinopathy and wet AMD), and intraocular pressure reducing drugs (e.g., for glaucoma).

Also provided by the present invention are isolated nucleic acid molecules comprising the sequence of FIG. 2, vectors which contain, and/or express this sequence, and host cells which contain such vectors.

Within further aspects of the present invention gene delivery vectors are provided which direct the expression of a neurotrophic factor, or, an anti-angiogenic factor. As noted above, representative examples of neurotrophic factors include NGF, BDNF, CNTF, NT-3, NT4, FGF-2, FGF-5, FGF-18, FGF-20 and FGF-21. Representative examples of anti-angiogenic factors include soluble Flt-l, soluble Tie-2 receptor, and PEDF. Representative examples of suitable gene delivery vectors include adenovirus, retroviruses (e.g., HIV or FIV-based vectors), alphaviruses, AAV vectors, and naked DNA vectors.

Within yet other aspects of the invention non-human animal models of neovascular diseases of the eye are provided, comprising an animal having an angiogenic (i.e., pro-angiogenic) transgene in the eye. Within various embodiments, the neovascularization may be retinal or choroidal neovascularization. Within other embodiments, the animal may be a mouse or rat. As noted herein, a wide variety of angiogenic transgenes may be utilized to generate the non-human animal model, including for example, angiogenic transgenes that encode VEGF and/or an angiopoietin such as angiopoietin-1.

Also provided are methods of making such non-human animal models comprising the general steps of administering to a non-human animal a gene delivery vector which directs the expression of an angiogenic transgene. As noted above, a wide variety of gene delivery vectors (e.g., rAV and rAAV) can be utilized, as well as nucleic acid molecules which encode the angiogenic transgene (e.g., nucleic acid molecules encoding VEGF or angiopoietin). Within certain embodiments, the gene delivery vector can be administered subretinally or intravitreally. Within further embodiments the animal model can be utilized as a model for Age-related Macular Degeneration (AMD), diabetic retinopathy, or, retinopathy of prematurity (ROP).

Also provided are methods for determining the ability of an anti-angiogenic factor to inhibit neovascularization of the eye, comprising the general steps of (a) administering to an animal model as described herein an anti-angiogenic factor, and (b) determining the ability of the anti-angiogenic factor to inhibit neovascularization of the eye. As noted herein, the anti-angiogenic factor may be administered by a variety of routes, including for example, topically, subretinally, or, intravitreally. Further, the animal model may be utilized to test the efficacy of drugs, compounds, or other factors or agents for a wide variety of eye-related neovascular diseases (including AMD and ROP).

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIGS. 2A and 2B are the nucleic acid sequence of pKm201bFGF-2 (SEQ ID. No. 1).

FIGS. 15A, 15B and 15C are photographs of FGF-2 expressing cells stained with an anti-FGF-2 antibody.

FIGS. 22A and 22B are the nucleotide sequence of pD10-VEGFuc (SEQ ID NO: 2).

FIG. 23 is a bar graph which shows pD10-VEGFuC rAAV virus infection of 293 cells.

FIGS. 28A and 28B provide the nucleotide sequence of pD10sFlt-1 (SEQ ID NO: 3).

FIG. 29 is the nucleotide sequence of FGF-20 (SEQ ID NO: 4) and the amino acid sequence of FGF-20 (SEQ ID NO: 5).

FIG. 30 is the nucleotide sequence of FGF-21 (SEQ ID NO: 6) and the amino acid sequence of FGF-21 (SEQ ID NO: 7).

FIGS. 32A and 32B are the nucleotide sequence of pD10K-FGF-2Sc (SEQ ID NO: 8).

FIGS. 35A and 35B are photographic images showing retinal blood vessels from a live animal, before sacrifice.

FIGS. 36A, 36B, 36C, and 36D are a series of images showing epoxy sections of an eye at various distances from an AAV-VEGF injection site.

FIGS. 37A, 37B, 37C, and 37D are photographs which show lectin/BrdU double-staining of the rat retina.

FIGS. 38A and 38B are bar graphs which show sFit-1 and PEDF rescue of ERGs.

FIG. 39 is a graph which shows the ERG of a test and control eye of sFlt-1 treated rats.

DETAILED DESCRIPTION OF THE INVENTION

DEFINITIONS

Figure 1:
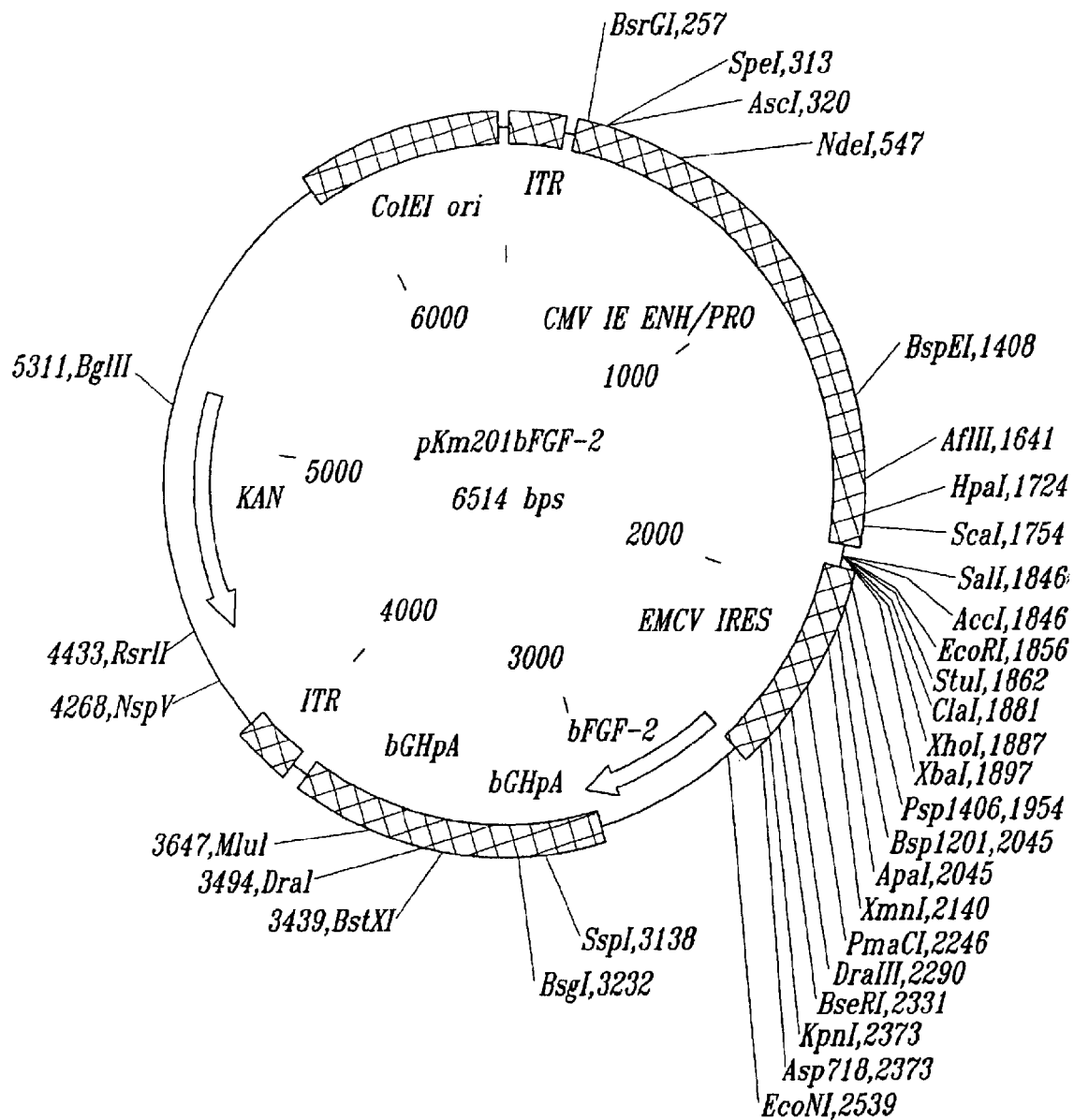
FIG. 1 is a schematic illustration of pKm201bFGF-2.

Prior to setting forth the invention, it may be helpful to an understanding thereof to first set forth definitions of certain terms that will be used hereinafter. "Gene delivery vector" refers to a construct which is capable of delivering, and, within preferred embodiments expressing, one or more gene(s) or sequence(s) of interest in a host cell. Representative examples of such vectors include viral vectors, nucleic acid expression vectors, naked DNA, and certain eukaryotic cells (e.g., producer cells).

"Recombinant adeno-associated virus vector" or "rAAV vector" refers to a gene delivery vector based upon an adeno-associated virus. The rAAV vectors, should contain 5' and 3' adeno-associated virus inverted terminal repeats (ITRs), and a transgene or gene of interest operatively linked to sequences which regulate its expression in a target cell. Within certain embodiments, the transgene may be operably linked to a heterologous promoter (such as CMV), or, an inducible promoter such as (tet). In addition, the rAAV vector may have a polyadenylation sequence.

"Neurotrophic Factor" or "NT" refers to proteins which are responsible for the development and maintenance of the nervous system. Representative examples of neurotrophic factors include NGF, BDNF, CNTF, NT-3, NT4, and Fibroblast Growth Factors.

"Fibroblast Growth Factor" or "FGF" refers to a family of related proteins, the first of which was isolated from the pituitary gland (see Gospodarowicz, D., *Nature*, 249:123–127, 1974). From this original FGF (designated basic FGF) a family of related proteins, protein muteins, and protein analogs have been identified (see, e.g., U.S. Pat. Nos. 4,444,760, 5,155,214, 5,371,206, 5,464,774, 5,464,943, 5,604,293, 5,731,170, 5,750,365, 5,851,990, 5,852,177, 5,859,208, and 5,872,226), all of which are generally referred to as Fibroblast Growth Factors within the context of the present invention.

"Anti-angiogenic Factor" refers to a factor or molecule which is able to inhibit the proliferation of vascular growth. A variety of assays may be utilized to assess the anti-angiogenic activity of a given molecule, including for example, the assay provided in Example 15, which measures HMVEC (human dermal microvascular endothelial cell) proliferation. Representative examples of anti-angiogenic factors include for example, Angiostatin, 1,25-Di-hydroxyvitamn $D_3$, Endostatin, IGF-1 receptor antagonists, Interferons alpha, beta and gamma, Interferon gamma-inducible protein IP-10, Interleukin 1 alpha and beta, Interleukin 12, 2-Methoxyestradiol, PEDF, Platelet factor 4, Prolactin (16kd fragment), Protamin, Retinoic acid, Thrombospondin-1 and 2, Tissue inhibitor of metalloproteinase-1 and -2, Transforming growth factor beta, anti-VEGF antibodies (which should be understood to include fragments of antibodies such as a single chain antibodies, Fab fragements, or, CDR regions), soluble Tie-2 receptor, soluble Tie-2 receptor, soluble Flt-1 and Tumor necrosis factor-alpha.

"Diseases of the Eye" refers to a broad class of diseases wherein the functioning of the eye is affected due to damage or degeneration of the photoreceptors; ganglia or optic nerve; or neovascularization. Representative examples of such diseases include macular degeneration, diabetic retinopathies, inherited retinal degeneration such as retinitis pigmentosa, glaucoma, retinal detachment or injury and retinopathies (whether inherited, induced by surgery, trauma, a toxic compound or agent, or, photically).

As noted above, the present invention provides compositions and methods for treating, preventing, or, inhibiting diseases of the eye, comprising the general step of administering intraocularly a recombinant adeno-associated viral vector which directs the expression of one or more neurotrophic factors, such that the disease of the eye is treated or prevented. In order to further an understanding of the invention, a more detailed discussion is provided below regarding (A) gene delivery vectors; (B) Neurotrophic Factors; (C) Anti-angiogenic factors; and (D) methods of administering the rAAVs in the treatment or prevention of diseases of the eye.

A. Gene Delivery Vectors

1. Construction of Retroviral Gene Delivery Vectors

Within one aspect of the present invention, retroviral gene delivery vectors are provided which are constructed to carry or express a selected gene(s) or sequence(s) of interest. Briefly, retroviral gene delivery vectors of the present invention may be readily constructed from a wide variety of retroviruses, including for example, B, and D type retroviruses as well as spumaviruses and lentiviruses (see RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques.

Any of the above retroviruses may be readily utilized in order to assemble or construct retroviral gene delivery vectors given the disclosure provided herein, and standard recombinant techniques (e.g., Sambrook et al., *Molecular Cloning: A Laboratory Manual*, 2d ed., Cold Spring Harbor Laboratory Press, 1989; Kunkel, *PNAS* 82:488, 1985). In addition, within certain embodiments of the invention, portions of the retroviral gene delivery vectors may be derived from different retroviruses. For example, within one embodiment of the invention, retrovirus LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Within one aspect of the present invention, retrovector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences.

Other retroviral gene delivery vectors may likewise be utilized within the context of the present invention, including for example EP 0,415,731; WO 90/07936; WO 91/0285, WO 9403622; WO 9325698; WO 9325234; U.S. Pat. No. 5,219,740; WO 9311230; WO 9310218; Vile and Hart, Cancer Res. 53:3860–3864, 1993; Vile and Hart, Cancer Res. 53:962–967, 1993; Ram et al., Cancer Res. 53:83–88, 1993; Takamniya et al., J. Neurosci. Res. 33:493–503, 1992; Baba et al., J. Neurosurg. 79:729–735, 1993 (U.S. Pat. No. 4,777,127, GB 2,200,651, EP 0,345,242 and WO91/02805).

Packaging cell lines suitable for use with the above described retrovector constructs may be readily prepared (see U.S. Ser. No. 08/240,030, filed May 9, 1994; see also U.S. Ser. No. 07/800,921, filed Nov. 27, 1991), and utilized to create producer cell lines (also termed vector cell lines or "VCLs") for the production of recombinant vector particles.

2. Recombinant Adeno-Associated Virus Vectors

As noted above, a variety of rAAV vectors may be utilized to direct the expression of one or more desired neurotrophic factors. Briefly, the rAAV should be comprised of, in order, a 5' adeno-associated virus inverted terminal repeat, a transgene or gene of interest operatively linked to a sequence which regulates its expression in a target cell, and a 3' adeno-associated virus inverted terminal repeat. In addition, the rAAV vector may preferably have a polyadenylation sequence.

Generally, rAAV vectors should have one copy of the AAV ITR at each end of the transgene or gene of interest, in order to allow replication, packaging, and efficient integration into cell chromosomes. The ITR consists of nucleotides 1 to 145 at the 5' end of the AAV DNA genome, and nucleotides 4681 to 4536 (i.e., the same sequence) at the 3' end of the AAV DNA genome. Preferably, the rAAV vector may also include at least 10 nucleotides following the end of the ITR (ie., a portion of the "D region").

Within preferred embodiments of the invention, the transgene sequence will be of about 2 to 5 kb in length (or alternatively, the transgene may additionally contain a "stuffer" or "filler" sequence to bring the total size of the nucleic acid sequence between the two ITRs to between 2 and 5 kb). Alternatively, the transgene may be composed of same heterologous sequence several times (e.g., two nucleic acid molecules which encode FGF-2 separated by a ribosome readthrough, or alternatively, by an Internal Ribosome Entry Site or "IRES"), or several different heterologous sequences (e.g., FGF-2 and FGF-5, separated by a ribosome readthrough or an IRES).

Recombinant AVV vectors of the present invention may be generated from a variety of adeno-associated viruses, including for example, serotypes 1 through 6. For example, ITRs from any AAV serotype are expected to have similar structures and functions with regard to replication, integration, excision and transcriptional mechanisms.

Within certain embodiments of the invention, expression of the transgene may be accomplished by a separate promoter (e.g., a viral promoter). Representative examples of suitable promoters in this regard include a CMV promoter, RSV promoter, SV40 promoter, or MoMLV promoter. Other promoters that may similarly be utilized within the context of the present invention include cell or tissue specific promoters (e.g., a rod, cone, or ganglia derived promoter), or inducible promoters. Representative examples of suitable inducible promoters include tetracycline-response promoters ("Tet", see, e.g., Gossen and Bujard, Proc. Natl. Acad. Sci. USA. 89:5547–5551, 1992; Gossen et al., Science 268, 1766–1769, 1995; Baron et al., Nucl. Acids Res. 25:2723–2729, 1997; Blau and Rossi, Proc. Natl. Acad. Sci. USA. 96:797–799, 1999; Bohl et al., Blood 92:1512–1517, 1998; and Haberman et al., Gene Therapy 5:1604–1611, 1998), the ecdysone system (see e.g., No et al., Proc. Natl. Acad. Sci. USA. 93:3346–3351, 1996), and other regulated promoters or promoter systems (see, e.g., Rivera et al., Nat. Med. 2:1028–1032, 1996;).

The rAAV vector may also contain additional sequences, for example from an adenovirus, which assist in effecting a desired function for the vector. Such sequences include, for example, those which assist in packaging the rAAV vector in adenovirus-associated virus particles.

Packaging cell lines suitable for producing adeno-associated viral vectors may be readily accomplished given readily available techniques (see e.g., U.S. Pat. No. 5,872,005).

Particularly preferred methods for constructing and packaging rAAV vectors are described in more detail below in Examples 1, 2, 3, and 4.

3. Alphavirus Delivery Vectors

The present invention also provides a variety of Alphavirus vectors which may function as gene delivery vectors. For example, the Sindbis virus is the prototype member of the alphavirus genus of the togavirus family. The unsegmented genomic RNA (49S RNA) of Sindbis virus is approximately 11,703 nucleotides in length, contains a 5' cap and a 3' poly-adenylated tail, and displays positive polarity. Infectious enveloped Sindbis virus is produced by assembly of the viral nucleocapsid proteins onto the viral genomic RNA in the cytoplasm and budding through the cell membrane embedded with viral encoded glycoproteins. Entry of virus into cells is by endocytosis through clatharin coated pits, fusion of the viral membrane with the endosome, release of the nucleocapsid, and uncoating of the viral genome. During viral replication the genomic 49S RNA serves as template for synthesis of the complementary negative strand. This negative strand in turn serves as template for genomic RNA and an internally initiated 26S subgenomic RNA. The Sindbis viral nonstructural proteins are translated from the genomic RNA while structural proteins are translated from the subgenomic 26S RNA. All viral genes are expressed as a polyprotein and processed into individual proteins by post translational proteolytic cleavage. The packaging sequence resides within the nonstructural coding region, therefore only the genomic 49S RNA is packaged into virions.

Several different Sindbis vector systems may be constructed and utilized within the present invention. Representative examples of such systems include those described within U.S. Pat. Nos. 5,091,309 and 5,217,879, and PCT Publication No. WO 95/07994.

4. Other Viral Gene Delivery Vectors

In addition to retroviral vectors and alphavirus vectors, numerous other viral vectors systems may also be utilized as a gene delivery vector. Representative examples of such gene delivery vectors include viruses such as pox viruses, such as canary pox virus or vaccinia virus (Fisher-Hoch et al., PNAS 86:317–321, 1989; Flexner et al., Ann. N.Y. Acad.

Sci. 569:86–103. 1989; Flexner et al., *Vaccine* 8:17–21, 1990; U.S. Pat. Nos. 4,603,112, 4,769,330 and 5,017,487; WO 89/01973); SV40 (Mulligan et al., *Nature* 277:108–114, 1979); influenza virus (Luytjes et al., *Cell* 59:1107–1113, 1989; McMicheal et al., *N. Eng. J. Med.* 309:13–17, 1983; and Yap et al., *Nature* 273:238–239, 1978); herpes (Kit, *Adv. Exp. Med. Biol.* 215:219–236, 1989; U.S. Pat. No. 5,288,641); HIV (Poznansky, *J. Virol.* 65:532–536, 1991); measles (EP 0 440,219); Semliki Forest Virus, and coronavirus, as well as other viral systems (e.g., EP 0,440,219; WO 92/06693; U.S. Pat. No. 5,166,057). In addition, viral carriers may be homologous, non-pathogenic(defective), replication competent virus (e.g., Overbaugh et al., *Science* 239:906–910,1988), and nevertheless induce cellular immune responses, including CTL.

5. Non-viral Gene Delivery Vectors

In addition to the above viral-based vectors, numerous non-viral gene delivery vectors may likewise be utilized within the context of the present invention. Representative examples of such gene delivery vectors include direct delivery of nucleic acid expression vectors, naked DNA alone (WO 90/11092), polycation condensed DNA linked or unlinked to killed adenovirus (Curiel et al., *Hum. Gene Ther.* 3:147–154, 1992), DNA ligand linked to a ligand with or without one of the high affinity pairs described above (Wu et al., *J. of Biol. Chem* 264:16985–16987, 1989), nucleic acid containing liposomes (e.g., WO 95/24929 and WO 95/12387) and certain eukaryotic cells (e.g., producer cells—see U.S. Ser. No. 08/240,030, filed May 9, 1994, and U.S. Ser. No. 07/800,921).

B. Neurotrophic Factors

As noted above, the term neurotrophic factor refers to proteins which are responsible for the development and maintenance of the nervous system. Representative examples of neurotrophic factors include NGF, BDNF, CNTF, NT-3, NT4, and Fibroblast Growth Factors.

Fibroblast Growth Factor refers to a family of related proteins, the first of which was isolated from the pituitary gland (see Gospodarowicz, D., *Nature,* 249:123–127, 1974). From this original FGF (designated basic FGF) a family of related proteins, protein muteins, and protein analogs have been identified (see, e.g., U.S. Pat. Nos. 4,444,760, 5,155,214, 5,371,206, 5,464,774, 5,464,943, 5,604,293, 5,731,170, 5,750,365, 5,851,990, 5,852,177, 5,859,208, and 5,872,226; see generally Baird and Gospodarowicz, D. *Ann N.Y. Acad. Sci.* 638:1, 1991. The first two members of the family to be identified were acidic fibroblast growth factor (aFGF/FGF-1) and basic fibroblast growth factor (bFGF/FGF-2). Additional members of the FGF family include: i-nt-2/FGF-3, (Smith et al., *EMBO J.* 7: 1013, 1988); FGF-4 (Delli-Bovi et al., Cell 50: 729, 1987); FGF-6 (Marics et al., *Oncogene* 4: 335 (1989); keratinocyte growth factor/FGF-7, (Finch et al., *Science* 245: 752, 1989); FGF-8 (Tanaka et al., *Proc. Natl. Acad Sci. USA* 89: 8928, 1992); and FGF-9 (Miyamoto et al., *Mol. Cell Biol.* 13: 4251, 1993).

FGF-5 was originally isolated as an oncogene. See Goldfarb et al. U.S. Pat. Nos. 5,155,217 and 5,238,916, Zhan et al. "Human Oncogene Detected by a Defined Medium Culture Assay" (*Oncogene* 1:369–376, 1987), Zhan et al. "The Human FGF-5 Oncogene Encodes a Novel Protein Related to Fibroblastic Growth Factors" (*Molecular and Cellular Biology* 8:3487–3495, 1988), and Bates et al. "Biosynthesis of Human Fibroblast Growth Factor 5": (*Molecular and Cellular Biology* 11:1840–1845, 1991).

Other FGFs include those disclosed in U.S. Pat. Nos. 4,444,760, 5,155,214, 5,371,206, 5,464,774, 5,464,943, 5,604,293, 5,731,170, 5,750,365, 5,851,990, 5 5,852,177, 5,859,208, and 5,872,226. 5,852,177, and 5,872,226, as well as FGF-20 (U.S. Provisional Application No. 60/161,162) and FGF-21 (U.S. Provisional Application No. 60/166,540).

C. Anti-Angiogenic Factors

A wide variety of anti-angiogenic factors may also be expressed from the gene delivery vectors of the present invention, including for example, Angiostatin (O'Reilly et al., *Cell* 79:315–328, 1994; O'Reilly et al., *Nat. Med.* 2:689–92, 1996; Sim et al., *Cancer Res.* 57:1329–34, 1997), 1,25-Di-hydroxy-vitamn $D_3$ (Shibuya et al., *Oncogene* 5:519–24, 1990; Oikawa et al., *Eur. J. Pharmacol.* 178:247–50, 1990; and 182:616, 1990), Endostatin (O'Reilly et al., *Cell* 88:277–85, 1997), Interferons alpha and beta (Sidky et al., *Cancer Res.* 47:5155–61, 1987; Singh et al., *Proc. Natl. Acad. Sci. USA* 92:4562–6, 1995), Interferon gamma (Friesel et al., *J. Cell. Biol.* 104:689–96, 1987), IGF-1 receptor antagonists, Interferon gamma-inducible protein IP-10 (Arenberg et al., *J. Exp. Med.* 1996;184:981–92; Strieter et al., J. Leukoc. Biol. 1995;57:752–62; Angiolillo et al., *J. Exp. Med.* 182:155–62, 1995), Interleukin 1alpha and beta (Cozzolino et al., *Proc. Natl. Acad. Sci. USA* 87:6487–91, 1990), Interleukin 12 (Kerbel and Hawley, *J. Natl Cancer Inst.* 87:557–9, 1995; Majewski et al., *J. Invest. Dermatol* 106:1114–8, 1996; Voest et al., *J. Natl Cancer Inst.* 87:581–6, 1995), 2-Methoxyestradiol (Fotsis et al., *Nature* 368:237–9, 1994), Platelet factor 4 (Taylor and Folkman, *Nature* 297:307–12, 1982; Gengrinovitch et al., *J. Biol. Chem* 270:15059–65, 1995), Prolactin (16 kd fragment) (Clapp et al., *Endocrinology* 133:1292–9, 1993; Ferrara, *Endocrinology* 129:896–900, 1991), Protamin, Retinoic acid (Lingen et al., *Lab. Invest* 74:476–83, 1996), Thrombospondin-1 and 2 (Lawler, *Blood,* 67:1197–209, 1986; Raugi and Lovett, *Am. J. Pathol* 129:364–72, 1987; Volpert et al., *Biochem. Biophys. Res. Commun* 217:326–32, 1995), Tissue inhibitor of metalloproteinase-1 and -2 (Moses and Langer, *J. Cell Biochem* 47:230–5, 1991; Ray and Stetler-Stevenson, *Eur. Respir. J.* 7:2062–72, 1994), Transforming growth factor beta (RayChaudhury, *J. Cell. Biochem* 47:224–9, 1991; Roberts et al., *Proc. Natl Acad. Sci USA* 83:4167–71, 1986), and Tumor necrosis factor—alpha (Frater-Schroeder et al., *Proc. Natl. Acad. Sci. USA* 84:5277–81, 1987; Leibovich et al., *Nature* 329:630–2, 1987).

Other anti-angiogenic factors that can be utilized within the context of the present invention include VEGF antagonists such as soluble Fit-1 (Kendall and Thomas, *PNAS* 90: 10705, 1993), pigment epithelium-derived factor or "PEDF" (Dawson et al., Science 285:245, 1999), and Ang-1 antagonists such as soluble Tie-2 receptor (Thurston et al., *Science* 286:2511, 1999; see also, generally Aiello et al., *PNAS* 92:10457, 1995; Robinson et al., *PNAS* 93:4851, 1996; Seo et al., *Am. J. Pathol.* 154:1743, 1999).

The ability of a given molecule to be "anti-angiogenic" can be readily assessed utilizing a variety of assays, including for example, the HMVEC assay provided in Example 15.

D. Method for Treating and/or Preventing Diseases of the Eye and Pharmaceutical Compositions As noted above, the present invention provides methods which generally comprise the step of intraocularly administering a gene delivery vector which directs the expression of one or more neurotrophic factor to the eye, or an anti-angiogenic factor to the eye in order to treat, prevent, or inhibit the progression of an eye disease. As utilized herein, it should be understood that the terms "treated, prevented, or, inhibited" refers to the alteration of a disease course or progress in a statistically significant manner. Determination of whether a disease course has been altered may be readily assessed in a variety of model systems, discussed in more detail below, which analyze the ability of a gene delivery vector to delay, prevent or rescue photoreceptors, as well as other retinal cells, from cell death.

1. Diseases of the Eye

A wide variety of diseases of the eye may be treated given the teachings provided herein. For example, within one embodiment of the invention gene delivery vectors are administered to a patient intraocularly in order to treat or prevent macular degeneration. Briefly, the leading cause of visual loss in the elderly is macular degeneration (MD), which has an increasingly important social and economic impact in the United States. As the size of the elderly population increases in this country, age related macular degeneration (AMD) will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with MD.

Within another embodiment, gene delivery vectors can be administered to a patient intraocularly in order to treat or prevent an inherited retinal degeneration. One of the most common inherited retinal degenerations is retinitis pigmentosa (RP), which results in the destruction of photoreceptor cells, and the RPE. Other inherited conditions include Bardet-Biedl syndrome (autosomal recessive); Congenital arnaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive). This group of debilitating conditions affects approximately 100,000 people in the United States alone.

As noted above, within other aspects of the invention, gene delivery vectors which direct the expression of a neurotrophic growth factor can be administered to a patient intraocularly in order to treat or prevent glaucoma. Briefly, glaucoma is not a uniform disease but rather a heterogeneous group of disorders that share a distinct type of optic nerve damage that leads to loss of visual function. The disease is manifest as a progressive optic neuropathy that, if left untreated leads to blindness. It is estimated that as many as 3 million Americans have glaucoma and, of these, as many as 120,000 are blind as a result. Furthermore, it is the number one cause of blindness in African-Americans. Its most prevalent form, primary open-angle glaucoma, can be insidious. This form usually begins in midlife and progresses slowly but relentlessly. If detected early, disease progression can frequently be arrested or slowed with medical and surgical treatment. Representative factors that may be expressed from the vectors of the present invention to treat glaucoma include neurotrophic growth factors such as FGF-2, 5, 18, 20, and, 21.

Within yet other embodiments gene delivery vectors can be administered to a patient intraocularly in order to treat or prevent injuries to the retina, including retinal detachment, photic retinopathies, surgery-induced retinopathies, toxic retinopathies, retinopathies due to trauma or penetrating lesions of the eye.

As noted above, the present invention also provides methods of treating, preventing, or, inhibiting neovascular disease of the eye, comprising the step of administering to a patient a gene delivery vector which directs the expression of an anti-angiogenic factor. Representative examples of neovascular diseases include diabetic retinopathy, AMD (wet form), and retinopathy of prematurity. Briefly, choroidal neovascularization is a hallmark of exudative or wet Age-related Macular Degeneration (AMD), the leading cause of blindness in the elderly population. Retinal neovascularization occurs in diseases such as diabetic retinapathy and retinopathy of prematurity (ROP), the most common cause of blindness in the young.

Particularly preferred vectors for the treatment, prevention, or, inhibition of neovascular diseases of the eye direct the expression of an anti-angiogenic factor such as, for example, soluble tie-2 receptor or soluble Flt-1.

2. Animal Models

In order to assess the ability of a selected gene therapy vector to be effective for treating diseases of the eye which involve neovascularization, a novel model for neovascularization (either choroidal or subretinal) can be generated by subretinal injection of a recombinant virus (e.g., rAV or rAAV) containing an angiogenic transgene such as VEGF and/or angiopoietin. Within certain embodiments, an angiogenic transgene such as angiopoietin-1 can be used in combination with another factor such as VEGF, in order to generate neovascularization. The extent and duration of neovascularization induced by the gene delivery vectors containing an angiogenic transgene such as VEGF can be determined using fundus photography, fluorescein angiography and histochemistry.

To assess the ability of anti-angiogenic molecules to prevent neovascularization in the model described above, a D10-sFlt-1 rAAV (or other gene delivery vector which directs the expression of an anti-angiogenic factor) is intraocularly injected, either by subretinal or intravitreal routes of injection. Generally, subretinal injection of the gene delivery vector may be utilized to achieve delivery to both the choroidal and inner retinal vasculature. Intravitreal injection can be utilized to infect Muller cells and retinal ganglion cells (RGCs), which deliver anti-angiogenic protein to the retinal vasculature. Muller cells span the retina and would secrete the therapeutic protein into the subretinal space.

Such injections may be accomplished either prior to, simultaneous with, or subsequent to administration of an angiogenic factor or gene delivery vector which expresses an angiogenic factor. After an appropriate time interval, inhibition of neovascularization can be determined using fundus photography, fluorescein angiography and/or histochemistry.

While there are many animal models of retinal neovascularization such as oxygen-induced ischemic retinopathy (Aiello et al., PNAS 93: 4881, 1996.) and the VEGF transgenic mouse (Okamoto et al., Am. J. Pathol. 151: 281, 1997), there are fewer models of choroidal neovascularization (e.g., laser photocoagulation as described by Murata et al., IOVS 39: 2474, 1998). Subretinal neovascularization from the retinal rather than choroidal blood supply is also observed in VEGF transgenic animals (Okamoto et al., Am. J. Pathol. 151: 281, 1997). Hypoxic stimulation of VEGF expression is known to correlate with neovascularization in human ocular disease.

The pathologic hallmark of glaucomatous optic neuropathy is the selective death of retinal ganglion cells (RGCs) (Nickells, R. W., *J. Glaucoma* 5:345–356. 1996; Levin, L. A.

and Louhab, A., *Arch. Ophihalmol.* 114:488–491, 1996.; Kerrigan, L. A., Zack, D. J., Quigley, H. A., Smith, S. D. and Pease, M. E., *Arch. Ophihalmol.* 115:1031–1035, 1997). Recent studies indicate that RGCs die with characteristics of apoptosis after injury to the axons of adult RGCs such as axotomy of the optic nerve (ON), and in glaucoma and anterior ischemic optic neuropathy in humans (Nickells, 1996). Thus, damage to the optic nerve by axotomy is used by many researchers as a model for selective apoptotic cell death of adult RGCs.

The loss of-RGCs caused by ON transection in adult mammals varies from 50% to more than 90% depending on the techniques used to identify RGCs, the proximity of the lesion to the eye, and the age and species of the animal. For example, in a study in adult rats, in which retrogradely transported tracers were used to distinguish RGCs from displaced amacrine cells (Villegas-Pérez, M. P., Vidal-Sanz, M., Bray, G. M. and Aguayo, A. J., *J. Neurosci.* 8:265–280, 1988). ON transection near the eye (0.5–1 mm) leads to the loss of more than 90% of the RGCs by 2 weeks. In contrast, in adult animals in which the ON was cut nearly 10 mm from the eye, 54% of RGCs survived by 3 months (Richardson, P. M., Issa, V. M. K. and Shemie, S., *J. Neurocytol.* 11:949–966, 1982.).

Briefly, the posterior pole of the left eye and the origin of the optic nerve (ON) are exposed through a superior temporal intraorbital approach. A longitudinal excision of the ON dural sheath is performed. The ON is then gently separated from the dorsal aspect of this sheath and completely transected within the orbit, within 1 mm of the optic disc. Care is taken to avoid damage to the ophthalmic artery, which is located on the inferomedial dural sheath of the ON.

RGC survival and death following gene delivery can also be examined using two alternative models of ON injury: 1) ON crush; and (2) increased intraocular pressure. In the first model the ON is exposed, and then clamped at a distance of about one millimeter from the posterior pole using a pair of calibrated forceps as previously described (Li et al., *Invest. Ophihalmol. Vis. Sci.* 40:1004, 1999). In the second model, chronic moderately elevated intraocular pressure can be produced unilaterally by cauterization of three episcieral vessels as described by Neufeld et al. in *PNAS* 17:9944, 1999).

A variety of animal models can be utilized for photoreceptor degeneration, including the RCS rat model, P23H transgenic rat model, the rd mouse, and the S334ter transgenic rat model.

Briefly, in the S334ter transgenic rat model, a mutation occurs resulting in the truncation of the C-terminal 15 amino acid residues of rhodopsin (a seven-transmembrane protein found in photoreceptor outer segments, which acts as a photopigment). The S334ter mutation is similar to rhodopsin mutations found in a subset of patients with retinitis pigmentosa (RP). RP is a heterogeneous group of inherited retinal disorders in which individuals experience varying rates of vision loss due to photoreceptor degeneration. IN many RP patients, photoreceptor cell death progresses to blindness. Transgenic S334ter rats are born with normal number of photoreceptors. The mutant rhodopsin gene begins expression at postnatal day 5 in the rat, and photoreceptor cell death begins at postnatal day 10–15. In transgenic line S334ter-3 , approximately 70% of the outer nuclear layer has degenerated by day 60 in the absence of any therapeutic intervention. The retinal degeneration in this model is consistent from animal to animal and follows a predictable and reproducible rate. This provides an assay for therapeutic effect by morphological examination of the thickness of the photoreceptor nuclear layer and comparison of the treated eye to the untreated (contralateral) eye in the same individual animal.

S334ter rats are utilized as a model for RP as follows. Briefly, S334ter transgenic rats are euthanized by overdose of carbon dioxide inhalation and immediately perfused intracardially with a mixture of mixed aldehydes (2% formaldehyde and 2.5 % glutaraldehyde). Eyes are removed and embedded in epoxy resin, and 1 $\mu$m thick histological sections are made along the vertical meridian. Tissue sections are aligned so that the ROS and Miller cell processes crossing the inner plexiform layer are continuous throughout the plane of section to assure that the sections are not oblique, and the thickness of the ONL and lengths of RIS and ROS are measured. These retinal thickness measurements are plotted and establish the baseline retinal degeneration rates for the animal model. The assessment of retinal thickness is as follows: briefly, 54 measurements of each layer or structure were made at set points around the entire retinal section. These data were either averaged to provide a single value for the retina, or plotted as a distribution of thickness or length across the retina. The greatest 3 contiguous values for ONL thickness in each retina is also compared in order to determine if any region of retina (e.g., nearest the injection site) showed proportionally greater rescue; although most of these values were slightly greater than the overall mean of all 54 values, they were no different from control values than the overall mean. Thus, the overall mean was used in the data cited, since it was based on a much larger number of measurements.

One particularly preferred line of transgenic rats, TgN (s334ter) linc 4 (abbreviated s334ter 4) can be utilized for in vivo experiments. Briefly, in this rat model expression of the mutated opsin transgene begins at postnatal day P5 in these rats, leading to a gradual death of photoreceptor cells. These rats develop an anatomically normal retina up to P15, with the exception of a slightly increased number of pyknotic photoreceptor nuclei in the outer nuclear layer (ONL) than in non-transgenic control rats. In this animal model , the rate of photoreceptor cell death is approximately linear until P60, resulting in loss of 40–60% of the photoreceptors. After P60, the rate of cell loss decreases, until by one year the retinas have less than a single row of photoreceptor nuclei remaining.

3. Methods of Administration

Gene delivery vectors of the present invention may be administered intraocularly to a variety of locations depending on the type of disease to be treated, prevented, or, inhibited, and the extent of disease. Examples of suitable locations include the retina (e.g., for retinal diseases), the vitreous, or other locations in or adjacent to the eye.

Briefly, the human retina is organized in a fairly exact mosaic. In the fovea, he mosaic is a hexagonal packing of cones. Outside the fovea, the rods break up the close hexagonal packing of the cones but still allow an organized architecture with cones rather evenly spaced surrounded by rings of rods. Thus in terms of densities of the different photoreceptor populations in the human retina, it is clear that the cone density is highest in the foveal pit and falls rapidly outside the fovea to a fairly even density into the peripheral retina (see Osterberg, G. (1935) Topography of the layer of rods and cones in the human retina. *Acta Ophthal.* (suppl.) 6, 1–103; see also Curcio, C. A., Sloan, K. R., Packer, O., Hendrickson, A. E. and Kalina, R. E. (1987) Distribution of cones in human and monkey retina: individual variability and radial asymmetry. *Science* 236, 579–582).

Access to desired portions of the retina, or to other parts of the eye may be readily accomplished by one of skill in the art (see, generally Medical and Surgical Retina: Advances, Controversies, and Management, Hilet Lewis, Stephen J. Ryan, Eds., medical illustrator, Timothy C. Hengst. St. Louis: Mosby, c1994. xix, 534; see also Retina,Stephen J. Ryan, editor in chief,. 2nd ed., St. Louis, Mo.: Mosby, c1994. 3 v. (xxix. 2559 p.).

The amount of the specific viral vector applied to the retina is uniformly quite small as the eye is a relatively contained structure and the agent is injected directly into it. The amount of vector that needs to be injected is determined by the intraocular location of the chosen cells targeted for treatment. The cell type to be transduced will be determined by the particular disease entity that is to be treated.

For example, a single 20-microliter volume (of $10^{13}$ physical particle titer/ml rAAV) may be used in a subretinal injection to treat the macula and fovea. A larger injection of 50 to 100 microliters may be used to deliver the rAAV to a substantial fraction of the retinal area, perhaps to the entire retina depending upon the extent of lateral spread of the particles.

A 100-ul injection will provide several million active rAAV particles into the subretinal space. This calculation is based upon a titer of $10^{13}$ physical particles per milliliter. Of this titer, it is estimated that $1/1000$ to $1/10,000$ of the AAV particles are infectious. The retinal anatomy constrains the injection volume possible in the subretinal space (SRS). Assuming an injection maximum of 100 microliters, this would provide an infectious titer of $10^8$ to $10^9$ rAAV in the SRS. This would have the potential of infecting all of the $\sim 150 \times 10^6$ photoreceptors in the entire human retina with a single injection.

Smaller injection volumes focally applied to the fovea or macula may adequately transfect the entire region affected by the disease in the case of macular degeneration or other regional retinopathies.

Gene delivery vectors can alternately be delivered to the eye by intraocular injection into the vitreous. In this application, the primary target cells to be transduced are the retinal ganglion cells, which are the retinal cells primarily affected in glaucoma. In this application, the injection volume of the gene delivery vector could be substantially larger, as the volume is not constrained by the anatomy of the subretinal space. Acceptable dosages in this instance can range from 25 ul to 1000 ul.

4. Assays

A wide variety of assays may be utilized in order to determine appropriate dosages for administration, or to assess the ability of a gene delivery vector to treat or prevent a particular disease. Certain of these assays are discussed in more detail below.

a. Electroretinographic Analysis

Electroretinographic analysis can be utilized to assess the effect of gene delivery administration into the retina. Briefly, rats are dark adapted overnight and then in dim red light, then anesthetized with intramuscular injections of xylazine (13 mg/kg) and ketamine (87 mg/kg). Full-field scotopic ERGs are elicited with 10-$\mu$sec flashes of white light and responses were recorded using a UTAS-E 2000 Visual Electrodiagnostic System (LKC Technologies, Inc., Gaithersburg, Md.). The corneas of the rats are the anesthetized with a drop of 0.5% proparacaine hydrochloride, and the pupils dilated with 1% atropine and 2.5% phenylephrine hydrochloride. Small contact lenses with gold wire loops are placed on both corneas with a drop of 2.5% methylcellulose to maintain corneal hydration. A silver wire reference electrode is placed subcutaneously between the eyes and a ground electrode is placed subcutaneously in the hind leg. Stimuli are presented at intensities of −1.1, 0.9 and 1.9 log cd m$^{-2}$ at 10-second, 30-second and 1-minute intervals, respectively. Responses are amplified at a gain of 4,000, filtered between 0.3 to 500 Hz and digitized at a rate of 2,000 Hz on 2 channels. Three responses are averaged at each intensity. The a-waves are measured from the baseline to the peak in the cornea-negative direction, and b-waves are measured from the cornea-negative peak to the major cornea-positive peak. For quantitative comparison of differences between the two eyes of rats, the values from all the stimulus intensities are averaged for a given animal.

b. Retinal Tissue Analysis

As described in more detail above and below, retinal tissue analysis can also be utilized to assess the effect of gene delivery administration into the retina.

5. Pharmaceutical Compositions

Gene delivery vectors may be prepared as a pharmaceutical product suitable for direct administration. Within preferred embodiments, the vector should be admixed with a pharmaceutically acceptable carrier for intraocular administration. Examples of suitable carriers are saline or phosphate buffered saline.

Deposit Information

The following material was deposited with the American Type Culture Collection:

| Name | Deposit Date | Accession No. |
|---|---|---|
| PKm201bFGF-2 PD10-Kan-FGF-2-Sc | Mar. 11, 1999 | #207160 |

The above material was deposited by Chiron Corporation with the American Type Culture Collection (ATCC), 10801 University Blvd., Manassas, Va. 20110-2209, telephone 703-365-2700. This deposit will be maintained under the terms of the Budapest Treaty on the International Recognition of the Deposit of Microorganisms for purposes of Patent Procedure. The deposit will be maintained for a period of 30 years following issuance of this patent, or for the enforceable life of the patent, whichever is greater. Upon issuance of the patent, the deposits will be available to the public from the ATCC without restriction.

This deposit is provided merely as a convenience to those of skill in the art, and is not an admission that a deposit is required under 35 U.S.C. §112. The nucleic acid sequence of this deposit, as well as the amino acid sequence of the polypeptide encoded thereby, are incorporated herein by reference and should be referred to in the event of an error in the sequence described herein. A license may be required to make, use, or sell the deposited materials, and no such license is granted hereby.

The following examples are offered by way of illustration, and not by way of limitation.

EXAMPLES

Example 1

Construction of a RAAV Vector Expressing FGF-2 pKm201CMV is an AAV cloning vector in which an expression cassette, consisting of a CMV immediate early promoter/enhancer and a bovine growth hormone (BGH) polyadenylation site, is flanked by inverted terminal repeat (ITR) sequences from AAV-2. Briefly, pKm201CMV was derived from pKm201, a modified AAV vector plasmid in which the ampicillin resistance gene of pEMBL-AAV-ITR (see Srivastava, (1989) *Proc. Natl. Acad. Sci. USA* 86:8078–8082) had been replaced with the gene for kanamycin resistance. The expression cassette from pCMVlink, a derivative of pCMV6c (see Chapman, *Nucleic Acids Res.* 19:193–198 (1991)) in which the BGH poly A site has been substituted for the SV40 terminator, was inserted between the ITRs of pKm201 to generate pKm201CMV.

pKm201bFGF-2 was constructed by cloning the following, in order, into the multiple cloning site of pKm201CMV: the encephalomyocarditis virus (EMCV) internal ribosome entry site (IRES), the bovine FGF-2 CDNA, and the human growth hormone polyadenylation sequence. The cDNA for FGF-2 has two mutations that change amino acid 121 from serine to threonine and amino acid 137 from proline to serine. The DNA sequence of pKm201bFGF-2 is shown in FIG. 2 and the plasmid has been deposited with the American Type Culture Collection (ATCC).

rAAV vector particles were produced by a triple transfection protocol (*Nucleic Acids Res.* 24:59–601, 1996; *J. Exp. Med.* 179:1867–1875, 1994). Briefly, human embryonic kidney 293 cells, grown to 50% confluence in a 10 layer Nunclon cell factory (Nalge Nunc, Int., Naperville, Ill.), were co-transfected with 400 µg of helper plasmid pKSrep/cap (*Hum. Gene Ther.* 9:477–485, 1998) 400 µg of vector plasmid, and 800 µg of adenovirus plasmid pBHG10 (Microbix Biosystems, Inc., Toronto, Ontario) using the calcium phosphate co-precipitation method. Forty-eight hours after co-transfection, media was replaced with IMDM+10% FBS containing adenovirus type 5 dl312 at a multiplicity of infection (MOI) of 2. Seventy-two hours after infection cells were harvested and resuspended in HEPES buffer (200 ml total) and lysed by three cycles of freezing and thawing. Cell debris was removed by centrifugation at 12,000× g for 20 min. Packaged rAAV was purified from adenovirus by two rounds of cesium chloride equilibrium density gradient centrifugation. Residual adenovirus contamination was inactivated by heating at 56° C. for 45 min. Though three plasmids were used in the production of rAAV vector in this example, it is possible to combine the rAAV vector construct and the AAV helper gene construct on one plasmid. This would allow rAAV to be produced by transfecting 293 cells with two plasmids. Alternatively, one could add the adenovirus helper genes to this plasmid to make a single plasmid containing all that is required to make rAAV particles.

To estimate total number of rAAV particles, the virus stock was treated with DNAse I, and encapsidated DNA was extracted with phenol-chloroform, and precipitated with ethanol. DNA dot blot analysis against a known standard was used to determine titer (*Blood* 76:1997–2000, 1990).

To assay for adenovirus contamination, 293 cells were infected with 10 µl of purified rAAV stock and followed for any signs of cytopathic effect. All stocks were negative for adenovirus contamination (level of detection greater than or equal to 100 PFU/ml).

To assay for wild type AAV, 293 cells were co-infected with serial dilutions of rAAV stocks and adenovirus dl312 at a MOI of 2. Three days later the cells were harvested, lysed by three cycles of freezing/thawing, and centrifuged to remove cell debris. The supernatant was heat inactivated (56° C. for 10 min) and fresh plates of 293 cells ($6 \times 10^6$) were infected in the presence of adenovirus dl312 at a MOI of 2. Forty-eight hours after infection, low molecular-weight DNA was isolated (*J. Mol. Biol.* 26:365–369, 1967) subjected to agarose gel electrophoresis, and transferred to a nylon membrane. The membrane was hybridized with a biotinylated oligonucleotide probe specific for the AAV capsid region. The wild type AAV titer was defined as the highest dilution of rAAV vector stock demonstrating a positive hybridization signal. The rAAV preparations contained less than 1 wild type AAV genome per $10^9$ rAAV genomes.

Example 2

Infection of Cells with rAAV-CMV-FGF-2 Results in the Expression of FGF-2

293 cells were plated the day before infection at $5 \times 10^5$ cells/well in 6-well plates were infected with rAAV-CMV-bFGF-2 virus, prepared as described above in Example 1, at different multiplicities of infection (MOI) with and without etoposide (3 µM). Etoposide is a topoisomerase inhibitor which has been shown to increase transduction of rAAV vectors (*Proc. Natl. Acad. Sci. USA*, 92:5719–5723, 1995). Forty-eight infection, culture supernatant was collected and cells were lysed in 0.5 mL 1× lysis buffer (100 mM NaCl, 20 mM Tris pH 7.5, 1 mM EDTA, 0.5% NP40, and 0.5% deoxycholate). FGF-2 in the supernatants and lysates was assayed by ELISA (cat. # DFB00, & D Systems, Minneapolis, Minn.) following manufacturer's instructions. The shown below in Table 1.

TABLE 1

FGF-2 PRODUCTION IN 293 CELLS FOLLOWING INFECTION WITH RAAV-FGF-2

| sample | infection MOI | Etoposide | FGF2 protein |
|---|---|---|---|
| Culture Medium Supernatant (1.5 ml) | | | |
| 1 | 0 | – | <5 pg/ml |
| 2 | $2 \times 10^5$ | – | <5 pg/ml |
| 3 | $2 \times 10^4$ | – | <5 pg/ml |
| 4 | $2 \times 10^3$ | – | <5 pg/ml |
| 1 | 0 | + | <5 pg/ml |
| 2 | $2 \times 10^5$ | + | 106 pg/ml ≈ 300 pg/24 h/$10^6$ cells |
| 3 | $2 \times 10^4$ | + | <5 pg/ml |
| 4 | $2 \times 10^3$ | + | <5 pg/ml |
| Cell Lysate (0.5 ml) | | | |
| 1 | 0 | – | 8.95 ng/ml |
| 2 | $2 \times 10^5$ | – | 114. ng/ml |
| 3 | $2 \times 10^4$ | – | 18.8 ng/ml |
| 4 | $2 \times 10^3$ | – | 11.3 ng/ml |
| 1 | 0 | + | 5.05 ng/ml |
| 2 | $2 \times 10^5$ | + | 296. ng/ml ≈ 300 ng/24 h/$10^6$ cells |
| 3 | $2 \times 10^4$ | + | 48.0 ng/ml |
| 4 | $2 \times 10^3$ | + | 13.2 ng/ml |

Example 3

A. Construction of rAAV Vectors

Construction of pD10-bFGF-2

The pD10 AAV vector is constructed by replacing the AAV gene encoding sequences of pD-10 (see Wang, X. et al., *J. Virol.* 71:3077 (1997), with the CMV promoter, multiple cloning site, and BGH polyadenylation sequences from pKm201CMV. Briefly, oligonucleotides 5'-ggtatttaaa acttgcggcc gcggaatttc gactctaggc c-3' (SEQ I.D. No. 9) and 5'-gctgcccggg acttgctagc tggatgatcc tccagcgcgg ggatctcatg-3' (SEQ I.D. No. 10) are used to amplify the CMV expression cassette from pKm201CMV. The product of this PCR amplification is digested with SmaI and DraI and cloned into pD-10 digested with EcoRV. This new vector is named pD-10CMV.

To construct pD10-bFGF-2, the synthetic gene for bovine FGF-2 (see U.S. Pat. No. 5,464,774 for sequence) is digested with EcoRI and SalI, treated with T4 polymerase to blunt the ends, and then cloned into the StuI site of pD10-CMV. The synthetic gene described above encodes the mature, processed form of bovine FGF-2.

Figure 31:
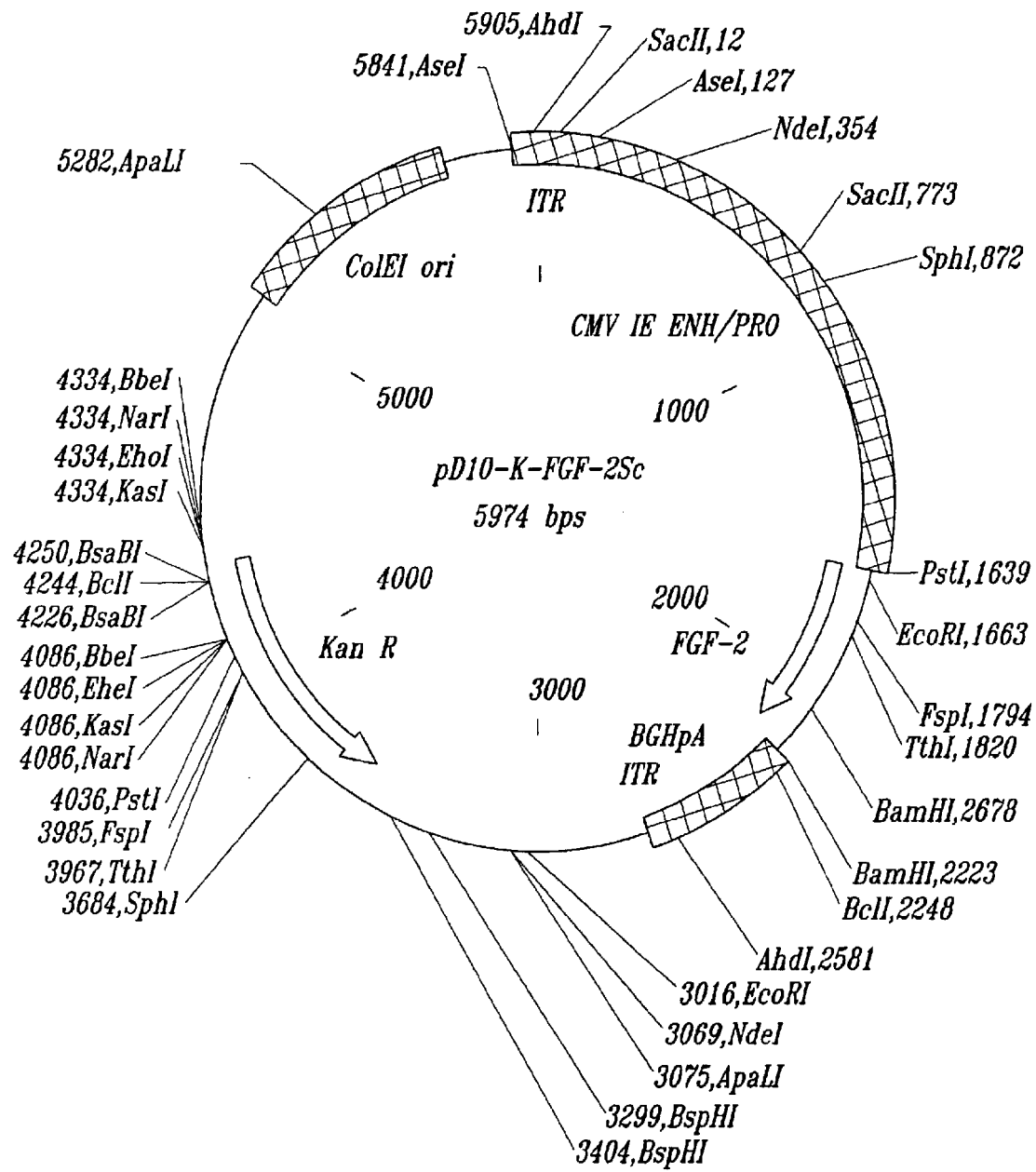
FIG. 31 is a schematic illustration of pD10K-FGF-2Sc.

Construction of a rAAV Vector Expressing FGF-2-Sc.

pD10-K-FGF-2-Sc (see FIG. 31) was constructed by cloning the FGF-2 full length humanized bovine cDNA obtained from Scios, into the pD10 vector backbone containing the kanamycin (Kan) resistance gene. This cDNA contains the mutations at amino acid positions 121 and 137 described in example 1. Briefly, the FGF-2-Sc cDNA was digested from the parent plasmid with the enzyme Nde1, the ends blunted with T4 DNA polymerase, cut with the restriction enzyme HindIII, and cloned into the pD10-CMV vector which had been digested with the enzymes StuI and HindIII. The nucleotide sequence of pD10-K-FGF-2-Sc is illustrated in FIG. 32.

C. Infection of Cells with rAAV-FGF-2-Sc Results in the Expression of FGF-2

293 cells were infected as in example 2, with the following modifications: 4×10e5 cells/well were plated in a 12 well dish, and all wells contained 3 uM etoposide. Three different particle numbers of FGF-2 virus, and a negative control CMV-lacZ virus were used to infect the cells. 48 hours after infection, tissue culture media was collected and cells lysed in 100 ul lysis buffer containing Triton-X 100 and Complete™ protein inhibitor cocktail (Boehringer Mannheim, Germany). FGF-2 protein in the media and lysates was assayed by ELISA. The results are shown below in Table 2 below.

TABLE 2

FGF-2 PRODUCTION IN 293 CELLS FOLLOWING INFECTION
WITH RAAV D10-K-FGF-2-Sc

| Vector | Viral Particles | Lysates(pg/mL) | Culture media (pg/mL) |
|---|---|---|---|
| D10-K-FGF-2-Sc | 1 × 10e10 | 324492.919 | 438.621 |
| D10-K-FGF-2-Sc | 1 × 10e9 | 32876.106 | 46.984 |
| D10-K-FGF-2-Sc | 1 × 10e8 | 6950.039 | 14.649 |
| CMV-lacz | 1 × 10e10 | 2327.527 | 17.096 |

Example 4
Construction of RAAV Vectors Which Express FGF5 AND FGF 18

A. Cloning FGF-5 into the pD10-CMV rAAV Vector.

The FGF-5 coding region (see U.S. Ser. No. 08/602,147) was cloned into the rAAV pD10-CMV vector by digestion with the enzymes SacII and XmnI, resulting in an 814 bp fragment. This removed an ORF (ORF-1) upstream of and overlapping with the FGF-5 coding region. The ends of the FGF-5 fragment were then blunted with T4 DNA polymerase, and it was cloned into the rAAV pD10-CMV vector linearized with StuI. This vector contains a 1353 bp insertion of a bacteriophage Phi X174 HaeIII fragment.

Figure 3:
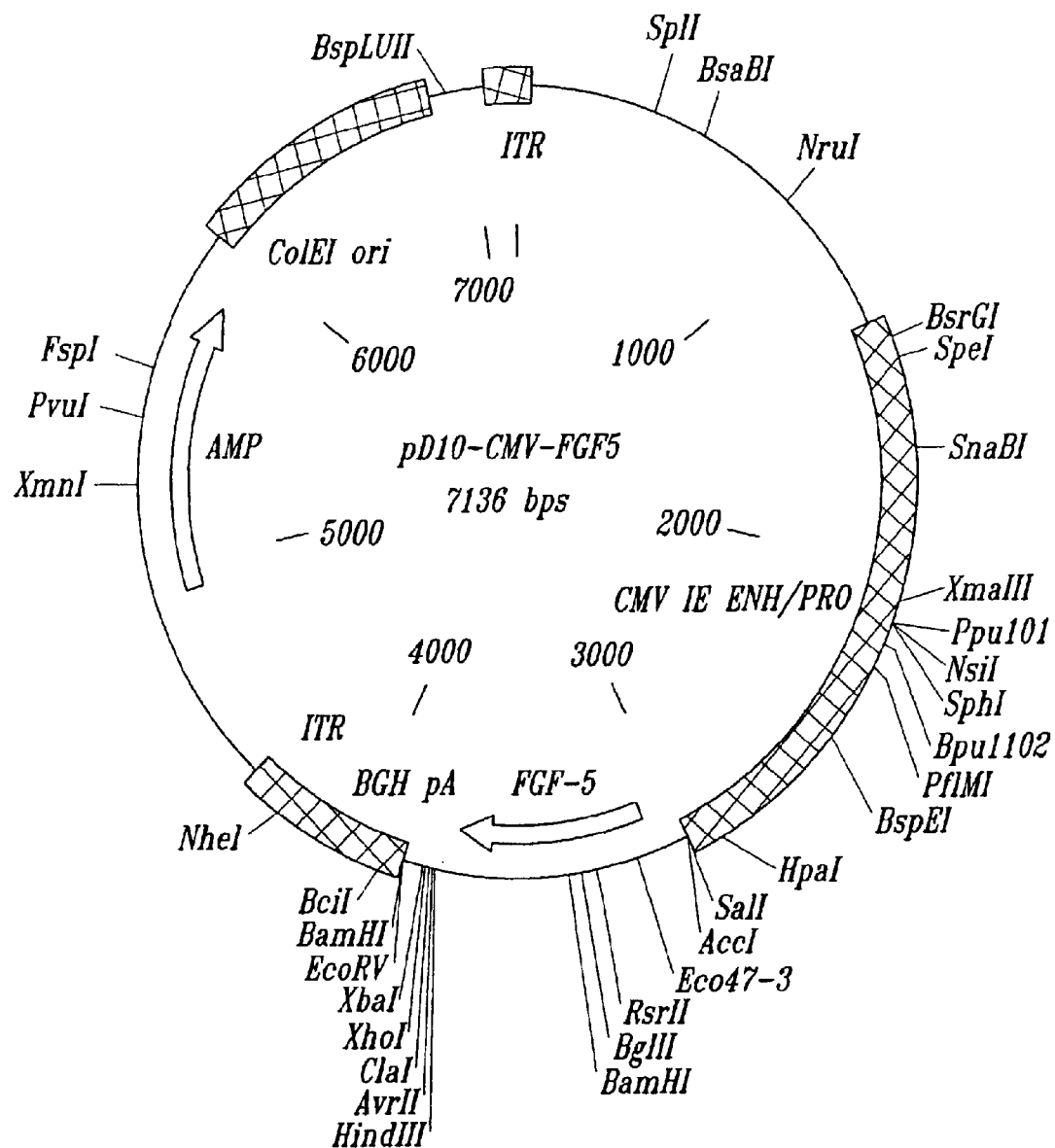
FIG. 3 is a schematic illustration of pD10-CMV-FGF-5.

The pD10-CMV-FGF-5 vector is illustrated schematically in FIG. 3. In summary, this plasmid contains the CMV immediate/early enhancer+promoter, the CMV intron A, an FGF-5 coding region, the bovine growth hormone polyA site, and AAV ITR sequences. There is a 1353 bp insertion of PhiX 174 bacteriophage DNA cloned into the Not1 site between one ITR and the CMV immediate early enhancer+ promoter region.

B. Packaging and Functional Analysis of FGF-5 rAAV.

rAAV virus was packaged using a triple transfection method as described in Example 1. However, rather than cesium chloride equilibrium density gradient centrifugation, heparin sulfate column chromatography is utilized. More specifically, a cell pellet is resuspended in TNM buffer: 20 mM Tris pH 8.0, 150 mM NaCl, 2 mM $MgCl_2$. Deoxycholic Acid is added to 0.5% to lyse the cells. 50 U/ml Benzonase is added and the lysed cells are incubated at 37 degrees to digest any nucleic acids. The cell debris is pelleted and the supernatant is filtered through a 0.45 um filter and then a 0.22 um filter. The virus is then loaded onto a 1.5 ml Heparin sulfate column using the Biocad HPLC. The column is then washed with 20 mM Tris pH 8.0, 100 mM NaCl. The rAAV particles are eluted with a gradient formed with increasing concentrations of NaCl. The fractions under the peak are pooled and filtered through a 0.22 um filter before overnight precipitation with 8% PEG 8000. $CaCl_2$ is added to 25 mM and the purified particles are pelleted and then resuspended in HBS#2: 150 mM NaCl, 50 mM Hepes pH7.4.

Briefly, $8 \times 10^8$ or $8 \times 10^9$ particles of the resulting FGF-5 virus were used to infect 293 cells, which were simultaneously treated with 3 uM etoposide to enhance viral expression levels. At 24 hours post-infection, tissue culture media and cell lysates were harvested and analysed by Western blotting. Briefly, protein samples were run on a 4–20% tris-glycine gradient gel, and transferred to nitrocellulose by standard procedures. After blocking with 5% milk in PBS, the membrane was incubated with an anti-human FGF-5 antibody (R and D systems, made in goat) at a dilution of 1:1,000 for one hour at room temperature. After the membrane was washed 3 times in PBS+0.05% Tween-20, it was incubated with an anti-goat secondary antibody conjugated to peroxidase (1:5,000 dilution). The membrane was then washed and the FGF-5 protein detected by chemiluminescence.

Figure 4:
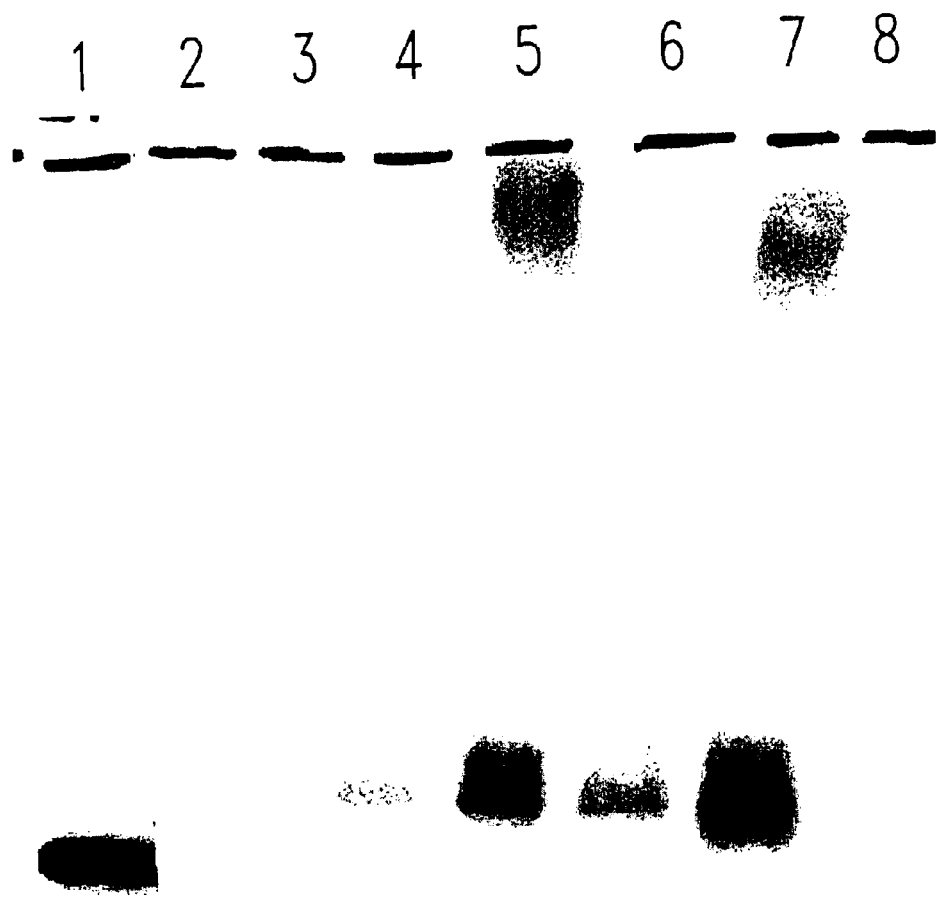
FIG. 4 is a western analysis of FGF-5 rAAV infected 293 cells.

Results of the Western blot are shown in FIG. 4. Briefly, lane 1 represents 50 ng of the 29.5 Kd recombinant FGF-5 protein (R and D systems). Lane 2, media from cells infected with $8 \times 10^9$ viral particles and treated with etoposide, shows no FGF-5 expression. Lane 3 is an uninfected cell lysate control. Lane 4 and 5 are lysates from cells infected with $8 \times 10^8$ or $8 \times 10^9$ viral particles, respectively, and Lanes 6 and 7 are lysates from cells infected with $8 \times 10^8$ or $8 \times 10^9$ viral particles and treated with 3 uM etoposide. Lanes 4–7 all show positive FGF-5 expression. Lane 8 is a negative control of lysate from uninfected cells.

In summary, although the FGF-5 signal sequence was intact, FGF-5 protein was detected in the cell lysate only.

C. Cloning FGF-5 Lacking a Signal Sequence, into rAAV pD10-CMV.

Figure 5:
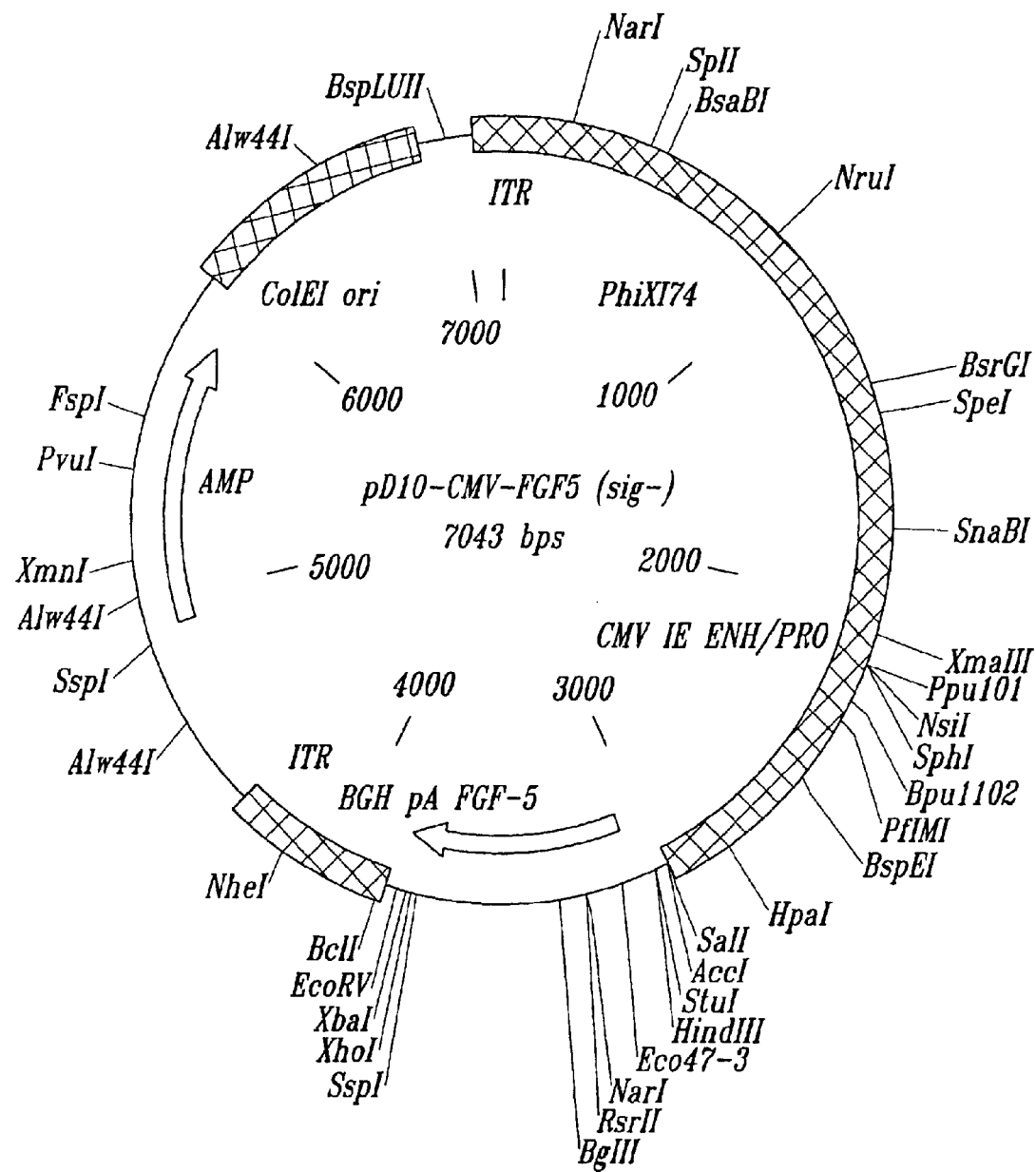
FIG. 5 is a schematic illustration of pD10-CMV-FGF-5 (sig-).

Oncogenic activity is associated with the wild-type FGF-5 molecule (Zhan et al., 1988; Bates et al., 1991). To improve its safety, the codons for the first 21 amino acids of FGF-5's signal sequence were removed by PCR amplification of the above pD10-CMV-FGF-5 plasmid with the following primers: AGA/TAT/AAG/CTT/ACC/ATG/GGT/GAA/AAG/CG T/CTC/GCC/CCC/AAA (5', 5FGFMUTB; SEQ I.D. No. 11) and CGC/GCG/CTC/GAG/AC C/ATG/AGG/AAT/ATT/AT C/CAA/AGC/GAA/ACT (3', 3FGF5WT; SEQ I.D. No 12). The 5' primer contains point mutations which destabilize G/C rich hairpin structures of the FGF-5 mRNA, and should increase levels of gene expression. The PCR product was digested with HindIII and XhoI (restriction sites introduced by the primers), and cloned by standard methods, into the pD10 vector digested with the same enzymes. The pD10 -CMV-FGF-5 (sig-) vector is illustrated schematically in FIG. 5.

In summary, the pD10-CMV-FGF-5 (sig-) plasmid contains the CMV immediate/early enhancer+promoter, the CMV intron A, the FGF-5 coding region with the modifications described in Example C above, the bovine growth hormone polyA site, and the AAV ITR sequences. There is a 1353 bp insertion of PhiX 174 bacteriophage DNA clones into the Not1 site between one ITR and the CMV immediate early enhancer+promoter region.

D. Western Analysis of 293 Cells Transfected with D10-CMV-FGF-5 (sig-).

Expression of FGF-5 protein was demonstrated by transient transfection of 293 cells with the plasmid pD10-CMV-FGF-5 (sig-), by standard methods. After 48 hours, tissue culture media and cell lysates were harvested. Western analysis was performed with an anti-human FGF-5 antibody (R and D systems) as described above.

Figure 6:
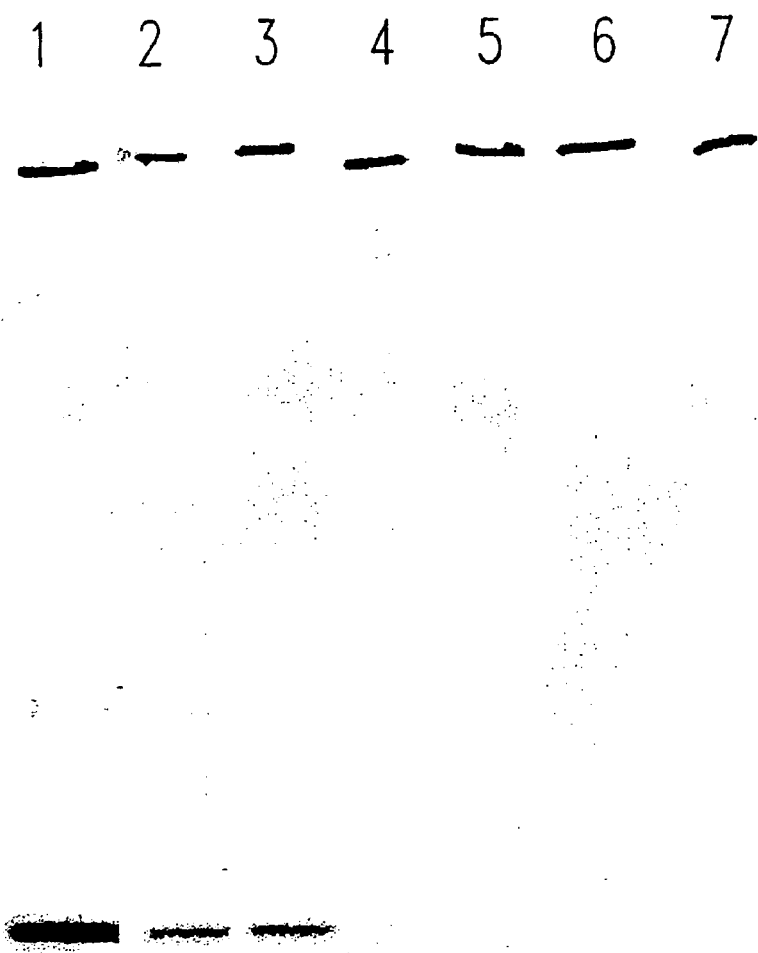
FIG. 6 is a western analysis of pD10-CMV-FGF-5 (sig-) transfected 293 cells.

Results of the Western analysis are provided below in FIG. 6. Briefly, lane 1 represents 50 ng of the 29.5 Kd recombinant FGF-5 protein (R and D systems). Lanes 2 and 3, showing FGF-5 expression, are cell lysates from 293 cells transfected with two different clones of the pD10-CMV-FGF-5 sig- plasmid. Lane 4 is lysate from cells transfected with a negative control plasmid CMV-Epo. Lanes 5, 6 and 7 represent media from cells transfected with different clones of the pD10-CMV-FGF-5 sig-plasmid, respectively, and the CMV-Epo plasmid. As is evident from this figure, FGF-5 protein was detected in the cell lysate only.

E. Generation of FGF-5 (signal-) rAAV.

FGF-5 (sig-) rAAV virus is packaged using the triple transfection method described in more detail above.

F. Cloning FGF-18 into the pD10-CMV rAAV Vector.

The FGF-18 coding region (see U.S. Provisional Application Ser. No. 60/083,553) was cloned into the pD10-CMV vector as a PstI to EcoRV fragment, using restriction sites found in both the FGF-18 and the multiple cloning site of the pD10-CMV vector. The vector contains a 1353 bp insertion of PhiX174 bacteriophage DNA (see Example A).

Figure 7:
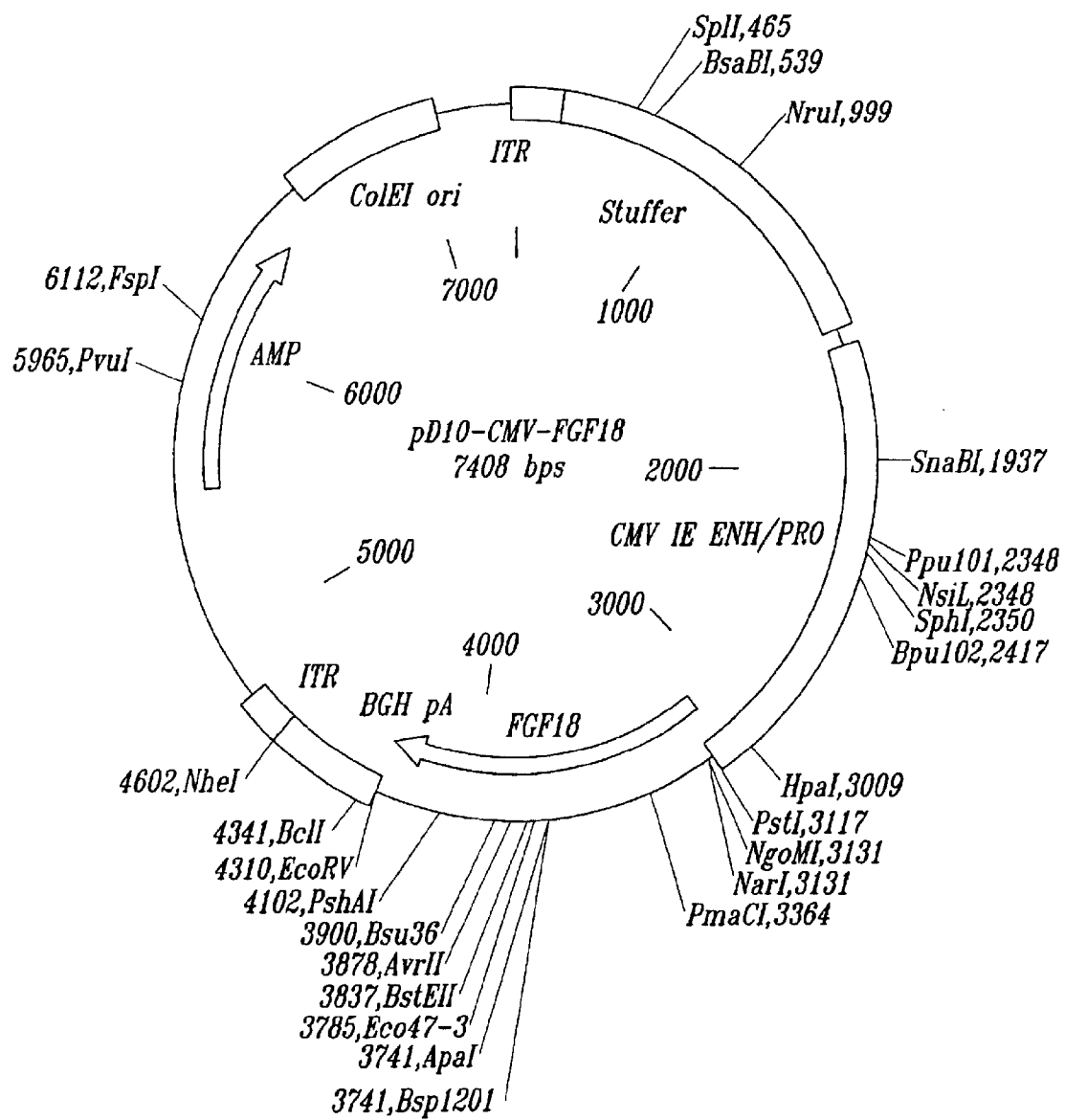
FIG. 7 is a schematic illustration of pD10-CMV-FGF-18.

A schematic illustration of pD10-CMV-FGF-18 is provided in FIG. 7. Briefly, this plasmid contains the CMV immediate/early enhancer+promoter, the CMV intron A, the FGF-18 coding region, the bovine growth hormone polyA site, and the AAV ITR sequences. There is a 1353 bp insertion of PhiX 174 bacteriophage DNA cloned into the Not1 site between one ITR and the CMV immediate early enhancer+promoter region.

G. Analysis of 293 Cells Transfected with pD10-CMV-FGF-18 Plasmid.

Expression of FGF-18 protein was assessed by transient transfection of 293 cells followed by Western analysis, using standard methods. Cell lysates and tissue culture media were harvested at 48 hours post transfection. An anti-peptide FGF-18 rabbit polyclonal antibody, generated against a selected polypeptide from recombinant FGF-18, was used at a dilution of 1:2,500 for one hour at room temperature. The secondary antibody, an anti-rabbit IgG conjugated to peroxidase, was used at a dilution of 1:25,000.

Figure 8:
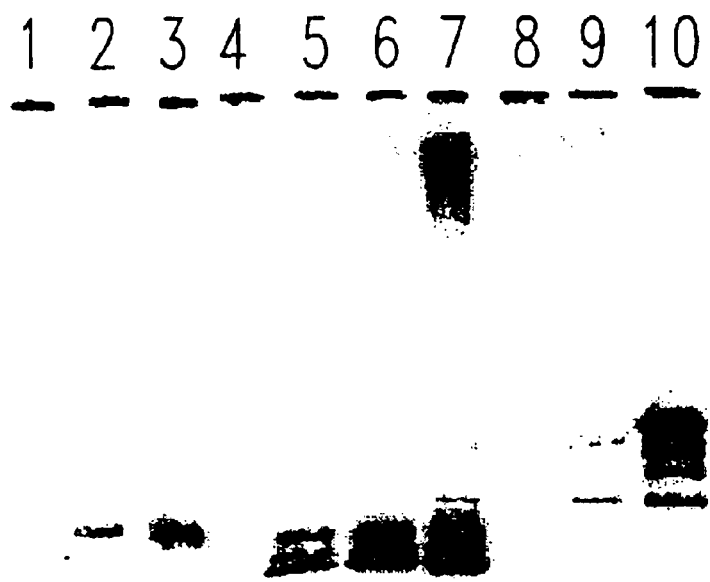
FIG. 8 western analysis of 293 cells transfected pD10-CMV-FGF-18.

Results of the Western analysis are provided in FIG. 8. Briefly, lanes 1–3 represent 1,2 and 10 ul of tissue culture media from cells transfected with the pD10-CMV-FGF-18 plasmid. Lane 4 is blank. Lanes 5, 6 and 7 contain 2, 10 and 20 ul of lysate from the transfected cells. Lanes 8 and 9 are negative controls; 20 ul of tissue culture media and cell lysate, respectively, from uninfected cells. Lane 10 contains a positive control; an FGF-18-maltose binding protein fusion ((MBP); predicted size=80 Kd, larger than the FGF-18 protein).

H. Packaging of the pD10CMV-FGF-18 Plasmid into rAAV Particles

FGF-18 rAAV virus was generated by the triple transfection method.

Example 5

AAV-LACZ Injected Retina

A. Subretinal injection of rAAV

Albino Sprague-Dawley rats were injected at 14–15 days postnatal (P14–P15). Animals were anesthetized by ketamine/xylazine injection, and a local anesthetic (proparacain HCl) was applied topically to the cornea. An aperture was made through the inferior cornea of the eye with a 28 gauge needle. Subretinal injections of 2–3µl of AAV-CMV-Lac-Z were then made by inserting a blunt 32 gauge needle through the opening and delivering the rAAV suspension into the subretinal space in the posterior retina. The contralateral eye was either uninjected, injected subretinally with PBS, or with a control rAAV containing a reporter gene.

B. Staining Protocol

Figure 9:
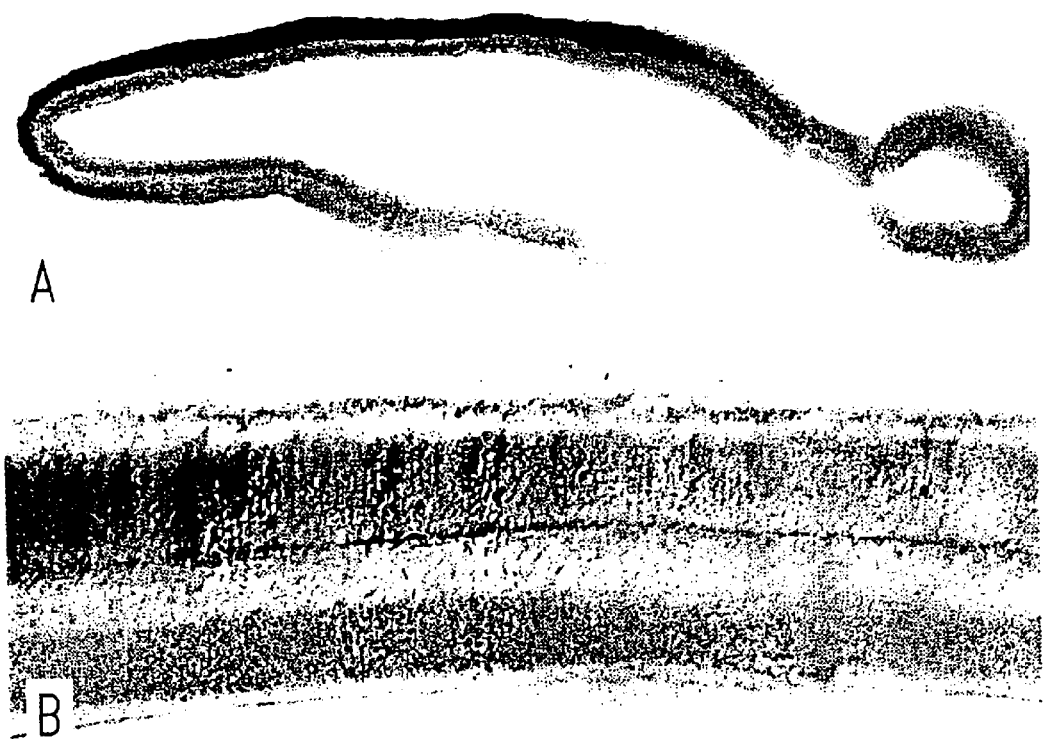
FIGS. 9A and 9B are photographs which show that bluo-gal staining is visible across 40% of a retina transfected with AAV-CMV-lacZ. All photoreceptors appear to express lacZ at the injection site, except at the edge where individual cells are visible.
Figure 10:
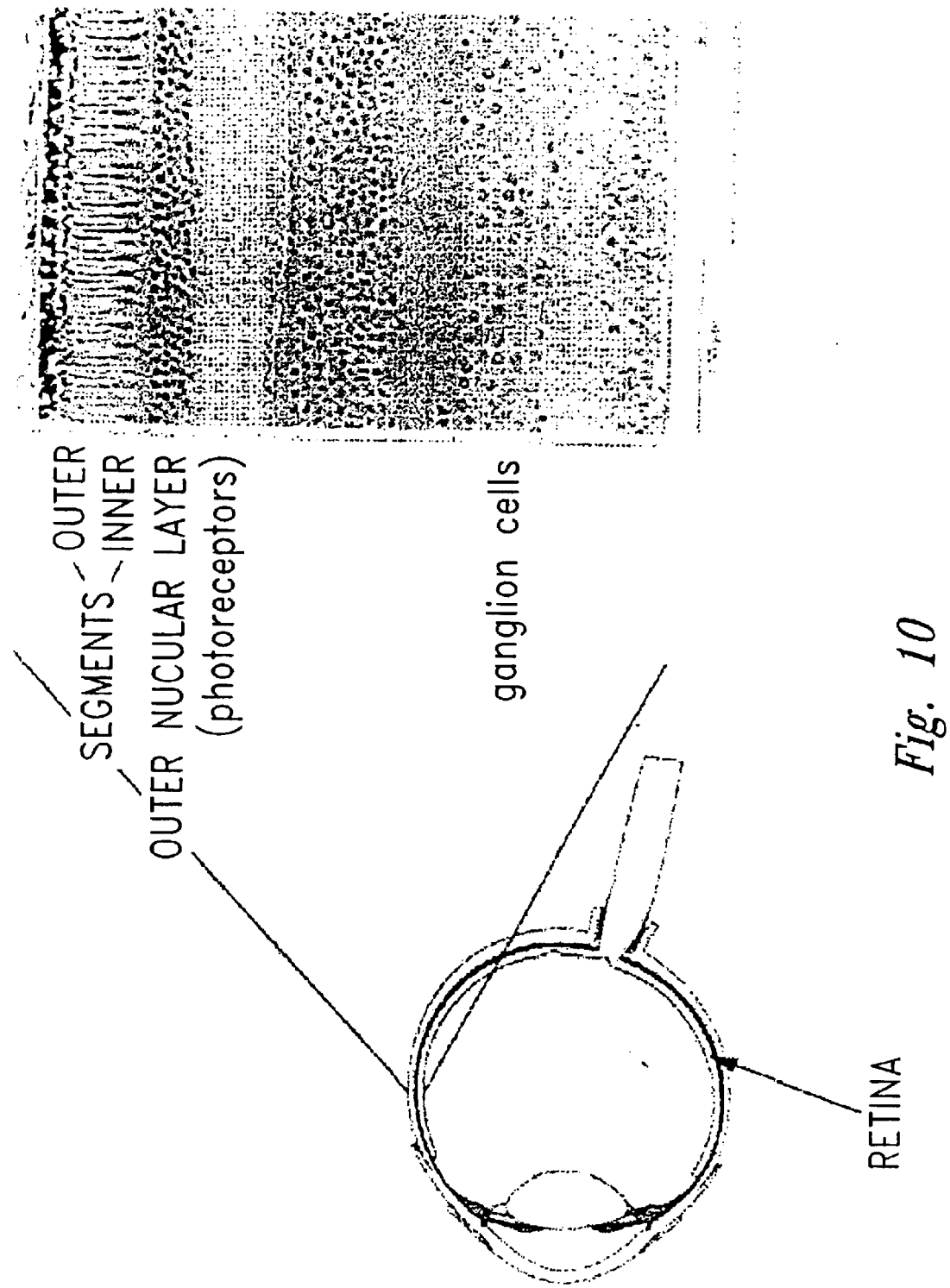
FIG. 10 is a schematic illustration which shows the retina within the eye, and the organization of cells within the retina.
Figure 11:
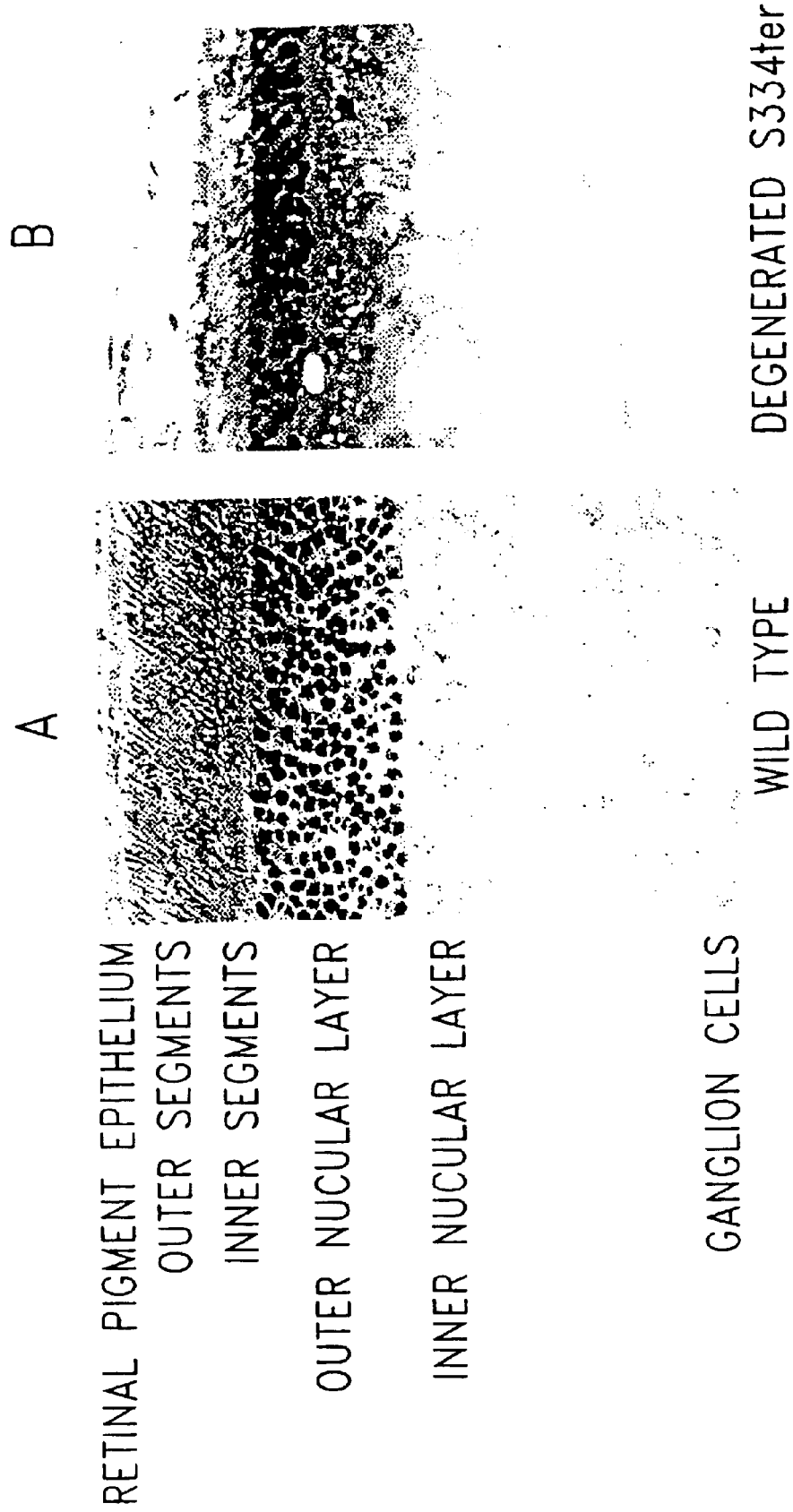
FIGS. 11A and 11B are photographs of wild-type and degenerated S334tcr rat retinas. S334tcr is a rat model for retinitis pigmentosa.
Figure 12:
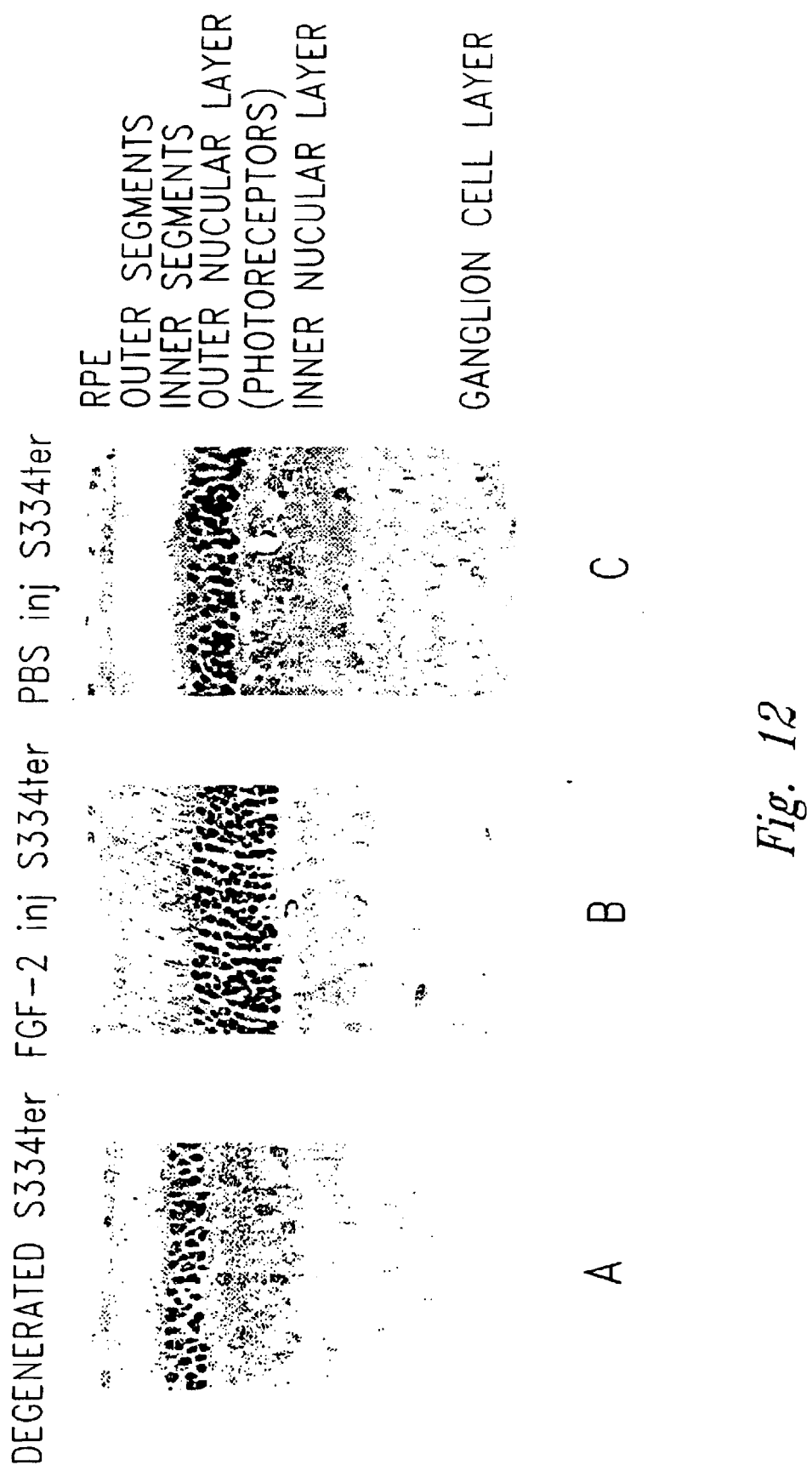
FIGS. 12A, 12B and 12C are photographs of degenerated S334ter, FGF-2 injected S334ter and PBS injected S334ter rat retinas. As can be seen in these figures, FGF-2 injected into the S334ter rat retina substantially slows the progression of disease.
Figure 13:
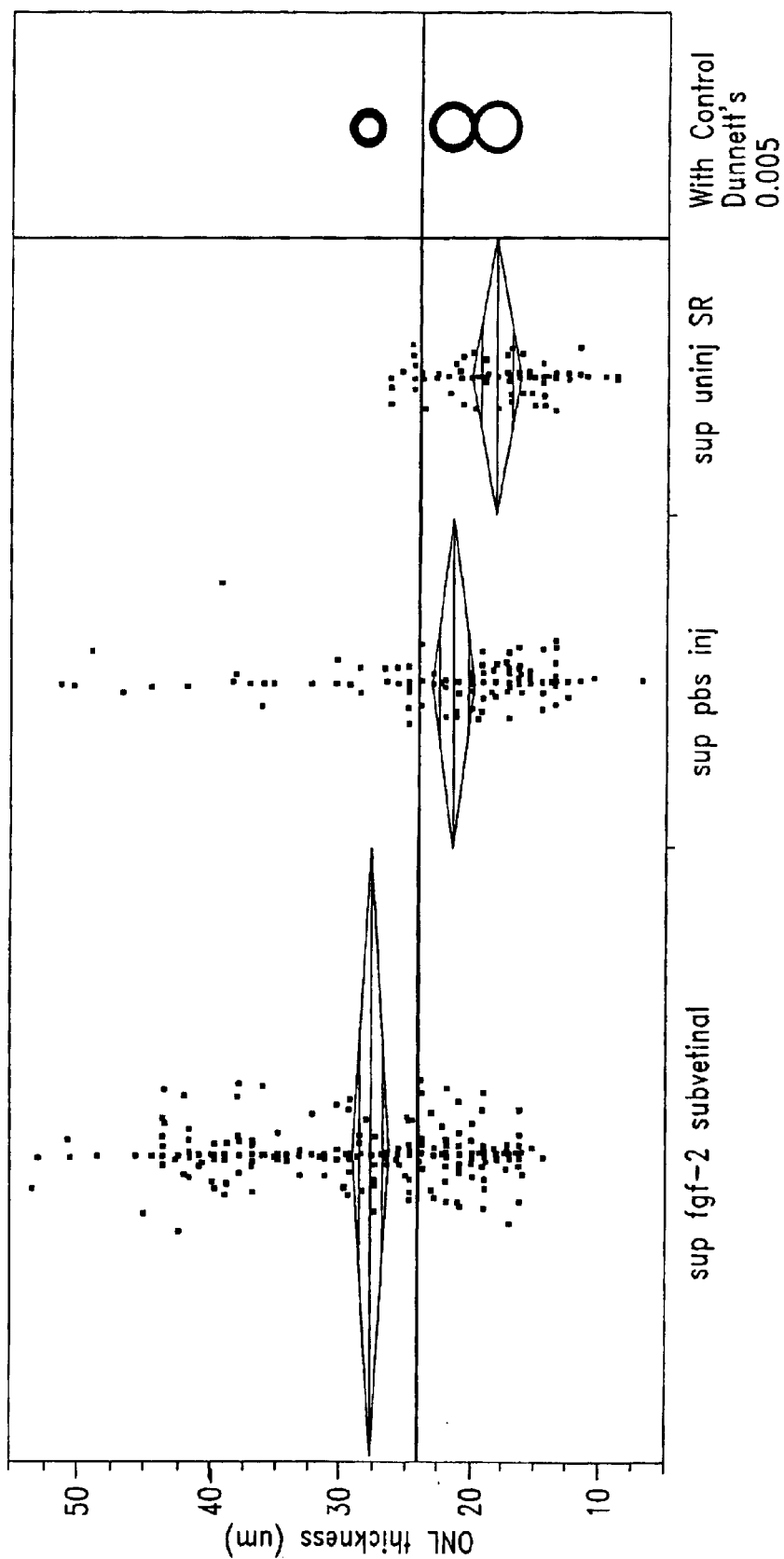
FIG. 13 is a graph which plots Outer Nuclear Layer (ONL) thickness for FGF-2 subretinally injected, PBS subretinally injected, and an uninjected control.
Figure 14:
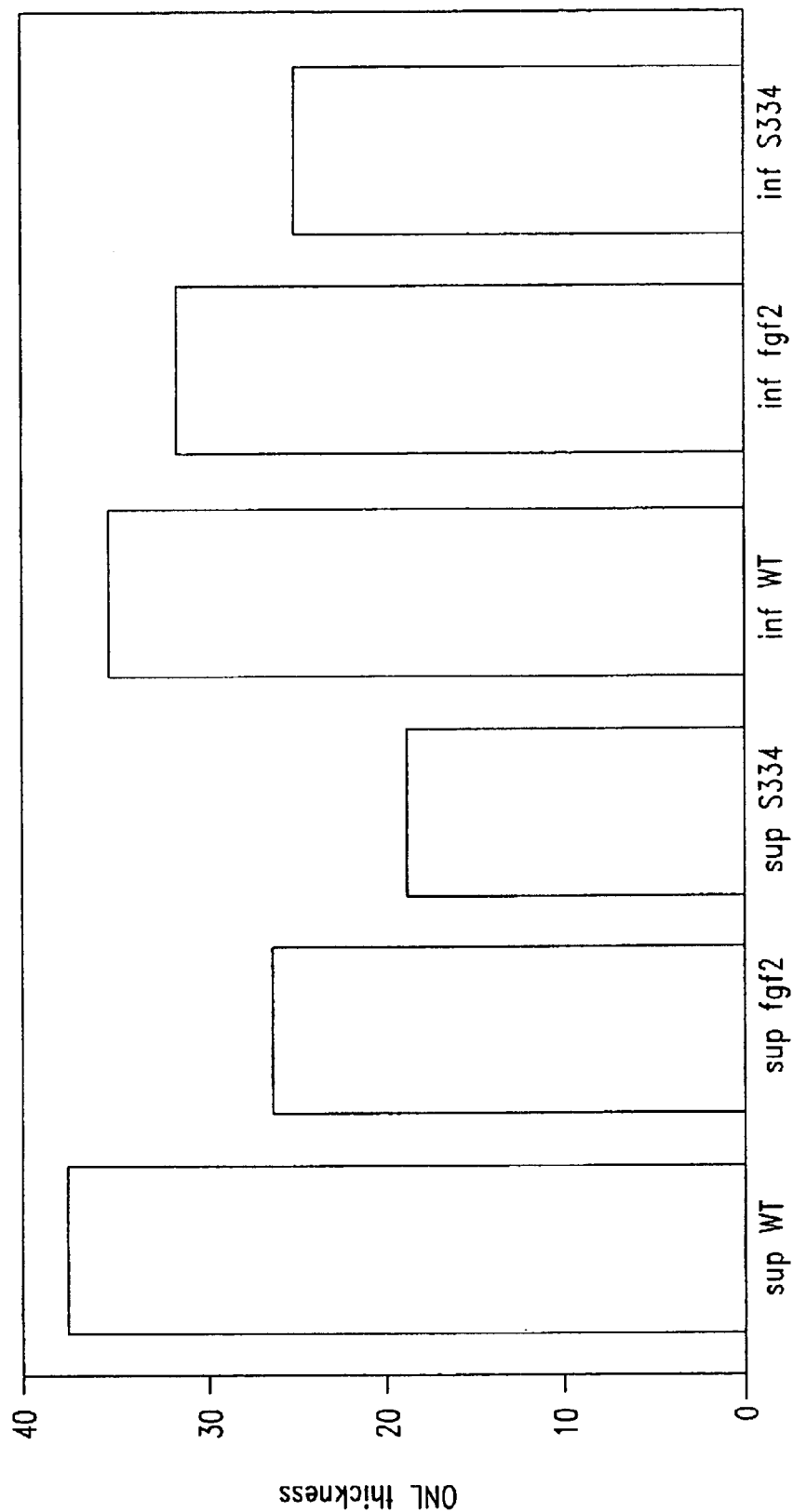
FIG. 14 is a bar graph which plots ONL thickness at p60.

Cryosections of the retina were stained with Bluo-gal for b-galactosidase reaction product of lacZ. In all wild type rats tested (3), positive staining was visible in the interior of the whole eyecup upon gross examination (see FIG. 9). 100 µm thick agarose or 20 µm thick cryosections of retinas indicated that most of the b-gal positive staining localized to the photoreceptors. There were a small number of LacZ positive retinal ganglion cells observed.

C. Anti-b-galactosidase Immunocytochemistry

Sections from 3 wildtype and 2 transgenic rats were stained with a polyclonal antibody against b-galactosidase. These results were comparable to the bluo-gal results, primarily demonstrating photoreceptor-specific staining. Two out of five rats showed no positive staining.

D. Results

Subretinal injection of 2 ul of AAV-CMV-lacZ effectively transduced a large number of photoreceptor and retinal pigment epithelial (rpe) cells following a single intraocular inoculation of AAV-CMV-lacZ into the subretinal space (SRS) of the rat eye. The lateral extent of lacZ reporter gene expression was typically ⅓ to ½ of the retinal expanse following a single AAV-CMV-LacZ injection. This finding was confirmed by bluo-gal staining of the b-galactosidase reaction product of the lacZ gene as well as by immunocytochemistry using an antibody specific for b-galactosidase. The AAV-CMV-lacZ vector was effective at transducing photoreceptor and RPE cells in both the normal (wildtype) and affected, degenerating (transgenic) rat retina.

Example 6

Retinal Tissue Analysis of RAAV-FGF-2 Infected Cells, VS. Controls

A. Subretinal Injection of rAAV

Line 3 albino transgenic rats (P23FH-3) on an albino Sprague-Dawley background (produced by Chrysalis DNX Transgenic Sciences, Princeton, N.J.) were injected at the ages of P14 or P15. Animals were anesthetized by ketamine/xylazine injection, and a local anesthetic (proparacain HCl) was applied topically to the cornea. An aperture was made through the inferior cornea of the eye with a 28 gauge needle. The subretinal injections of 2 µl were then made by inserting a blunt 32 gauge needle through the opening and delivering the rAAV suspension into the subretinal space in the posterior retina. The intent was to inject into the subretinal space of the posterior superior hemisphere, but some-times upon histological examination it was found that the injection site was located just inferior to the optic nerve head. The opposite eye was either uninjected, injected subretinally with PBS, with control rAAV containing no neurotrophin or containing proteins not known to possess neurotrophic properties.

B. Histopathology Protocol/Retinal tissue analysis

The rats were euthanized by overdose of carbon dioxide inhalation and immediately perfused intracardially with a mixture of mixed aldehydes (2% formaldehyde and 2.5% glutaraldehyde). Eyes were removed and embedded in epoxy resin, and 1 μm thick histological sections were made along the vertical meridian. Tissue sections were aligned so that the ROS and Müller cell processes crossing the inner plexiform layer were continuous throughout the plane of section to assure that the sections were not oblique, and the thickness of the ONL and lengths of RJS and ROS were measured as described (see e.g., LaVail, et al. PNAS 1992, 89(23:11249–53 and LaVail et al., Invest. Ophthamlmol. Vis. Sci 1998, 39(3):592–602). Briefly, 54 measurements of each layer or structure were made at set points around the entire retinal section. These data were either averaged to provide a single value for the retina, or plotted as a distribution of thickness or length across the retina. The 3 greatest contiguous values for ONL thickness was also compared in each retina, to determine if any region of retina (e.g., nearest the injection site) showed proportionally greater rescue; although most of these values were slightly greater than the overall mean of all 54 values, they were no different from control values than the overall mean. Thus, the overall mean was used in the data cited, since it was based on a much larger number of measurements.

C. Results

Two surgical methods of delivery of rAAV-CMV-FGF2 were completed, intravitreal and subretinal injection.

1. Intravitreal Injection

RAAV-CMV-FGF-2 was injected into the right eye of nine transgenic S334ter rats after day P15 (the left eye was not injected). S334(4) transgenic animals were used to assess the rescue effect of rAAV-CMV- FGF-2 on degenerating photoreceptor cells when delivered by intravitreal injection. The rats were all sacrificed at age p60 and the embedded in plastic and sectioned to assess morphology and therapeutic effect as assayed by the preservation of thickness of outer nuclear layer. Superior and inferior regions of eyecup are quantitated by measuring the ONL thickness using a BioQuant morphometric measuring system (BioQuant). Injected eyes were evaluated along with uninjected control eyes.

Control Left superior—16.52+/−2.77 um
Injected Right superior—19.71+/−5.27 um
Control Left inferior—22.64+/−2.11 um
Injected Right inferior—26.47+/−3.55 um Based upon these results it was evident that there is a rescue effect of AAV-CMV-FGF-2 when delivered intraocularly into the vitreous cavity.

2. Subretinal Injection of rAAV-CMV-FGF-2

Experiment A.—Location of injection—subretinal, 7 rats—both right and left eyes injected, 3 rats—(left eye= uninjected). Number of rats injected—10 rats all wild type p15 on day of injection. One rat was sacrificed every week starting at week 2. Expression of FGF-2 was assessed, as well as any signs of inflammation or neovascularization.

Experiment B.—Location of injection—subretinal, 5 rats—right eyes injected w/vector left eyes injected with PBS, 4 rats—right eyes injected w/vector (left eye= uninjected). Number of rats injected—11 transgenic S334(4) rats—all were p15 on day of injection. The rats were sacrificed at age p60 and the embedded in plastic and sectioned to assess histopathology and number of surviving photoreceptor cells.

Anatomic indication of therapeutic effect (photoreceptor rescue) was assessed histologically. Briefly, eyes injected with rAAV-CMV-FGF2 retained significantly more photoreceptors at P60, P75 and P90 than uninjected contralateral control eyes of the same animal. Retinas receiving a subretinal injection of AAV-CMV-FGF2 at P14–15 retained 71% of the normal ONL thickness, compared to about 47% in the uninjected controls (see FIGS. 11, 12, 13 and 14).

There was little or no rescue in PBS-injected control eyes (p>0.169 in all cases). This is consistent with previous reports that needle injury to the retina in young rats (P14–P15) does not rescue photoreceptors or up-regulate bFGF mRNA expression.

3. Subretinal Injection of rAAV-CMV-FGF-2

Two to three microliters of rAAV-CMV-FGF-2 vector was injected into the subretinal space between the photoreceptors and the adjacent retinal pigment epithelium at P14 or P15. Rats were sacrificed and eyes examined at time points between P60–P90. At these ages in uninjected control eyes of S334ter rats, the ONL thickness, which is an index of photoreceptor cell number, was reduced to about 60% of normal.

Evidence of anatomic rescue was found to be significant to the p=0.005 confidence level in retinas transfected by rAAV-CMV-FGF-2 when compared to the control AAV vectors or sham injection of PBS by ANOVA (analysis of Variance statistical measures). JMP statistical analysis software (Copyright (c) 1999 SAS Institute Inc. Cary, N.C. USA).

Example 7

Antibody Staining of RAAV-FGF-2 Infected Cells

A. Injection Protocol

Albino Sprague-Dawley rats were injected with rAAV-CMV-FGF-2 at the ages of P14 or P15.essentially as follows. Briefly, wild-type animals were anesthetized by ketamine/xylazine injection, and a local anesthetic (proparacain HCl) was applied topically to the cornea. An aperture was made through the inferior cornea of the eye with a 28 gauge needle. The subretinal injections of 2–3 ul of rAAV-CMV-FGF-2 were then made by inserting a blunt 32 gauge needle through the opening and delivering the rAAV suspension into the subretinal space in the posterior retina. The contralateral eye was either uninjected, injected subretinally with PBS, wild-type rAAV, or with rAAV-CMV-lacZ.

B. Staining Protocol

Fixed eyecups were embedded in OCT and cryosectioned in 20 um thick sections. Sections from 10 wt rats were stained with antibody to FGF-2. (primary-anti-FGF-2 1:500 (commercial antibody purchased from R&D systems) (secondary-anti-goat Cy3 conjugate (Sigma, St. Louis. Mo.)

C. Results

Immunohistochemistry was used to look for expression of FGF-2 in the eye. Two rats were examined every week starting at 3 weeks post-injection. Retinas were examined for expression of FGF-2 and also examined histopathologically for signs of inflammation or neovascularization.

Results are shown in FIG. 15. Briefly, expression of FGF-2 was found in retinal photoreceptor cells as well as RPE cells at 35 days following inoculation with 2–3 ul of rAAV-CMV-FGF-2. Less significant expression was noted in retinal bipolar interneurons and retinal ganglion cells (RGCs) following injection into the subretinal space (SRS). No significant staining above background was observed in sections injected with PBS or rAAV-CMV-lacZ vectors.

Example 8

Retinal Tissue Analysis of RAAV-FGF-5 (SIG-) AND-18 Infected Cells, VS. Controls A. Subretinal Injection of rAAV Line 4 albino transgenic rats (S334ter-4) on an albino Sprague-Dawley background (produced by Chrysalis DNX Transgenic Sciences, Princeton, N.J.) were injected at age P15. Animals were anesthetized by ketamine/xylazine injection, and a local anesthetic (proparacain HCl) was applied topically to the cornea. An aperture was made through the inferior cornea of the eye with a 28 gauge needle. The subretinal injections of 2.5 µl were then made by inserting a blunt 32 gauge needle through the opening and delivering the rAAV suspension into the subretinal space in the posterior retina. The opposite eye was either uninjected, injected subretinally with PBS, with control rAAV containing no neurotrophin or containing proteins not known to possess neurotrophic properties.

B. Histopathology Protocol/Retinal Tissue Analysis

The rats were euthanized by overdose of carbon dioxide inhalation and immediately perfused intracardially with a mixture of mixed aldehydes (2% formaldehyde and 2.5% glutaraldehyde). Eyes were removed and embedded in epoxy resin, and 1 µm thick histological sections were made along the vertical meridian. Tissue sections were aligned so that the ROS and Müller cell processes crossing the inner plexiform layer were continuous throughout the plane of section to assure that the sections were not oblique, and the thickness of the ONL was measured as described (LaVail, et al). Briefly, 54 measurements of each layer or structure were made at set points around the entire retinal section. The 27 measurements from the inferior region and the superior region of the retina were averaged separately to give two values for each eye. This separation was made because the retina degenerates at different rates in these two regions of the S334ter-4 animal model.

C. Results

Sub-retinal injections of both rAAV-CMV-FGF-5 (sig-) and rAAV-CMV-FGF-18 were performed.

1. Sub-retinal Injection of rAAV-CMV-FGF-5 (sig-)

Experiment.—Location of injection—subretinal, 3 rats—right eyes injected w/vector left eyes injected with PBS, 8 rats—right eyes injected w/vector left eyes injected with rAAV-CMV-LacZ, 4 rats—right eyes injected w/vector (left eye=uninjected). Number of rats injected—15 transgenic S334ter4 rats—all were p15 on day of injection. The rats were sacrificed at age p60. The retinas were embedded in plastic and sectioned to assess histopathology and number of surviving photoreceptor cells.

Figure 33:
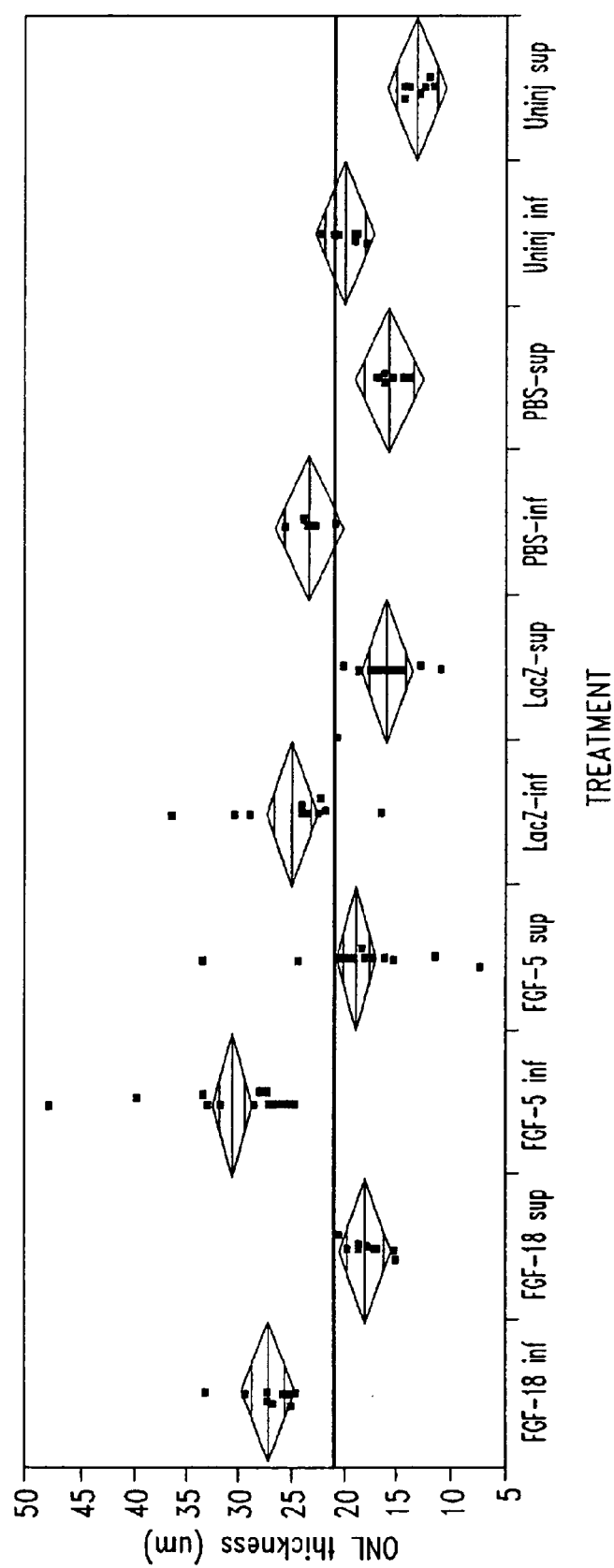
FIG. 33 is a graph that compares ONL thickness (um) after injection of various vectors into the eye.

Anatomic indication of therapeutic effect (photoreceptor rescue) was assessed histologically. The injection of rAAV-CMV-FGF-5 (sig-) resulted in significant rescue of photoreceptors, compared to PBS injected, rAAV-CMV-LacZ injected, and uninjected eyes (see FIG. 33). The rescue was significant to the p=0.05 confidence level for all three comparisons, by ANOVA (analysis of Variance statistical measures). JMP statistical analysis software (Copyright (c) 1999 SAS Institute Inc. Cary, N.C. USA).

2. Sub-retinal Injection of rAAV-CMV-FGF-18

Experiment.—Location of injection—subretinal, 3 rats—right eyes injected w/vector left eyes injected with PBS, 3 rats—right eyes injected w/vector left eyes injected with rAAV-CMV-LacZ, 4 rats—right eyes injected w/vector (left eye=uninjected). Number of rats injected—10 transgenic S334ter-4 rats—all were p15 on day of injection. The rats were sacrificed at p60, and the retinas embedded in plastic and sectioned.

Eyes injected with rAAV-CMV-FGF-18 retained significantly more photoreceptors at P60 than PBS injected, rAAV-CMV-LacZ injected, or uninjected control eyes. Each comparison, by ANOVA, was statistically significant to the p=0.05 confidence level.

Example 9

In Vivo Delivery to Retinal Ganglion Cells (RGCs)

A. Intra-vitreal injection of AAV Vectors

All surgical procedures were performed in female adult Sprague-Dawley rats (180–200 g; Charles River Breeders) under general anesthesia (7% chloral hydrate; 0.42 mg per g of body weight, i.p.) in accordance with the Use of Animals in Neuroscience Research and McGill University Animal Care Committee guidelines for the use of experimental animals.

Briefly, rAAV-CMV-lacZ (5 µl; see above) was injected into the vitreous chamber in the superior (dorsal) hemisphere of the retina using a posterior approach as described (Di Polo, PNAS, 1998). Control eyes were injected with equal volumes of Hepes-buffered saline (HBS, virus vector).

B. Identification of RPCs

For visualization of RGCs, neurons were retrogradely labeled with the fluorescent tracer Fluorogold (Fluorochrome, Englewood, Colo.) at 2% in 0.9% NaCl containing 10% dimethyl sulfoxide by application of the tracer to both superior colliculi 7 days prior to analyses as described (Vidal-Sanz et al., 1988). Anesthetized rats were then perfused intracardially with 4% paraformaldehyde in 0.1 M phosphate buffer (PB, pH 7.4) and the eyes were immediately enucleated. The anterior part of the eye and the lens were removed and the remaining eye cup was immersed in the same fixative for 2 hr at 4° C. Eye cups were cryoprotected in graded sucrose solutions (10–30% in PB) for several hours at 4° C., embedded in O.C.T. compound (Tissue-Tek, Miles Laboratories, Elkhart, Ind.) and frozen in a 2-methylbutane/liquid nitrogen bath. Retinal radial cryosections (12–15 µm), obtained along the vertical meridian of the eye, were collected onto gelatin-coated slides and processed for immunocytochemistry. Alternatively, entire eyes were rinsed three times (15 min each) in PBS at room temperature with gentle shaking, to whole-mount histochemical staining as described below.

C. Histochemical Analysis

Expression of the bacterial LacZ gene in whole retinas was detected by standard histochemical staining reactions using halogenated indoyl-β-D-galactoside (Bluogal; GIBCO BRL). Following removal of the anterior eye structures and lens, eye cups were incubated overnight in a staining solution containing 5 mM K-ferricyanide, 5 mM K-ferrocyanide, 2 mM $MgCl_2$, and 0.5 mg/ml Bluo-gal at 37° C. Retinas were then dissected, fixed for an additional 30 min and flat-mounted vitreal side up on glass slides.

For visualization of the AAV-mediated lacZ gene product in retinal radial sections, cryosections were incubated in 10% normal goat serum (NGS) in 0.2% Triton X-100 (Sigma, St. Louis, Mo.) in phosphate buffer saline (PBS) for 30 min at room temperature to block non-specific binding. Two primary antibodies raised against the lacZ gene product were used with similar results. A polyclonal anti-betagal antibody (diluted 1:1000; 5 prime→3 prime, Inc., Boulder, Co.) and a monoclonal anti-LacZ antibody (diluted 1:500;

Promega, Madison, Wis.). Primary antibodies were added in 2% NGS in 0.2% Triton X-100 and incubated overnight at 4° C. Sections were subsequently processed with anti-rabbit Cy3-conjugated IgG (diluted 1:500, Jackson Immunoresearch, West Grove, Pa.) or anti-mouse Cy3-conjugated IgG (diluted 1:500, Jackson Immunoresearch) and mounted. Control sections were treated in the same way but with omission of the primary antibody. Sections were visualized by fluorescent microscopy (Polyvar, Reichert-Jung).

Expression of the heparan sulfate proteoglycan receptor in the retina was examined using a monoclonal anti-heparan sulfate antibody (HepSS-1, diluted 1:1,000, Seikagaku Corporation, Tokyo, Japan). Following overnight incubation at 4° C., sections were processed with biotinylated anti-mouse Fab fragment (Jackson Immunoresearch), avidin-biotin-peroxidase reagent (ABC Elite Vector Labs, Burlingame, Calif.), followed by reaction in a solution containing 0.05% diaminobenzidine tetrahydrochloride (DAB) and 0.06% hydrogen peroxide in PB (pH 7.4) for 5 min. For analysis of co-localization of heparan sulfate in Fluorogold-labeled neurons, sections were processed with Cy3-coupled anti-mouse IgG (Jackson Immunoresearch) after incubation in primary antibody. In all cases, the primary antibody was omitted in control sections. Sections were mounted and visualized by light or fluorescent microscopy.

Quantification of AAV-transduced cells in the ganglion cell layer of retinal flat-mounts was performed in two ways: i) by counting the entire number of Bluo-gal positive cells in each of the retinal quadrants (superior, inferior, temporal and nasal); and ii) by counting the number of cells in three standard areas (at 1, 2 and 3 mm from the optic disc) of each quadrant as previously described (Villegas-Perez et al., 1993).

For quantification of Fluorogold, Bluo-gal or HepSS-1 positive cells in retinal radial sections, the entire number of labeled cells per section was counted under fluorescent microscopy. Four to five serial sections per eye were routinely counted and a mean value per animal was obtained, followed by the calculation of a mean value for the entire experimental group which consisted of 4–5 rats. Results were analyzed using the Sigmastat program (Jandel, San Rafael Madera, Calif.) by a student's t test (paired groups).

D. Results

Figure 16:
FIGS. 16A and 16B are photographs which show gene delivery to cells in the ganglion cell layer following intraocular injection of recombinant rAAV-CMV-lacZ. a) superior quadrant of a retinal flat-mount processed for Bluo-Gal staining to visualize AAV-infected neurons. Notice the large number of axons converging at the optic nerve head (asterisk). b) Retinal radial section showing the AAV-mediated LacZ gene product in cells of the ganglion cell layer. A large number of these cells can be identified as RGCs because of the intense LacZ staining in axons projecting to the optic nerve head (asterisk). RPE: retinal pigment epithelium, PS: photoreceptor segments, ONL: outer nuclear layer, OPL: outer plexiform layer, INL: inner nuclear layer, IPL: inner plexiform layer, GCL: ganglion cell layer. Scale bars: a) 0.5 mm, b) 50 $\mu$m.

Analysis of retinas from eyes that received a single intravitreal injection of rAAV-CMV-lacZ demonstrated a large number of LacZ-positive cells throughout the entire GCL as assessed by histochemical LacZ staining of both flat-mounts (FIG. 16A) and radial sections (FIG. 16B). In many cases, RGCs transduced by AAV could be unequivocally identified because the LacZ reaction product filled their axons that converged at the level of the optic nerve head. In addition, LacZ-positive photoreceptor nuclei were observed but were always restricted to the vicinity of the injection site (not shown). No staining was observed in control eyes injected with virus vector. No signs of cytotoxic damage or cellular immune reaction to the viral vector were observed in any of the retinas examined.

Figure 17:
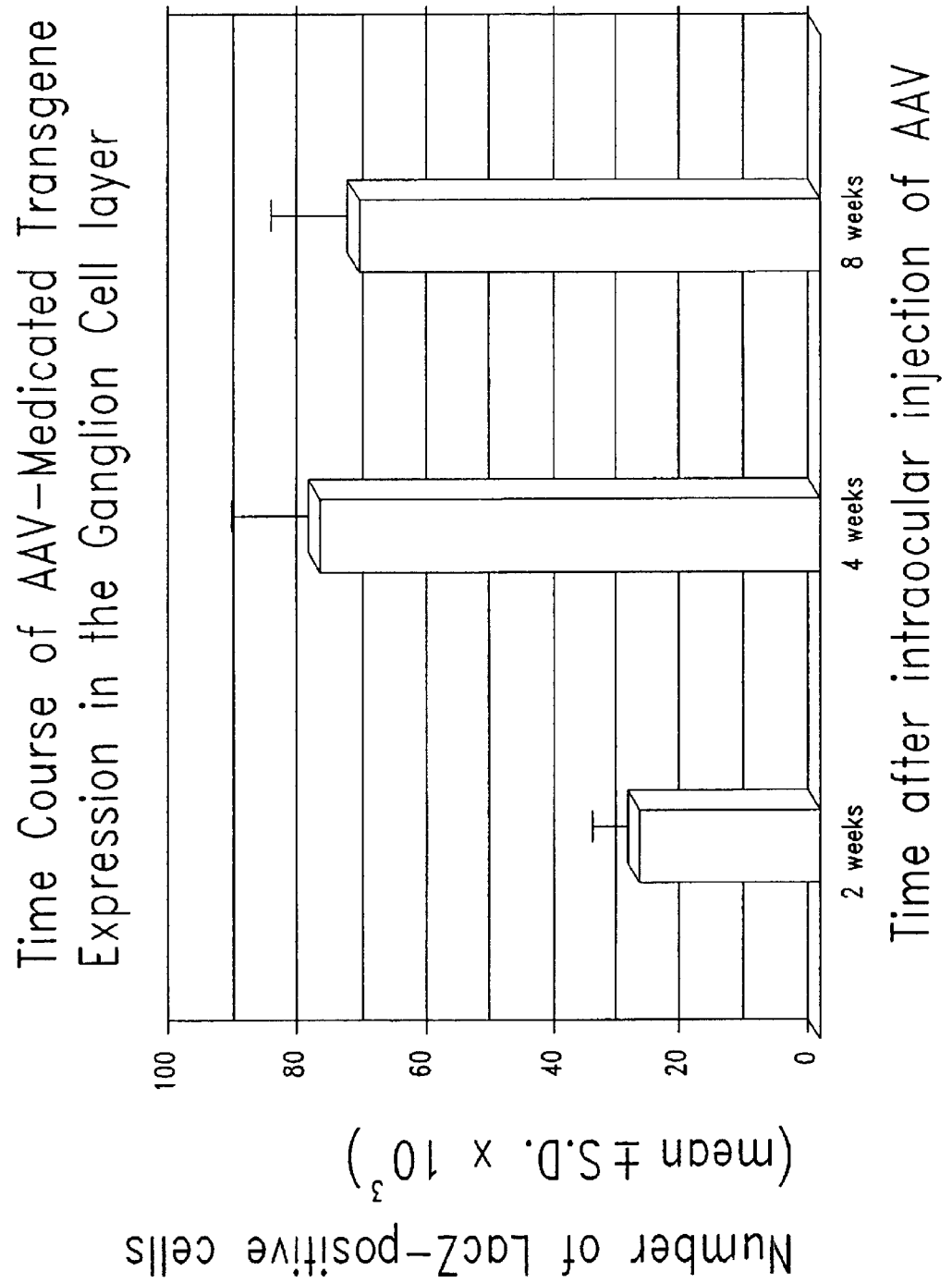
FIG. 17 is a graph which shows the time-course of AAV-mediated transgene expression in the ganglion cell layer of the adult rat retina. A recombinant AAV vector (rAAV-CMV-lacZ) was injected into the vitreous chamber of adult rats and 2, 4 and 8 weeks later, Lac-Z positive neurons in the ganglion cell layer (GCL) were counted in retinal flat-mounts. The values are the mean of 3–4 retinas per time point ± standard deviation (p<0.001).

Quantification of LacZ-positive cells in the GCL of retinal flat-mounts demonstrated a 2.8-fold increase between 2 and 4 weeks after intravitreal injection of the rAAV-CMV-lacZ vector (FIG. 17). For example, it was found that 27,569±7,646 cells/retina (mean±S.D.;n=3) and 79,043±10,321 cells/retina (n=4) expressed the LacZ gene product at 2 and 4 weeks after intraocular administration of the vector, respectively. A comparable number of cells expressing the AAV-mediated transgene at 4 weeks was observed at 8 weeks (70,221±12,500; n=3) following rAAV-CMV-lacZ injection. Although the majority of LacZ-positive cells were observed in the superior hemisphere at 2 weeks after virus administration, there was robust transgene expression throughout the entire retina by 4 and 8 weeks as assessed by quantification of Lac-Z positive cell densities in all retinal quadrants at these time points (FIG. 17).

Figure 18:
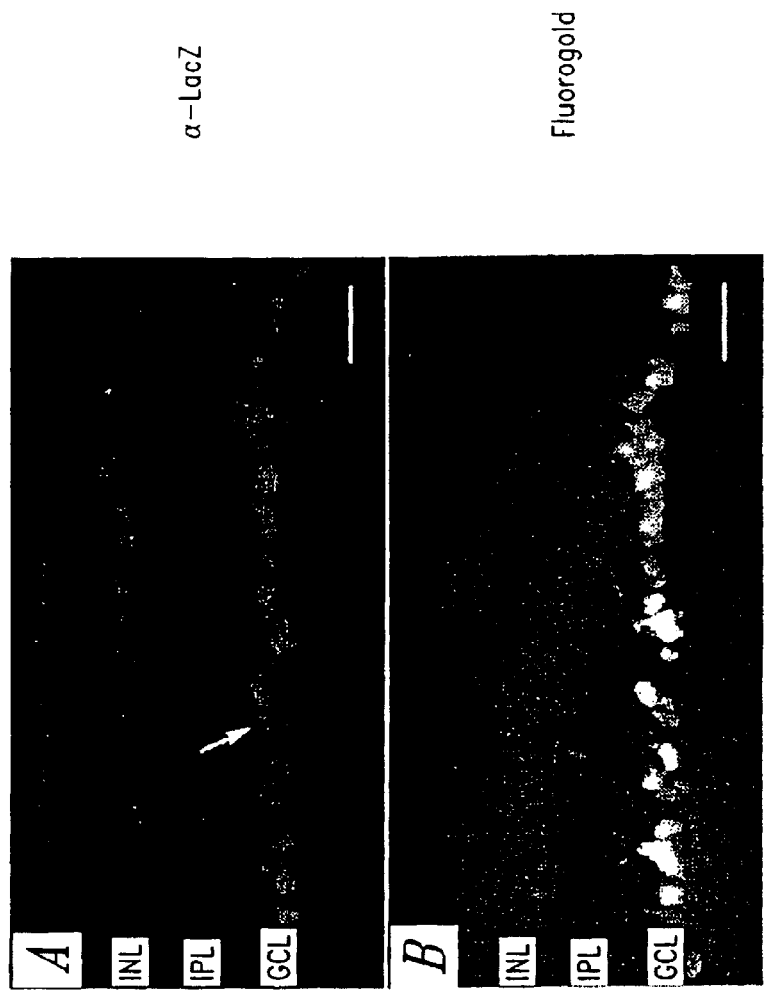
FIGS. 18A and 18B are photographs which show the localization of the AAV mediated LacZ gene product in retrogradely labeled RGCs. a) Retinal radial section showing LacZ immunopositive RGCs transduced with AAV (excitation 520–560, barrier 580, emission 580); b) Same section examined under a different fluorescent filter (excitation 355–425, barrier 460, emission 470) to visualize RGCs backlabeled with Fluorogold from the superior colliculus. Notice that the vast majority of LacZ immunopositive neurons are also labeled with Fluorogold. An exception, a LacZ positive cell that is not Fluorogold labeled, is shown (arrow), and could represent a displaced amacrine cell or RGC that did not incorporate the retrograde tracer. INL: inner nuclear layer, IPL: inner plexiform layer; GCL: ganglion cell layer. Scale bar: 10 $\mu$m.
Figure 19:
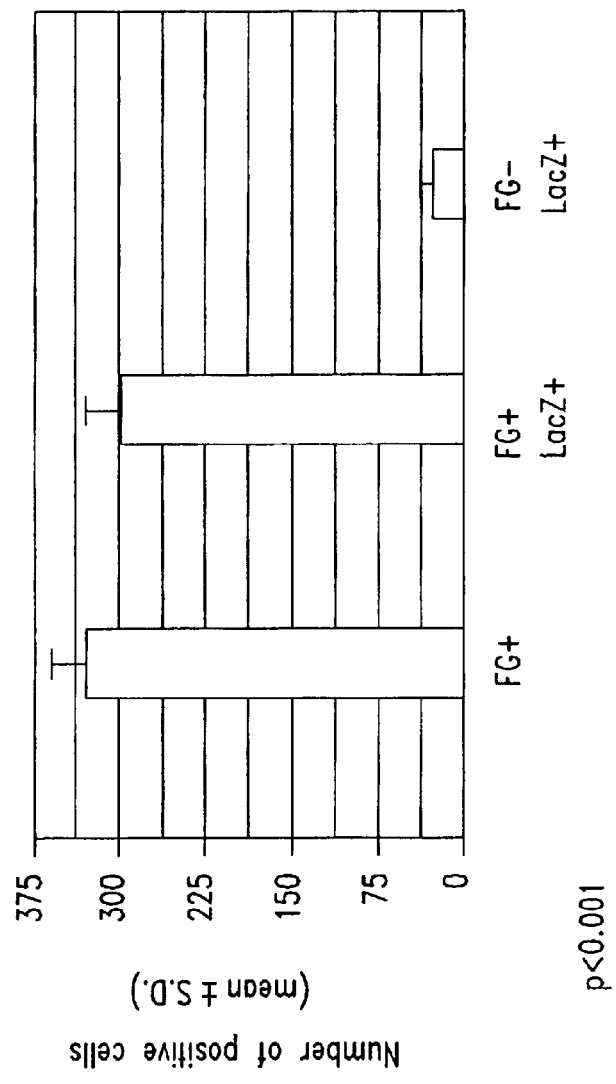
FIG. 19 is a graph which quantifies Fluorogold- and LacZ-positive cells in the ganglion cell layer following intravitreal injection of rAAV-CMV-lacZ. The number of Fluorogold-positive cells (FG+) was compared to the number of cells that expressed both the Fluorogold and LacZ markers (FG+, LacZ+) and the number of cells expressing only the reporter gene (LacZ+). Values represent the mean of 4–5 retinal radial sections per animal (n=4)± standard deviation (S.D.) (p<0.001).

To identify the cellular localization of the AAV-mediated LacZ gene product, immunocytochemical staining of LacZ was combined with retrograde tracing of RGC bodies using Fluorogold backlabeling from the superior colliculi. Double-labeling experiments indicated that the majority of cells in the GCL expressing the LacZ gene product were also Fluorogold-positive (FIG. 18). Analysis of the number of Fluorogold-labeled cells in the GCL expressing the LacZ gene product indicated that 300±29 (mean±S.D.; n=4) expressed both markers out of 330±32 Fluorogold-labeled cells (the average RGC population per retinal radial section). This indicates that ~92% of RGCs, identified by the Fluorogold label, also expressed the AAV-mediated LacZ gene product (FIG. 19). In all retinas examined, it was routinely observed that a number of Lac-Z positive cells that were not labeled with Fluorogold (FIGS. 18 and 19). Thus, it is possible that these cells are displaced amacrine cells or RGCs that failed to incorporate the retrograde tracer. Together, these results indicate that RGCs are preferentially transduced by recombinant AAV following intravitreal injection of this viral vector.

Figure 20:
FIG. 20 is a photograph which shows the localization of the heparan sulfate (HS) proteoglycan receptor, the cellular receptor for AAV, in the intact adult rat retina. Retinal cryosection immunostained with a polyclonal antibody against the heparan sulfate (HepSS-1; diluted 1:200) followed by biotinylated anti-rabbit Fab fragment, avidin-biotin-peroxidase reagent (ABC Elite Vector Labs, Burlingame, Calif.). The section was reacted in a solution containing 0.05% diarninobenzidine tetrahydrochloride (DAB) and 0.06% hydrogen peroxide in PB (pH 7.4) for 5 min. Notice the strong labeling in RGCs in the ganglion cell layer (GCL). RPE: retinal pigment epithelium, PS: photoreceptor segments, ONL: outer nuclear layer, OPL: outer plexiform layer, INL: inner nuclear layer, IPL: inner plexiform layer. Scale bar: 50 $\mu$m.

To investigate the molecular mechanisms underlying preferential transduction of RGCs by AAV, expression of the heparan sulfate proteoglycan (which mediates both AAV attachment and infection of target cells (Summerford et al., 1998)) in the adult retina was observed. Immunostaining of retinal radial sections with a specific antibody against heparan sulfate (HepSS-1) demonstrated robust staining in the GCL (FIG. 20). Positive immunolabeling was clearly visualized in both neuronal somata and axonal bundles in the fiber layer. More diffuse and sparse staining was observed in some photoreceptor nuclei and cells in the inner nuclear layer. No staining was observed in control retinal sections in which the primary antibody was omitted (not shown).

To determine the cell type within the GCL that express the heparan sulfate proteoglycan receptor, a double-labeling study was performed in which RGCs were first retrogradely labeled from the superior colliculi followed by immunostaining of retinal sections with HepSS-1. Our analysis showed that 299±23 (mean±S.D.;n=4) cells in the GCL expressed both Fluorogold and HepSS-1 markers out of 315±34 Fluorogold-labeled cells which represent the average RGC population visualized per retinal radial section. The large population of RGCs (~95%) expressing heparan sulfate proteoglycan receptor correlated well with the number of RGCs expressing the AAV-mediated transgene product (~92%). Together, these data suggest that preferential transduction of adult RGCs by recombinant AAV is mediated by the heparan sulfate proteoglycan receptor expressed by these neurons.

Example 10

Construction of A rAAV Vector Expressing Vascular Endothelial Growth Factor (VEGF) 165

Figure 21:
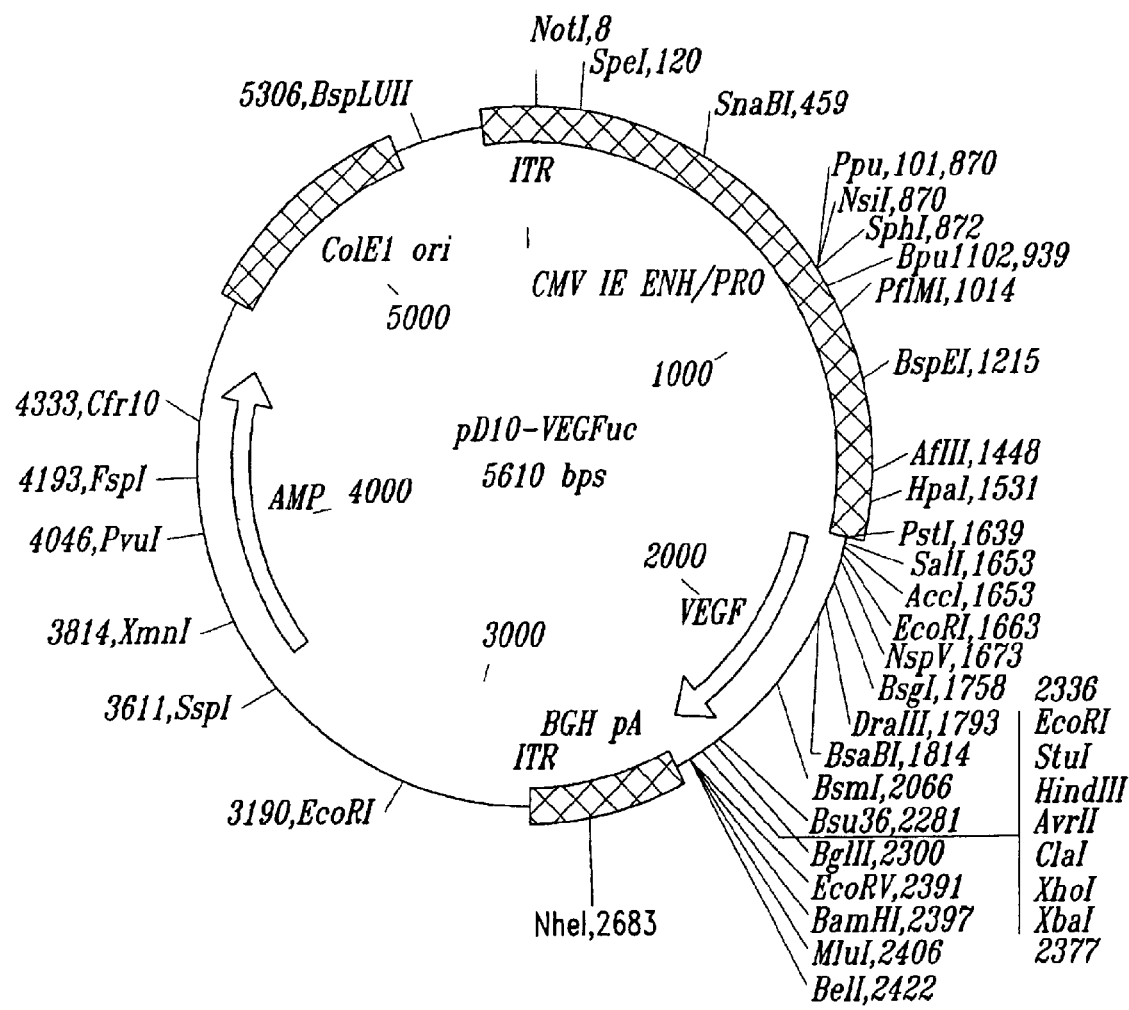
FIG. 21 is a schematic illustration of pD10-VEGFuc.

The human VEGF-165 cDNA was cloned from the PCR-Blunt II Topo Vector (Invitrogen) into the pD10-CMV rAAV vector as an EcoRI fragment (pD10-VEGFuc). The pD10-VEGFuc vector is illustrated schematically in FIG. 21, and its nucleotide sequence is shown in FIG. 22. The VEGFuc rAAV virus was packaged using the triple transfection method and purified by column chromatography.

Briefly, a cell pellet is resuspended in TNM buffer: 20 mM Tris pH 8.0, 150 mM NaCl, 2mM $MgCl_2$. Deoxycholic Acid is added to 0.5% to lyse the cells. 50 u/ml Benzonase is added and the lysed cells are incubated at 37 degrees to digest any nucleic acids. The cell debris is pelleted and the supernatant is filtered through a 0.45 um filter and then a 0.22 um filter. The virus is then loaded onto a 1.5ml Heparin sulfate column using the Biocad. The column is then washed with 20 mM Tris pH 8.0, 100 mM NaCl. The rAAV particles are eluted with a gradient formed with increasing concentrations of NaCl. The fractions under the peak are pooled and filtered through a 0.22 um filter before overnight precipitation with 8% PEG 8000. $CaCl_2$ is added to 25 mM and the purified particles are pelleted and then resuspended in HBS#2: 150 mM NaCl, 50 mM Hepes pH7.4.

Example 11

Infection of 293 Cells with D10-VEGF rAAV Results in VEGF Protein Expression

The functionality of the viral particles was assessed by infection of 293 cells with 3 different viral multiplicities of infection (MOIs); 1×10e7, 1×10e8 and 1×10e9 viral particles per 4×10e5 293 cells, in the presence of 1.5 uM etoposide. At 48 hours post infection, tissue culture media (sups) and cell lysates were harvested. VEGF protein levels were determined using a Quantikine human VEGF sandwich ELISA kit (R and D Systems, see FIG. 23). VEGF protein concentrations are given in pg/ml. The two highest MOIs gave values significantly above that of the cells infected with a negative control virus. The levels of secreted VEGF were approximately 4–7 fold higher than those of the lysates.

Example 12

Figure 24:
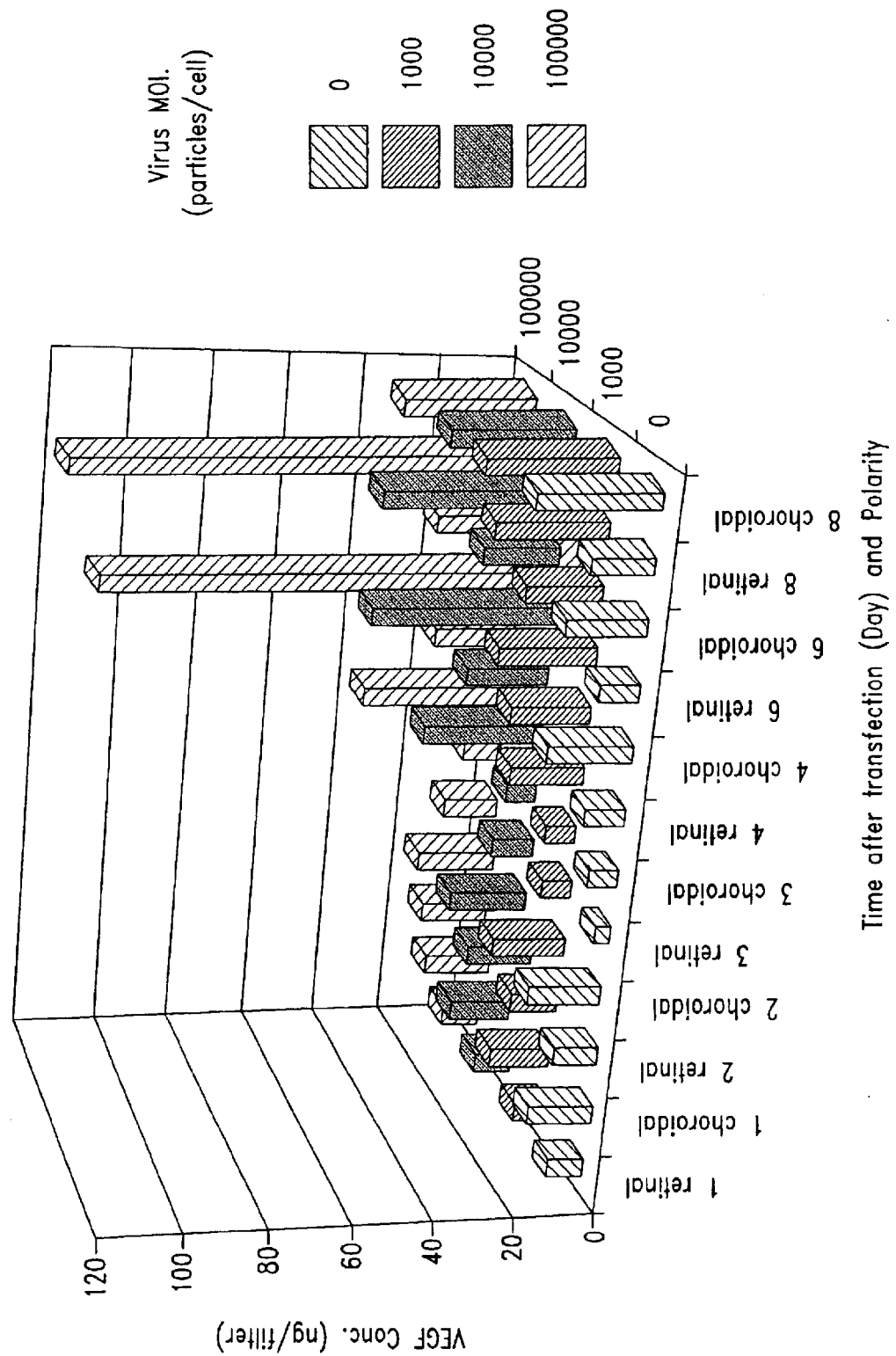
FIG. 24 is a three dimensional bar-graph which shows VEGF secretion by hfRPE after infection with VEGF AAV.

Infection of Retinal Pigment Epithelial (RPE) Cells with D10-VEGF rAAV Results in VEGF Protein Secretion VEGF expression levels in a monolayer of cultured primary (or very early passage) human fetal RPE cells infected with D10-VEGF 165 rAAV were clearly elevated relative to endogenous levels. Cells were infected with a range of rAAV particles from 0 to 1×10e5 per cell. VEGF expression was dose dependent, increased over time, and secretion appeared to be somewhat higher from the apical surface. In a representative experiment, RPE cells infected with 1×10e5 viral particles secreted >100 ng/1×10e6 cells from the apical surface and 50 ng/1×10e6 cells from the basal surface at 8 days post infection. The polarity of VEGF secretion from human fetal RPE cells infected with 3 different MOIs is shown in FIG. 24.

Example 13

Figure 25:
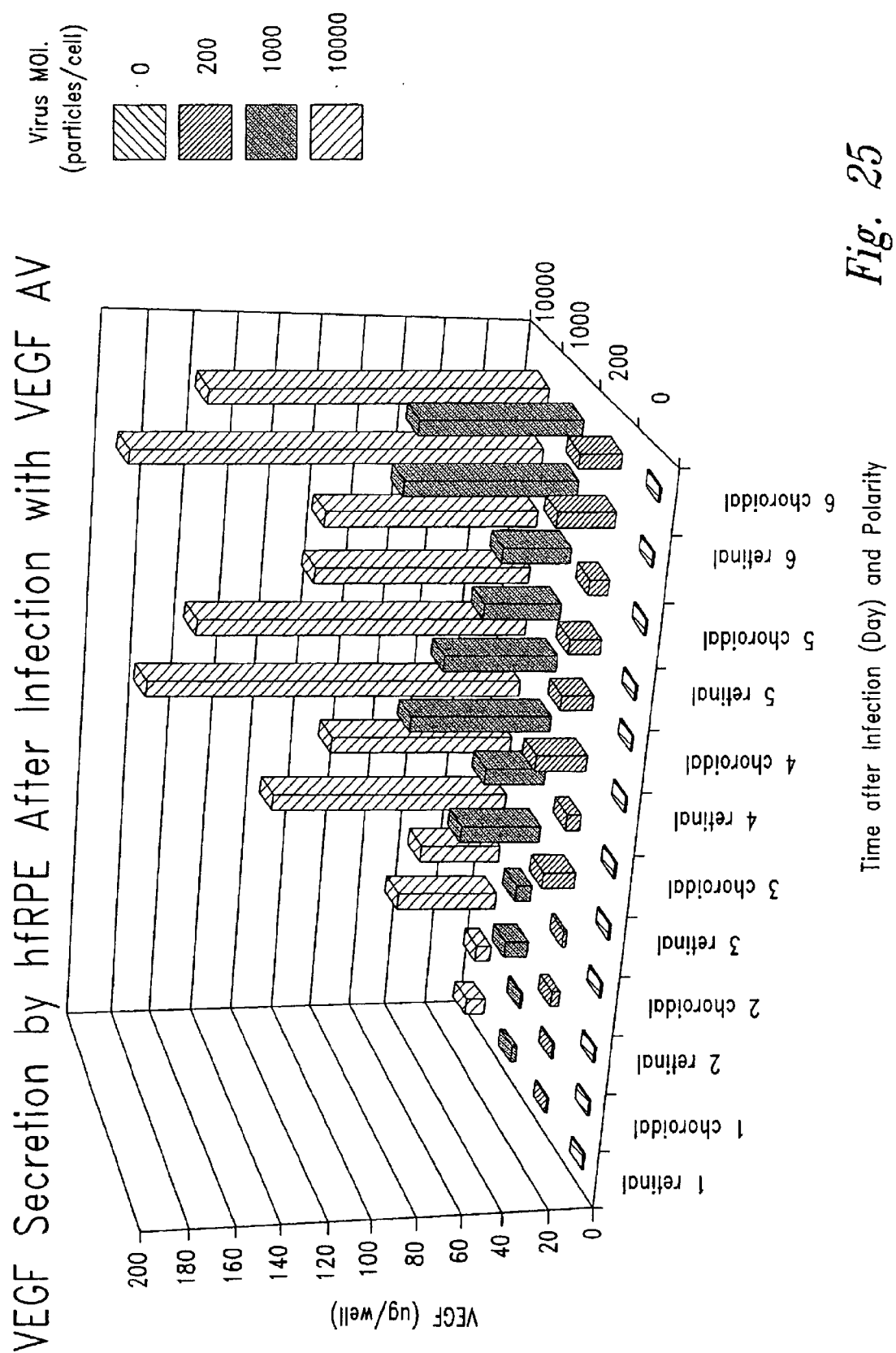
FIG. 25 is a three dimensional bar-graph which shows VEGF secretion by hfRPE after infection with VEGF AV
Figure 26:
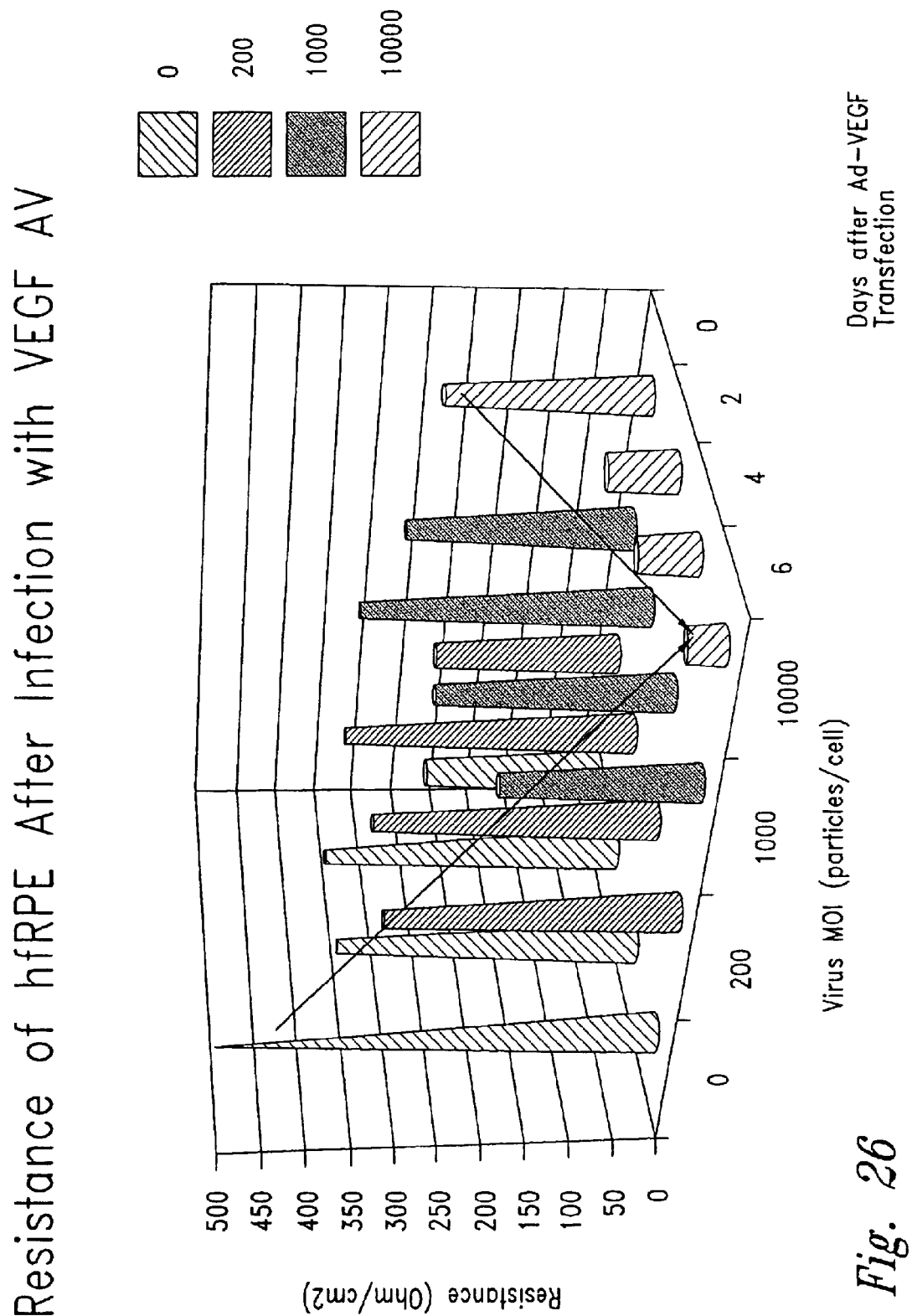
FIG. 26 is a three dimensional bar-graph which shows resistance of hfRPE after infection with VEGF AV.

Infection of Retinal Pigment Epithelial (RPE) Cells with VEGF RAV Results in VEGF Protein Secretion and Decreased Membrane Conductance Infection of cultured human fetal RPE cells with recombinant VEGF adenovirus (AV) results in secretion of very high levels of VEGF from both the apical and basal surfaces of the RPE. MOI's of 0 to 1,000 or 0 to 10,000 particles per cell were used in two separate experiments. In both cases, expression levels increased over time, peaking at approximately 100–200 ug/1×10e6 cells at the highest MOI's (see FIG. 25). In addition, the total transepithelial membrane resistance of the RPE monolayer decreased significantly at all MOIs, and by approximately 4–5 fold at the highest MOIs (see FIG. 26).

Example 14

Construction of A RAAV Vector Expressing Soluble FLT-1 (SFLT-1) Receptor

Figure 27:
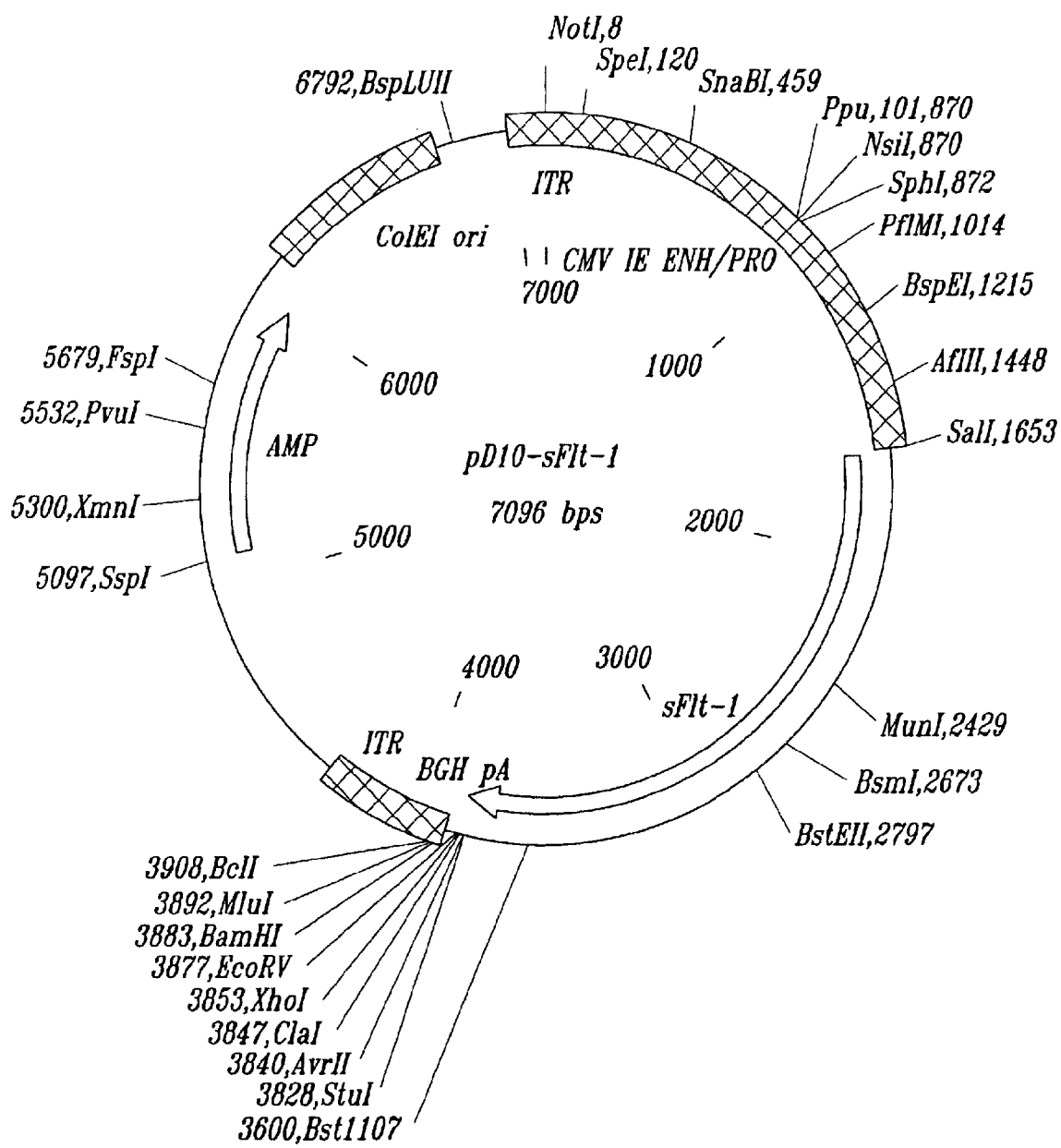
FIG. 27 is a schematic illustration of pD10-sFlt-1.

The sFlt-1 cDNA was cloned from the Blunt II Topo Vector (Invitrogen) into the pD10-CMV rAAV vector as an EcoR1 fragment (pD10-sFlt-1). The pD10-sFlt-1 vector is illustrated schematically in FIG. 27, and its nucleotide sequence is shown in FIG. 28. The human sFlt-1 rAAV virus was packaged using the triple transfection technique and purified by column chromatography.

Example 15

In Vitro Assay for Anti-angiogenic Activity

This example describes the HMVEC (human dermal microvascular endothelial cell) proliferation assay, which can be utilized to determine the anti-angiogenic activity of a molecule by inhibition of VEGF stimulated proliferation (see Kupprion et al., 1998. JBC 273:29635–29640).

Briefly, HMVEC cells obtained from Clonetics (catalog #2543), are seeded in a 96 well culture dish at a density of 2,000 cells per well in 100 ul assay media and incubated at 37° C. for 3–5 hours. The assay media is EBM media, or endothelial basal media (Clonetics, catalog # CC-3121) containing 5% FBS and 1% pen/strep. Dilutions of anti-angiogenic samples are added in triplicate (50 ul each, for final well volume of 200 ul), immediately followed by 50 ul 20 ng/ml recombinant VEGF (R and D Systems, final concentration 5 ng/ml, or 0.1 nM). The samples are conditioned media from 293 cells transiently transfected with a pD10 rAAV plasmid, by standard methods, or from 293 cells infected with an rAAV virus. Culture media is collected from 24–48 hours post-transfection or post-infection. After the addition of sample and recombinant VEGF, the cells are incubated for 48 hours at 37° C., when they are pulsed with 1 uCi/well $^3$H-thymidine (Amersham, catalog # TRK300). The stock of 1 mCi/ml $^3$H-thymidine is diluted 1:10 in assay media, and 10 ul added per well. The cells are incubated for an additional 18 hours, at which point 100 ul media is removed and the cells are lysed by the addition of 40 ul of 1M NaOH per well. Finally, the cells are harvested with a Tomtec Harvestor, transferred to Filtermat paper (Wallac), 10 ml of scintillation fluid added and the incorporation of $^3$H-thymidine determined by scintillation counting.

Figure 34:
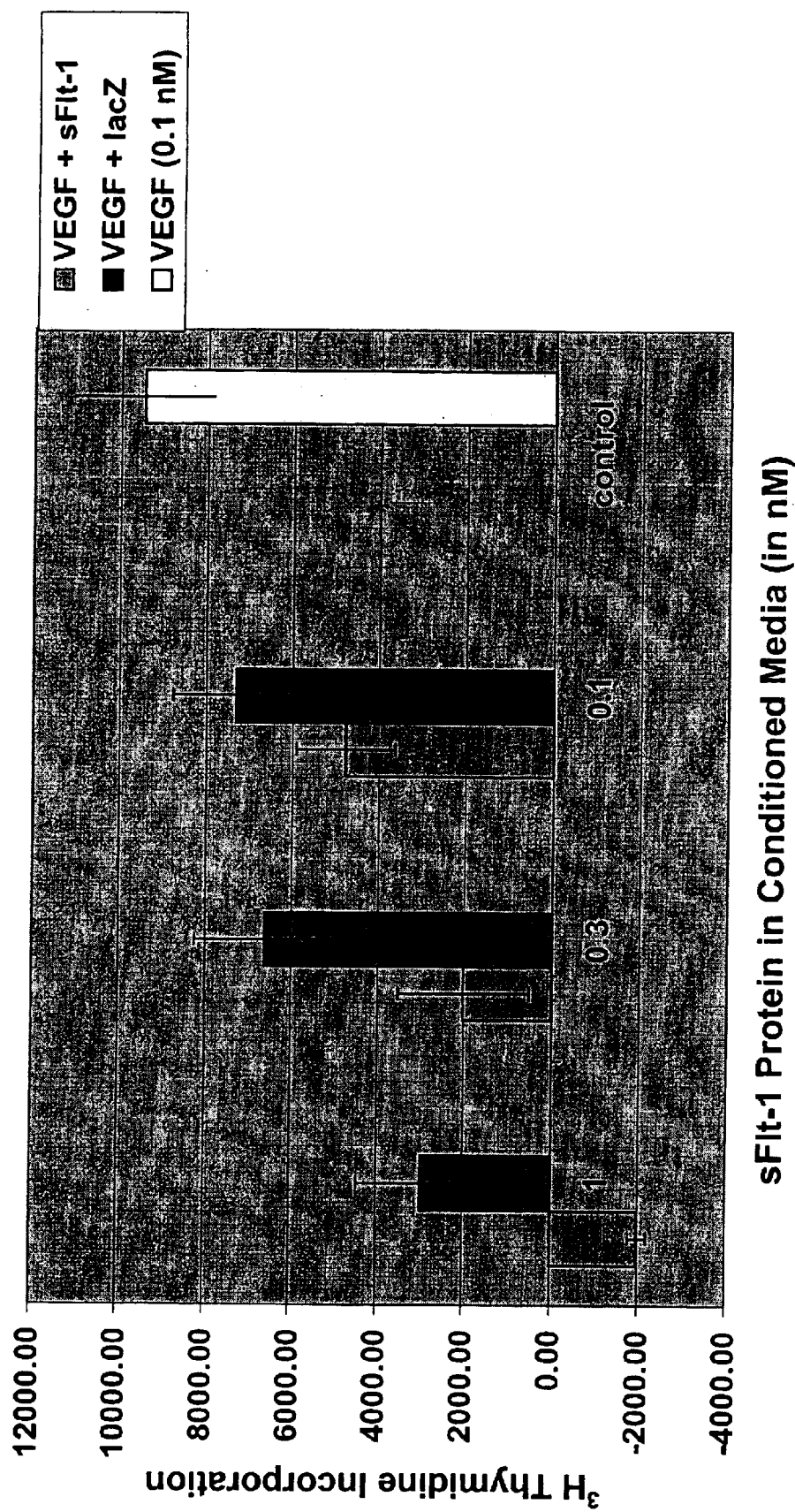
FIG. 34 is a bar graph that shows inhibition of HMVEC proliferation by sFlt-1 rAAV.

Inhibition of HMVEC proliferation by conditioned media from sFlt-1 rAAV infected 293 cells is shown in FIG. 34. Complete inhibition of proliferation (induced by 0.1 nM VEGF) was observed at approximately at 1 nM sFlt-1, and partial inhibition at approximately 0.3 nM and 0.1 nM sFlt-1 protein. This inhibition was not seen with HMVEC cells treated with conditioned media from lacZ rAAV infected cells, or cells treated with recombinant VEGF alone. To generate conditioned media, 4×10e5 293 cells were infected with 1×10e11 total particles sFlt-1 rAAV or a CMV-lacZ control rAAV. If one assumes an infectious particle ratio of 1:1,000 to 1:10,000, this is an MOI of less than or equal to 2.5×10e2 per cell. All samples were run in triplicate, and means and standard deviations are shown. Background incorporation of $^3$H-thymidine in cells not stimulated with exogenous VEGF was subtracted from all samples, leading to a negative value in one case. The total amount of sFlt-1 protein in the conditioned media was determined by a sandwich Elisa (antibodies purchased from R and D Systems).

Example 16

Animal Model for Neovascularization by Subretinal Injection of VEGF RAAV

This example describes an animal model that, after subretinal injection of a recombinant virus (rAAV) containing an angiogenic transgene (VEGF), generates subretinal neovascularization and choroidal neovascularization. As noted above, choroidal neovascularization is a hallmark of exudative or wet Age-related Macular Degeneration (AMD), the leading cause of blindness in the elderly population. Retinal neovascularization occurs in diseases such as diabetic retinopathy and retinopathy of prematurity (ROP), the most common cause of blindness in the young.

Briefly, subretinal injections of 2 µl AAV-VEGF (titer: $5.8 \times 10^{13}$ particles/ml) were made in a bleb under the retina just outside the apical membrane of the RPE. These injections were made 3–3.5 months before the animals were sacrificed. After sacrifice animals were examined for the extent and duration of neovascularization induced by rAAV vectors using fundus photography, fluorescein angiography (FIG. 35), histology (FIG. 36), and immunochemistry (FIG. 37). As described in more detail below, these figures demonstrate in three different ways that AAV mediated overexpression of VEGF in the RPE can generate choroidal neovascularization.

More specifically, FIG. 35A is an image of the fundus showing retinal blood vessels from a live animal before it was sacrificed for the serial sectioning shown in FIG. 36. Note that the blood vessels are larger in diameter in the AAV-VEGF injected area (black arrow). FIG. 35B, is a fluorescein angiogram from the same animal taken shortly after the fundus image in 35A. Two minutes after fluorescein injection (intramuscular) significant leakage of fluorescein was observed at the AAV-VEGF injection site (black arrows).

FIG. 36 (panels A–D) are a series of epoxy sections taken after sacrifice of the animal. FIG. 36A is a section taken from half of the eye furthest from AAV-VEGF injection site, showing normal photoreceptors and blood vessels (the arrow points to photoreceptors with normal morphology). Moving from this section toward the AAV-VEGF injection site, monotonically increasing photoreceptor disorganization and new blood vessel formation was observed (data not shown).

FIGS. 36B and C are epoxy sections from the AAV-VEGF injection site. The short arrows show new blood vessel growth and the long arrows show a pathologically disorganized photoreceptor layer. FIG. 36D is also an epoxy section from the AAV-VEGF injection site. The arrow points to a blood vessel breaking through Bruch's Membrane, probably from the choroid.

FIGS. 37(A–D) show lectin/BrdU double-staining of rat retina (A–B) and choroid (C–D). Green staining is the lectin staining of endothelial cells, and red staining is BrdU staining of dividing cells. Green cells with red dots are dividing endothelial cells, which are part of the newly formed blood vessels.

More specifically, FIG. 37A is an image of the at the AAV-VEGF injection site showing extensive BrdU staining. Note that there are many more blood vessels compared to that seen at points distant from the AAV-VEGF injection site in panel B. The lectin staining is fuzzy because the blood vessels are bloated with dividing endothelial cells. FIG. 37B is an image of the retina furthest from the AAV-VEGF injection site. This image shows minimal BrdU staining. In contrast, lectin staining is clear and sharply defined. FIG. 37C is an image of the choroids at the AAV-VEGF injection site, which also shows extensive BrdU staining. The lectin image is not shown since it binds indiscriminately throughout choroid and sclera. FIG. 37D is an image of the choroids furthest from the AAV-VEGF injection site, and shows minimal BrdU staining.

Example 17

Injection of Therapeutic Anti-angiogenic RAAV Into an Animal Model for Ocular Neovascularization This example demonstrates the ability of anti-angiogenic molecules to prevent neovascularization in the rat model described above. Briefly, in four animals rAAV-sFlt-1 or rAAV-PEDF were injected together with rAAV-VEGF into the subretinal space of one eye; the contralateral eye received an injection of rAAV-VEGF and rAAV-GFP. Six weeks after injection, electroretinographic analysis (ERGs) were obtained from both eyes of each animals simultaneously. The a- or b- wave amplitude from the test eye (AAV-VEGF+AAV-sFlt) is designated as $A_t$, or $B_t$. The a- or b- wave amplitude from the control eye (AAV-VEGF+AAV-GFP) is designated as $A_c$, or $B_c$, respectively. In each eye ERG a- and b- waves were measured and for each animal the amplitude ratio was calculated as percent change in the test eye relative to the control eye:

$$ERG \text{ Amplitude Ratio} = (A_t - A_c)/A_c \text{ or } (B_t - B_c)/B_c$$

The amplitude ratio for a- and b- waves are plotted in FIG. 38. Briefly, significant functional rescue was obtained in three/four animals using sFlt-1 and two/four animals using PEDF. FIG. 39 shows comparison ERGs of test and control eye of sFlt-1 treated rats. The dark-solid line shows that the eye rescued with sFlt-1 has a- and b- wave amplitudes approximately twice as large as the control eye (light-dashed line). This data indicates that sFlt-1 or PEDF can be used to rescue retinal function that is lost during neovascularization.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of inhibiting angiogenesis in a diseased eye of a subject, comprising, administering intraocularly a recombinant adeno-associated virus (rAAV) gene delivery vector which directs the expression of an anti angiogenic factor, such that administration of said vector inhibits neovascularization of the diseased eye.

2. The method according to claim 1 wherein said anti-angiogenic factor is soluble Flt-1, PEDF, soluble Tie-2 receptor, or a single chain anti-VEGF antibody.

3. The method according to claim 1 wherein said diseased eye is in a subject having diabetic retinopathy, wet AMD or retinopathy of prematurity.

* * * * *

SEQUENCE LISTING

<160> NUMBER OF SEQ ID NOS: 12

<210> SEQ ID NO 1
<211> LENGTH: 6514
<212> TYPE: DNA
<213> ORGANISM: Homo sapien

<400> SEQUENCE: 1

| | | | | | |
|---|---|---|---|---|---|
| accatgtagc | ggccctgcgc | gctcgctcgc | tcactgaggc | cgcccgggca | aagcccgggc | 60 |
| gtcgggcgac | ctttggtcgc | ccggcctcag | tgagcgagcg | agcgcgcaga | gagggagtgg | 120 |
| ccaactccat | cactagggt | tccttgtagt | taatgattaa | cccgccatgc | tacttatcta | 180 |
| cgtagccatg | ctctagggaa | ttggccgcgg | aatttcgact | ctaggccatt | gcatacgttg | 240 |
| tatctatatc | ataatatgta | catttatatt | ggctcatgtc | caatatgacc | gccatgttga | 300 |
| cattgattat | tgactagtta | ttaatagtaa | tcaattacgg | ggtcattagt | tcatagccca | 360 |
| tatatggagt | tccgcgttac | ataacttacg | gtaaatggcc | cgcctggctg | accgcccaac | 420 |
| gacccccgcc | cattgacgtc | aataatgacg | tatgttccca | tagtaacgcc | aatagggact | 480 |
| ttccattgac | gtcaatgggt | ggagtattta | cggtaaactg | cccacttggc | agtacatcaa | 540 |
| gtgtatcata | tgccaagtcc | gcccctatt | gacgtcaatg | acggtaaatg | gcccgcctgg | 600 |
| cattatgccc | agtacatgac | cttacgggac | tttcctactt | ggcagtacat | ctacgtatta | 660 |
| gtcatcgcta | ttaccatggt | gatgcggttt | tggcagtaca | ccaatgggcg | tggatagcgg | 720 |
| tttgactcac | ggggatttcc | aagtctccac | cccattgacg | tcaatgggag | tttgttttgg | 780 |
| caccaaaatc | aacgggactt | tccaaaatgt | cgtaataacc | ccgccccgtt | gacgcaaatg | 840 |
| ggcggtaggc | gtgtacggtg | ggaggtctat | ataagcagag | ctcgtttagt | gaaccgtcag | 900 |
| atcgcctgga | gacgccatcc | acgctgtttt | gacctccata | gaagacaccg | ggaccgatcc | 960 |
| agcctccgcg | gccgggaacg | gtgcattgga | acgcggattc | cccgtgccaa | gagtgacgta | 1020 |
| agtaccgcct | atagactcta | taggcacacc | cctttggctc | ttatgcatgc | tatactgttt | 1080 |
| ttggcttggg | gcctatacac | ccccgctcct | tatgctatag | gtgatggtat | agcttagcct | 1140 |
| ataggtgtgg | gttattgacc | attattgacc | actcccctat | tggtgacgat | actttccatt | 1200 |
| actaatccat | aacatggctc | tttgccacaa | ctatctctat | tggctatatg | ccaatactct | 1260 |
| gtccttcaga | gactgacacg | gactctgtat | ttttacagga | tggggtccat | ttattattta | 1320 |
| caaattcaca | tatacaacaa | cgccgtcccc | cgtgcccgca | gtttttatta | aacatagcgt | 1380 |
| gggatctccg | acatctcggg | tacgtgttcc | ggacatgggc | tcttctccgg | tagcggcgga | 1440 |
| gcttccacat | ccgagccctg | gtcccatccg | tccagcggct | catggtcgct | cggcagctcc | 1500 |
| ttgctcctaa | cagtggaggc | cagacttagg | cacagcacaa | tgcccaccac | caccagtgtg | 1560 |
| ccgcacaagg | ccgtggcggt | agggtatgtg | tctgaaaatg | agctcggaga | ttgggctcgc | 1620 |
| acctggacgc | agatggaaga | cttaaggcag | cggcagaaga | agatgcaggc | agctgagttg | 1680 |
| ttgtattctg | ataagagtca | gaggtaactc | ccgttcgcgt | gctgttaacg | gtggagggca | 1740 |
| gtgtagtctg | agcagtactc | gttgctgccg | cgcgcgccac | cagacataat | agctgacaga | 1800 |
| ctaacagact | gttcctttcc | atgggtcttt | tctgcagtca | ccgtcgtcga | cctaagaatt | 1860 |
| caggcctaag | cttcctaggt | atcgatctcg | agcaagtcta | gagggagacc | acaacggttt | 1920 |
| ccctctagcg | ggatcaattc | cgcccccccc | cctaacgtta | ctggccgaag | ccgcttggaa | 1980 |
| taaggccggt | gtgcgtttgt | ctatatgtta | ttttccacca | tattgccgtc | ttttggcaat | 2040 |

```
gtgagggccc ggaaacctgg ccctgtcttc ttgacgagca ttcctagggg tctttcccct    2100
ctcgccaaag gaatgcaagg tctgttgaat gtcgtgaagg aagcagttcc tctggaagct    2160
tcttgaagac aaacaacgtc tgtagcgacc ctttgcaggc agcggaaccc cccacctggc    2220
gacaggtgcc tctgcggcca aaagccacgt gtataagata cacctgcaaa ggcggcacaa    2280
ccccagtgcc acgttgtgag ttggatagtt gtggaaagag tcaaatggct ctcctcaagc    2340
gtattcaaca aggggctgaa ggatgcccag aaggtacccc attgtatggg atctgatctg    2400
gggcctcggt gcacatgctt tacatgtgtt tagtcgaggt taaaaaaacg tctaggcccc    2460
ccgaaccacg gggacgtggt tttcctttga aaaacacgat aataccatgg ccgccgggag    2520
catcaccacg ctgccagccc tgccggagga cggcggcagc ggcgctttcc cgccgggcca    2580
cttcaaggac cccaagcggc tgtactgcaa gaacggggc ttcttcctgc gcatccaccc    2640
cgacggccga gtggacgggg tccgcgagaa gagcgaccca cacatcaaac tacaacttca    2700
agcagaagag agagggttg tgtctatcaa aggagtgtgt gcaaaccgtt accttgctat    2760
gaaagaagat ggaagattac tagcttctaa atgtgttaca gacgagtgtt ctttttttga    2820
acgattggag tctaataact acaatactta ccggtcaagg aaatacacca gttggtatgt    2880
ggcactgaaa cgaactgggc agtataaact tggatccaaa acaggacctg gcagaaagc    2940 tatactttt cttccaatgt ctgctaagag ctgatcttaa tggcagcatc tgatctcatt    3000
ttacatgaag ctggtggcat ccctgtgacc cctccccagt gcctctcctg gccctggaag    3060
ttgccactcc agtgcccacc agccttgtcc taataaaatt aagttgcatc attttgtctg    3120
actaggtgtc cttctataat attatggggt ggagggggt ggtatggagc aaggggcaag    3180
ttgggaagac aacctgtagg gcctgcgggg tctattggga accaagctgg agtgcagtgg    3240
cacaatcttg gctcactgca atctccgcct cctgggttca agcgattctc ctgcctcagc    3300
ctcccgagtt gttgggattc caggcatgca tgaccaggct cagctaattt ttgttttttt    3360
ggtagagacg gggtttcacc atattggcca ggctggtctc caactcctaa tctcaggtga    3420
tctacccacc ttggcctccc aaattgctgg gattacaggc gtgaaccact gctcccttcc    3480
ctgtccttct gattttaaaa taactatacc agcaggagga cgtccagaca cagcataggc    3540
tacctggcca tgcccaaccg gtgggacatt tgagttgctt gcttggcact gtcctctcat    3600
gcgttgggtc cactcagtag atgcctgttg aattatcgga tccactacgc gttagagctc    3660
gctgatcagc ctcgactgtg ccttctagtt gccagccatc tgttgtttgc ccctcccccg    3720
tgccttcctt gaccctggaa ggtgccactc ccactgtcct ttcctaataa aatgaggaaa    3780
ttgcatcgca ttgtctgagt aggtgtcatt ctattctggg gggtggggtg gggcaggaca    3840 gcaagggga ggattgggaa gacaatagca ggggggtggg cgaagaactc cagcatgaga    3900
tccccgcgct ggaggatcat ccagccaatt ccctagagca tggctacgta gataagtagc    3960
atggcgggtt aatcattaac tacaaggaac ccctagtgat ggagttggcc actccctctc    4020
tgcgcgctcg ctcgctcact gaggccgggc gaccaaaggt cgcccgacgc ccgggctttg    4080
cccgggcggc ctcagtgagc gagcgagcgc gcagggggtg ggcgaagaac tccagcatga    4140
gatccccgcg ctgaggatc atccagccgg cgtcccggaa aacgattccg aagcccaacc    4200
tttcatagaa ggcggcggtg gaatcgaaat ctcgtgatgg caggttgggc gtcgcttggt    4260
cggtcatttc gaaccccaga gtcccgctca agaactcg tcaagaaggc gatagaaggc    4320
gatgcgctgc gaatcgggag cggcgatacc gtaaagcacg aggaagcggt cagcccattc    4380
```

```
gccgccaagc tcttcagcaa tatcacgggt agccaacgct atgtcctgat agcggtccgc    4440
cacacccagc cggccacagt cgatgaatcc agaaaagcgg ccattttcca ccatgatatt    4500
cggcaagcag gcatcgccat gggtcacgac gagatcctcg ccgtcgggca tgcgcgcctt    4560
gagcctggcg aacagttcgg ctggcgcgag cccctgatgc tcttcgtcca gatcatcctg    4620
atcgacaaga ccggcttcca tccgagtacg tgctcgctcg atgcgatgtt tcgcttggtg    4680
gtcgaatggg caggtagccg gatcaagcgt atgcagccgc cgcattgcat cagccatgat    4740
ggatactttc tcggcaggag caaggtgaga tgacaggaga tcctgccccg gcacttcgcc    4800
caatagcagc cagtcccttc ccgcttcagt gacaacgtcg agcacagctg cgcaaggaac    4860
gcccgtcgtg gccagccacg atagccgcgc tgcctcgtcc tgcagttcat tcagggcacc    4920
ggacaggtcg gtcttgacaa aaagaaccgg gcgcccctgc gctgacagcc ggaacacggc    4980
ggcatcagag cagccgattg tctgttgtgc ccagtcatag ccgaatagcc tctccaccca    5040
agcggccgga gaacctgcgt gcaatccatc ttgttcaatc atgcgaaacg atcctcatcc    5100
tgtctcttga tcagatcttg atccctgcg ccatcagatc cttggcggca agaaagccat    5160
ccagtttact ttgcagggct tcccaacctt accagagggc gccccagctg caattccgg    5220 ttcgcttgct gtccataaaa ccgcccagtc tagctatcgc catgtaagcc cactgcaagc    5280
tacctgcttt ctctttgcgc ttgcgttttc ccttgtccag atagcccagt agctgacatt    5340
catccggggt cagcaccgtt tctgcggact ggctttctac gtgttccgct tcctttagca    5400
gcccttgcgc cctgagtgct tgcggcagcg tgaagctgtc aattccgcgt taaatttttg    5460
ttaaatcagc tcattttta accaataggc cgaaatcggc aaaatccctt ataaatcaaa    5520
agaatagccc gagataggt tgagtgttgt tccagtttgg aacaagagtc cactattaaa    5580
gaacgtggac tccaacgtca aagggcgaaa accgtctat cagggcgatg gcggatcagc    5640
ttatgcggtg tgaaataccg cacagatgcg taaggagaaa ataccgcatc aggcgctctt    5700
ccgcttcctc gctcactgac tcgctgcgct cggtcgttcg gctgcggcga gcggtatcag    5760
ctcactcaaa ggcggtaata cggttatcca cagaatcagg ggataacgca ggaaagaaca    5820
tgtgagcaaa aggccagcaa aaggccagga accgtaaaaa ggccgcgttg ctggcgtttt    5880
tccataggct ccgccccct gacgagcatc acaaaaatcg acgctcaagt cagaggtggc    5940
gaaacccgac aggactataa agataccagg cgtttccccc tggaagctcc ctcgtgcgct    6000
ctcctgttcc gaccctgccg cttaccggat acctgtccgc ctttctccct tcgggaagcg    6060
tggcgctttc tcatagctca cgctgtaggt atctcagttc ggtgtaggtc gttcgctcca    6120
agctgggctg tgtgcacgaa ccccccgttc agcccgaccg ctgcgcctta tccggtaact    6180
atcgtcttga gtccaacccg gtaagacacg acttatcgcc actggcagca gccactggta    6240
acaggattag cagagcgagg tatgtaggcg gtgctacaga gttcttgaag tggtggccta    6300
actacggcta cactagaagg acagtatttg gtatctgcgc tctgctgaag ccagttacct    6360
tcggaaaaag agttggtagc tcttgatccg gcaaacaaac caccgctggt agcggcggtt    6420
ttttgtttgc aagcagcaga ttacgcgcag aaaaaaagga tctcaagaag atcctttgat    6480
cttttcttac tgaacggtga tccccaccgg aatt                                6514
```

<210> SEQ ID NO 2
<211> LENGTH: 5610
<212> TYPE: DNA
<213> ORGANISM: Homo sapien

<400> SEQUENCE: 2

-continued

| | | | | |
|---|---|---|---|---|
| aaaacttgcg | gccgcggaat | ttcgactcta | ggccattgca | tacgttgtat | ctatatcata | 60 |
| atatgtacat | ttatattggc | tcatgtccaa | tatgaccgcc | atgttgacat | tgattattga | 120 |
| ctagttatta | atagtaatca | attacggggt | cattagttca | tagcccatat | atggagttcc | 180 |
| gcgttacata | acttacggta | aatggcccgc | ctggctgacc | gcccaacgac | ccccgcccat | 240 |
| tgacgtcaat | aatgacgtat | gttcccatag | taacgccaat | agggactttc | cattgacgtc | 300 |
| aatggGtgga | gtatttacgg | taaactgccc | acttggcagt | acatcaagtg | tatcatatgc | 360 |
| caagtccgcc | ccctattgac | gtcaatgacg | gtaaatggcc | cgcctggcat | tatgcccagt | 420 |
| acatgacctt | acgggacttt | cctacttggc | agtacatcta | cgtattagtc | atcgctatta | 480 |
| ccatggtgat | gcggttttgg | cagtacacca | atgggcgtgg | atagcggttt | gactcacggg | 540 |
| gatttccaag | tctccacccc | attgacgtca | atgggagttt | gttttggcac | caaaatcaac | 600 |
| gggactttcc | aaaatgtcgt | aatAaccccg | cccgttgac | gcaaatgggc | ggtaggcgtg | 660 |
| tacggtggga | ggtctatata | agcagagctc | gtttagtgaa | ccgtcagatc | gcctggagac | 720 |
| gccatccacg | ctgttttgac | ctccatagaa | gacaccggga | ccgatccagc | ctccgcggcc | 780 |
| gggaacggtg | cattggaacg | cggattcccc | gtgccaagag | tgacgtaagt | accgcctata | 840 |
| gactctatag | gcacaccct | ttggctctta | tgcatgctat | actgtttttg | gcttggggcc | 900 |
| tatacacccc | cgctccttat | gctataggtg | atggtatagc | ttagcctata | ggtgtgggtt | 960 |
| attgaccatt | attgaccact | cccctattgg | tgacgatact | ttccattact | aatccataac | 1020 |
| atggctcttt | gccacaacta | tctctattgg | ctatatgcca | atactctgtc | cttcagagac | 1080 |
| tgacacggac | tctgtatttt | tacaggatgg | ggtccattta | ttatttacaa | attcacatat | 1140 |
| acaacaacgc | cgtcccccgt | gcccgcagtt | tttattaaac | atagcgtggg | atctccgaca | 1200 |
| tctcgggtac | gtgttccgga | catgggctct | tctccggtag | cggcggagct | tccacatccg | 1260 |
| agccctggtc | ccatccgtcc | agcggctcat | ggtcgctcgg | cagctccttg | ctcctaacag | 1320 |
| tggaggccag | acttaggcac | agcacaatgc | ccaccaccac | cagtgtgccg | cacaaggccg | 1380 |
| tggcggtagg | gtatgtgtct | gaaaatgagc | tcggagattg | ggctcgcacc | tggacgagga | 1440 |
| tggaagactt | aaggcagcgg | cagaagaaga | tgcaggcagc | tgagttgttg | tattctgata | 1500 |
| agagtcagag | gtaactcccg | ttgcggtgct | gttaacggtg | gagggcagtg | tagtctgagc | 1560 |
| agtactcgtt | gctgccgcgc | gcgccaccag | acataatagc | tgacagacta | acagactgtt | 1620 |
| cctttccatg | ggtcttttct | gcagtcaccg | tcgtcgacct | aagaattcgc | ccttcgaaac | 1680 |
| catgaacttt | ctgctgtctt | gggtgcattg | gagccttgcc | ttgctgctct | acctccacca | 1740 |
| tgccaagtgg | tccaggctg | cacccatggc | agaaggagga | gggcagaatc | atcacgaagt | 1800 |
| ggtgaagttc | atggatgtct | atcagcgcag | ctactgccat | ccaatcgaga | ccctggtgga | 1860 |
| catcttccag | gagtaccctg | atgagatcga | gtacatcttc | aagccatcct | gtgtgcccct | 1920 |
| gatgcgatgc | gggggctgct | gcaatgacga | gggcctggag | tgtgtgccca | ctgaggagtc | 1980 |
| caacatcacc | atgcagatta | tgcggatcaa | acctcaccaa | ggccagcaca | taggagagat | 2040 |
| gagcttccta | cagcacaaca | aatgtgaatg | cagaccaaag | aaagatagag | caagacaaga | 2100 |
| aaatccctgt | gggccttgct | cagagcggag | aaagcatttg | tttgtacaag | atccgcagac | 2160 |
| gtgtaaatgt | tcctgcaaaa | acacagactc | gcgttgcaag | gcgaggcagc | ttgagttaaa | 2220 |
| cgaacgtact | tgcagatgtg | acaagccgag | gcggtgagcc | gggcaggagg | aaggagcctc | 2280 |
| cctcagggtt | tcgggaacca | gatctctcac | caggaaagac | tgatacagaa | agggcgaatt | 2340 |

-continued

```
caggcctaag cttcctaggt atcgatctcg agcaagtcta gaaagccatg gatatcggat      2400
ccactacgcg ttagagctcg ctgatcagcc tcgactgtgc cttctagttg ccagccatct      2460
gttgtttgcc cctcccccgt gccttccttg accctggaag gtgccactcc cactgtcctt      2520
tcctaataaa atgaggaaat tgcatcgcat tgtctgagta ggtgtcattc tattctgggg      2580
ggtggggtgg ggcaggacag caaggggag gattgggaag acaatagcag ggggtgggc       2640 gaagaactcc agcatgagat ccccgcgctg gaggatcatc cagctagcaa gtcccatcag      2700
tgatggagtt ggccactccc tctctgcgcg ctcgctcgct cactgaggcc gggcgaccaa      2760
aggtcgcccg acgcccgggc tttgcccggg cggcctcagt gagcgagcga gcgcgccagc      2820
gattctcttg tttgctccag actctcaggc aatgacctga tagcctttgt agagacctct      2880 caaaatagc taccctctcc ggcatgaatt tatcagctag aacggttgaa tatcatattg       2940
atggtgattt gactgtctcc ggcctttctc acccgtttga atctttacct acacattact      3000
caggcattgc atttaaaata tatgagggtt ctaaaaattt ttatccttgc gttgaaataa      3060
aggcttctcc cgcaaaagta ttacagggtc ataatgtttt tggtacaacc gatttagctt      3120
tatgctctga ggctttattg cttaattttg ctaattcttt gccttgcctg tatgatttat      3180
tggatgttgg aattcctgat gcggtatttt ctccttacgc atctgtgcgg tatttcacac      3240
cgcatatggt gcactctcag tacaatctgc tctgatgccg catagttaag ccagccccga      3300
cacccgccaa cacccgctga cgcgccctga cgggcttgtc tgctcccggc atccgcttac      3360
agacaagctg tgaccgtctc cgggagctgc atgtgtcaga ggttttcacc gtcatcaccg      3420
aaacgcgcga cgaaaggg cctcgtgata cgcctatttt tataggttaa tgtcatgata       3480
ataatggttt cttagacgtc aggtggcact tttcggggaa atgtgcgcgg aacccctatt      3540
tgtttatttt tctaaataca ttcaaatatg tatccgctca tgagacaata accctgataa      3600
atgcttcaat aatattgaaa aaggaagagt atgagtattc aacatttccg tgtcgccctt      3660
attccctttt ttgcggcatt ttgccttcct gttttgctc acccagaaac gctggtgaaa       3720
gtaaaagatg ctgaagatca gttgggtgca cgagtgggtt acatcgaact ggatctcaac      3780
agcggtaaga tccttgagag ttttcgcccc gaagaacgtt ttccaatgat gagcactttt      3840
aaagttctgc tatgtggcgc ggtattatcc cgtattgacg ccgggcaaga gcaactcggt      3900
cgccgcatac actattctca gaatgacttg gttgagtact caccagtcac agaaaagcat      3960
cttacggatg gcatgacagt aagagaatta tgcagtgctg ccataaccat gagtgataac      4020
actgcggcca acttacttct gacaacgatc ggaggaccga aggagctaac cgcttttttg      4080
cacaacatgg gggatcatgt aactcgcctt gatcgttggg aaccggagct gaatgaagcc      4140
ataccaaacg acgagcgtga caccacgatg cctgtagcaa tggcaacaac gttgcgcaaa      4200
ctattaactg gcgaactact tactctagct tcccggcaac aattaataga ctggatggag      4260
gcggataaag ttgcaggacc acttctgcgc tcggcccttc cggctggctg gtttattgct      4320
gataaatctg gagccggtga gcgtgggtct cgcggtatca ttgcagcact ggggccagat      4380
ggtaagccct cccgtatcgt agttatctac acgacgggga gtcaggcaac tatggatgaa      4440
cgaaatagac agatcgctga gataggtgcc tcactgatta agcattggta actgtcagac      4500
caagtttact catatatact ttagattgat ttaaaacttc attttttaatt taaaaggatc      4560 taggtgaaga tcctttttga taatctcatg accaaaatcc cttaacgtga gttttcgttc      4620
cactgagcgt cagaccccgt agaaaagatc aaaggatctt cttgagatcc ttttttctg       4680 cgcgtaatct gctgcttgca aacaaaaaaa ccaccgctac cagcggtggt ttgtttgccg      4740
```

-continued

```
gatcaagagc taccaactct tttttccgaag gtaactggct tcagcagagc gcagatacca    4800
aatactgtcc ttctagtgta gccgtagtta ggccaccact tcaagaactc tgtagcaccg    4860
cctacatacc tcgctctgct aatcctgtta ccagtggctg ctgccagtgg cgataagtcg    4920
tgtcttaccg ggttggactc aagacgatag ttaccggata aggcgcagcg gtcgggctga    4980
acgggggtt cgtgcacaca gcccagcttg gagcgaacga cctacaccga actgagatac     5040
ctacagcgtg agctatgaga aagcgccacg cttcccgaag ggagaaaggc ggacaggtat    5100
ccggtaagcg gcagggtcgg aacaggagag cgcacgaggg agcttccagg gggaaacgcc    5160
tggtatcttt atagtcctgt cgggtttcgc cacctctgac ttgagcgtcg attttttgtga   5220
tgctcgtcag gggggcggag cctatggaaa acgccagca acgcggcctt tttacggttc     5280
ctggcctttt gctggccttt tgctcacatg ttctttcctg cgttatcccc tgattctgtg    5340
gataaccgta ttaccgcctt tgagtgagct gataccgctc gccgcagccg aacgaccgag    5400
cgcagcgagt cagtgagcga ggaagcggaa gagcgcccaa tacgcaaacc gcctctcccc    5460
gcgcgttggc cgattcatta atgcagctgg cgcgctcgct cgctcactga ggccgcccgg    5520
gcaaagcccg ggcgtcgggc gacctttggt cgcccggcct cagtgagcga gcgagcgcgc    5580
agagagggag tggccaactc catcactgat                                     5610
```

<210> SEQ ID NO 3  
<211> LENGTH: 7096  
<212> TYPE: DNA  
<213> ORGANISM: Homo sapien

<400> SEQUENCE: 3

```
aaaacttgcg gccgcggaat tcgactcta ggccattgca tacgttgtat ctatatcata     60
atatgtacat ttatattggc tcatgtccaa tatgaccgcc atgttgacat tgattattga    120
ctagttatta atagtaatca attacggggt cattagttca tagcccatat atggagttcc    180
gcgttacata acttacggta aatggcccgc ctggctgacc gcccaacgac ccccgcccat    240
tgacgtcaat aatgacgtat gttcccatag taacgccaat agggactttc cattgacgtc    300
aatgggtgga gtatttacgg taaactgccc acttggcagt acatcaagtg tatcatatgc    360
caagtccgcc ccctattgac gtcaatgacg gtaaatggcc cgcctggcat tatgcccagt    420
acatgacctt acgggacttt cctacttggc agtacatcta cgtattagtc atcgctatta    480
ccatggtgat gcggttttgg cagtacacca atgggcgtgg atagcggttt gactcacggg    540
gatttccaag tctccacccc attgacgtca atgggagttt gttttggcac caaaatcaac    600
gggactttcc aaaatgtcgt aataaccccg ccccgttgac gcaaatgggc ggtaggcgtg    660
tacggtggga ggtctatata agcagagctc gtttagtgaa ccgtcagatc gcctggagac    720
gccatccacg ctgttttgac ctccatagaa gacaccggga ccgatccagc ctccgcggcc    780
gggaacggtg cattggaacg cggattcccc gtgccaagag tgacgtaagt accgcctata    840
gactctatag gcacaccct ttggctctta tgcatgctat actgttttg gcttggggcc      900
tatacacccc cgctccttat gctataggtg atggtatagc ttagcctata ggtgtgggtt    960
attgaccatt attgaccact cccctattgg tgacgtact ttccattact aatccataac    1020
atggctcttt gccacaacta tctctattgg ctatatgcca atactctgtc cttcagagac    1080
tgacacggac tctgtatttt tacaggatgg ggtccattta ttatttacaa attcacatat    1140
acaacaacgc cgtcccccgt gcccgcagtt tttattaaac atagcgtggg atctccgaca    1200
```

```
tctcgggtac gtgttccgga catgggctct tctccggtag cggcggagct tccacatccg    1260
agccctggtc ccatccgtcc agcggctcat ggtcgctcgg cagctccttg ctcctaacag    1320
tggaggccag acttaggcac agcacaatgc ccaccaccac cagtgtgccg cacaaggccg    1380
tggcggtagg gtatgtgtct gaaaatgagc tcggagattg ggctcgcacc tggacgcaga    1440
tggaagactt aaggcagcgg cagaagaaga tgcaggcagc tgagttgttg tattctgata    1500
agagtcagag gtaactcccg ttgcggtgct gttaacggtg gagggcagtg tagtctgagc    1560
agtactcgtt gctgccgcgc gcgccaccag acataatagc tgacagacta acagactgtt    1620
cctttccatg ggtcttttct gcagtcaccg tcgtcgacct aagaattcgc cctttcacca    1680
tggtcagcta ctgggacacc ggggtcctgc tgtgcgcgct gctcagctgt ctgcttctca    1740
caggatctag ttcaggttca aaattaaaag atcctgaact gagtttaaaa ggcacccagc    1800
acatcatgca agcaggccag acactgcatc tccaatgcag ggggaagca gcccataaat    1860 ggtctttgcc tgaaatggtg agtaaggaaa gcgaaaggct gagcataact aaatctgcct    1920
gtggaagaaa tggcaaacaa ttctgcagta ctttaacctt gaacacagct caagcaaacc    1980
acactggctt ctacagctgc aaatatctag ctgtacctac ttcaaagaag aaggaaacag    2040
aatctgcaat ctatatattt attagtgata caggtagacc tttcgtagag atgtacagtg    2100
aaatccccga aattatacac atgactgaag gaagggagtc cgtcattccc tgccggggtta    2160 cgtcacctaa catcactgtt actttaaaaa gtttccact tgacactttg atccctgatg    2220
gaaaacgcat aatctgggac agtagaaagg gcttcatcat atcaaatgca acgtacaaag    2280
aaatagggct tctgacctgt gaagcaacag tcaatgggca tttgtataag acaaactatc    2340
tcacacatcg acaaaccaat acaatcatag atgtccaaat aagcacacca cgcccagtca    2400
aattacttag aggccatact cttgtcctca attgtactgc taccactccc ttgaacacga    2460
gagttcaaat gacctggagt taccctgatg aaaaaaataa gagagcttcc gtaaggcgac    2520
gaattgacca aagcaattcc catgccaaca tattctacag tgttcttact attgacaaaa    2580
tgcagaacaa agacaaagga ctttatactt gtcgtgtaag gagtggacca tcattcaaat    2640
ctgttaacac ctcagtgcat atatatgata aagcattcat cactgtgaaa catcgaaaac    2700
agcaggtgct tgaaaccgta gctggcaagc ggtcttaccg gctctctatg aaagtgaagg    2760 catttcccc gccggaagtt gtatggttaa agatgggtt acctgcgact gagaaatctg    2820
ctcgctattt gactcgtggc tactcgttaa ttatcaagga cgtaactgaa gaggatgcag    2880
ggaattatac aatcttgctg agcataaaac agtcaaatgt gtttaaaaac ctcactgcca    2940
ctctaattgt caatgtgaaa ccccagattt acgaaaaggc cgtgtcatcg tttccagacc    3000
cggctctcta cccactgggc agcagacaaa tcctgacttg taccgcatat ggtatccctc    3060
aacctacaat caagtggttc tggcaccccc gtaaccataa tcattccgaa gcaaggtgtg    3120
acttttgttc caataatgaa gagtccttta tcctggatgc tgacagcaac atgggaaaca    3180
gaattgagag catcactcag cgcatggcaa taatagaagg aaagaataag atggctagca    3240
ccttggttgt ggctgactct agaatttctg gaatctacat ttgcatagct tccaataaag    3300
ttgggactgt gggaagaaac ataagctttt atatcacaga tgtgccaaat gggtttcatg    3360
ttaacttgga aaaaatgccg acggaaggag aggacctgaa actgtcttgc acagttaaca    3420
agttcttata cagagacgtt acttggattt tactgcggac agttaataac agaacaatgc    3480
actacagtat tagcaagcaa aaaatggcca tcactaagga gcactccatc actcttaatc    3540
ttaccatcat gaatgtttcc ctgcaagatt caggcaccta tgcctgcaga gccaggaatg    3600
```

-continued

```
tatacacagg ggaagaaatc ctccagaaga aagaaattac aatcagaggt gagcactgca      3660
acaaaaaggc tgttttctct cggatctcca aatttaaaag cacaaggaat gattgtacca      3720
cacaaagtaa tgtaaaacat taaaggactc attaaaaagt aacagttgtc tcatatcatc      3780
ttgatttatt gtcactgttg ctaactttca ggctcaaggg cgaattcagg cctaagcttc      3840
ctaggtatcg atctcgagca agtctagaaa gccatggata tcggatccac tacgcgttag      3900
agctcgctga tcagcctcga ctgtgccttc tagttgccag ccatctgttg tttgcccctc      3960
ccccgtgcct tccttgaccc tggaaggtgc cactcccact gtcctttcct aataaaatga      4020
ggaaattgca tcgcattgtc tgagtaggtg tcattctatt ctggggggtg gggtggggca      4080
ggacagcaag ggggaggatt gggaagacaa tagcaggggg gtgggcgaag aactccagca      4140
tgagatcccc gcgctggagg atcatccagc tagcaagtcc catcagtgat ggagttggcc      4200
actccctctc tgcgcgctcg ctcgctcact gaggccgggc gaccaaaggt cgcccgacgc      4260
ccgggctttg cccgggcggc ctcagtgagc gagcgagcgc gccagcgatt ctcttgtttg      4320
ctccagactc tcaggcaatg acctgatagc ctttgtagag acctctcaaa aatagctacc      4380
ctctccggca tgaatttatc agctagaacg gttgaatatc atattgatgg tgatttgact      4440
gtctccggcc tttctcaccc gtttgaatct ttacctacac attactcagg cattgcattt      4500
aaaatatatg agggttctaa aaattttat ccttgcgttg aaataaaggc ttctcccgca      4560
aaagtattac agggtcataa tgttttggt acaaccgatt tagctttatg ctctgaggct      4620
ttattgctta attttgctaa ttctttgcct tgcctgtatg atttattgga tgttggaatt      4680
cctgatgcgg tattttctcc ttacgcatct gtgcggtatt tcacaccgca tatggtgcac      4740
tctcagtaca atctgctctg atgccgcata gttaagccag ccccgacacc cgccaacacc      4800
cgctgacgcg ccctgacggg cttgtctgct cccggcatcc gcttacagac aagctgtgac      4860
cgtctccggg agctgcatgt gtcagaggtt ttcaccgtca tcaccgaaac gcgcgagacg      4920
aaagggcctc gtgatacgcc tatttttata ggttaatgtc atgataataa tggtttctta      4980
gacgtcaggt ggcactttc ggggaaatgt gcgcggaacc cctatttgtt tatttttcta      5040
aatacattca aatatgtatc cgctcatgag acaataaccc tgataaatgc ttcaataata      5100
ttgaaaaagg aagagtatga gtattcaaca tttccgtgtc gcccttattc ccttttttgc      5160
ggcattttgc cttcctgttt ttgctcaccc agaaacgctg gtgaaagtaa aagatgctga      5220
agatcagttg ggtgcacgag tgggttacat cgaactggat ctcaacagcg gtaagatcct      5280
tgagagtttt cgccccgaag aacgttttcc aatgatgagc acttttaaag ttctgctatg      5340
tggcgcggta ttatcccgta ttgacgccgg gcaagagcaa ctcggtcgcc gcatacacta      5400
ttctcagaat gacttggttg agtactcacc agtcacagaa aagcatctta cggatggcat      5460
gacagtaaga gaattatgca gtgctgccat aaccatgagt gataacactg cggccaactt      5520
acttctgaca acgatcggag gaccgaagga gctaaccgct tttttgcaca acatggggga      5580
tcatgtaact cgccttgatc gttgggaacc ggagctgaat gaagccatac caaacgacga      5640
gcgtgacacc acgatgcctg tagcaatggc aacaacgttg cgcaaactat taactggcga      5700
actacttact ctagcttccc ggcaacaatt aatagactgg atggaggcgg ataaagttgc      5760
aggaccactt ctgcgctcgg cccttccggc tggctggttt attgctgata aatctggagc      5820
cggtgagcgt gggtctcgcg gtatcattgc agcactgggg ccagatggta agccctcccg      5880
tatcgtagtt atctacacga cggggagtca ggcaactatg gatgaacgaa atagacagat      5940
```

-continued

```
cgctgagata ggtgcctcac tgattaagca ttggtaactg tcagaccaag tttactcata      6000
tatactttag attgatttaa aacttcattt ttaatttaaa aggatctagg tgaagatcct      6060
ttttgataat ctcatgacca aaatcccctta acgtgagttt tcgttccact gagcgtcaga     6120
ccccgtagaa aagatcaaag gatcttcttg agatcctttt tttctgcgcg taatctgctg     6180
cttgcaaaca aaaaaaccac cgctaccagc ggtggtttgt ttgccggatc aagagctacc     6240 aactctttt ccgaaggtaa ctggcttcag cagagcgcag ataccaaata ctgtccttct     6300
agtgtagccg tagttaggcc accacttcaa gaactctgta gcaccgccta catacctcgc     6360
tctgctaatc ctgttaccag tggctgctgc cagtggcgat aagtcgtgtc ttaccgggtt     6420
ggactcaaga cgatagttac cggataaggc gcagcggtcg ggctgaacgg ggggttcgtg     6480
cacacagccc agcttggagc gaacgaccta caccgaactg agatacctac agcgtgagct     6540
atgagaaagc gccacgcttc ccgaagggag aaaggcggac aggtatccgg taagcggcag     6600
ggtcggaaca ggagagcgca cgagggagct tccaggggga aacgcctggt atctttatag     6660
tcctgtcggg tttcgccacc tctgacttga gcgtcgattt tgtgatgct cgtcaggggg     6720 gcggagccta tggaaaaacg ccagcaacgc ggcctttta cggttcctgg ccttttgctg      6780
gccttttgct cacatgttct ttcctgcgtt atcccctgat tctgtggata accgtattac     6840
cgcctttgag tgagctgata ccgctcgccg cagccgaacg accgagcgca gcgagtcagt     6900
gagcgaggaa gcggaagagc gcccaatacg caaaccgcct ctccccgcgc gttggccgat     6960
tcattaatgc agctggcgcg ctcgctcgct cactgaggcc gcccgggcaa agcccgggcg     7020
tcgggcgacc tttggtcgcc cggcctcagt gagcgagcga gcgcgcagag agggagtggc     7080
caactccatc actgat                                                     7096
```

<210> SEQ ID NO 4
<211> LENGTH: 636
<212> TYPE: DNA
<213> ORGANISM: Homo sapien

<400> SEQUENCE: 4

```
atggctccct tagccgaagt cgggggcttt ctgggcggcc tggagggctt gggccagcag      60
gtgggttcgc atttcctgtt gcctcctgcc ggggagcggc cgccgctgct ggcgagcgc     120 aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg cacccggcag gaccacagcc tcttcggtat cttggaattc     300
atcagtgtgg cagtgggact ggtcagtatt agaggtgtgg acagtggtct ctatcttgga     360
atgaatgaca aggagaact ctatggatca gagaaactta cttccgaatg catctttagg     420
gagcagtttg aagagaactg gtataacacc tattcatcta acatatataa acatggagac     480 actgccgca ggtattttgt ggcacttaac aaagacggaa ctccaagaga tggcgccagg     540
tccaagaggc atcagaaatt tacacatttc ttacctagac cagtggatcc agaaagagtt     600
ccagaattgt acaaggacct actgatgtac acttga                              636
```

<210> SEQ ID NO 5
<211> LENGTH: 211
<212> TYPE: PRT
<213> ORGANISM: Homo sapien

<400> SEQUENCE: 5

Met Ala Pro Leu Ala Glu Val Gly Gly Phe Leu Gly Gly Leu Glu Gly

```
                1               5                      10                      15
Leu Gly Gln Gln Val Gly Ser His Phe Leu Pro Pro Ala Gly Glu
                20                      25                      30

Arg Pro Pro Leu Leu Gly Glu Arg Ser Ala Ala Glu Arg Ser Ala
                35                      40                      45

Arg Gly Gly Pro Gly Ala Ala Gln Leu Ala His Leu His Gly Ile Leu
        50                      55                      60

Arg Arg Arg Gln Leu Tyr Cys Arg Thr Gly Phe His Leu Gln Ile Leu
65                      70                      75                      80

Pro Asp Gly Ser Val Gln Gly Thr Arg Gln Asp His Ser Leu Phe Gly
                        85                      90                      95

Ile Leu Glu Phe Ile Ser Val Ala Val Gly Leu Val Ser Ile Arg Gly
                100                     105                     110

Val Asp Ser Gly Leu Tyr Leu Gly Met Asn Asp Lys Gly Glu Leu Tyr
                115                     120                     125

Gly Ser Glu Lys Leu Thr Ser Glu Cys Ile Phe Arg Glu Gln Phe Glu
130                     135                     140

Glu Asn Trp Tyr Asn Thr Tyr Ser Ser Asn Ile Tyr Lys His Gly Asp
145                     150                     155                     160

Thr Gly Arg Arg Tyr Phe Val Ala Leu Asn Lys Asp Gly Thr Pro Arg
                        165                     170                     175

Asp Gly Ala Arg Ser Lys Arg His Gln Lys Phe Thr His Phe Leu Pro
                180                     185                     190

Arg Pro Val Asp Pro Glu Arg Val Pro Glu Leu Tyr Lys Asp Leu Leu
                195                     200                     205

Met Tyr Thr
        210

<210> SEQ ID NO 6
<211> LENGTH: 659
<212> TYPE: DNA
<213> ORGANISM: Homo sapien

<400> SEQUENCE: 6
gagcgcagcc ctgatggaat ggatgagatc tagagttggg accctgggac tgtgggtccg      60
actgctgctg gctgtcttcc tgctgggggt ctaccaagca tacccatcc ctgactccag      120 ccccctcctc cagtttgggg gtcaagtccg gcagaggtac ctctacacag atgacgacca    180
agacactgaa gcccacctgg agatcaggga ggatggaaca gtggtaggcg cagcacaccg    240
cagtccagaa agtctcctgg agctcaaagc cttgaagcca ggggtcattc aaatcctggg    300
tgtcaaagcc tctaggtttc tttgccaaca gccagatgga gctctctatg gatcgcctca    360
ctttgatcct gaggcctgca gcttcagaga actgctgctg gaggacggtt acaatgtgta    420
ccagtctgaa gcccatggcc tgcccctgcg tctgcctcag aaggactccc aaaccagga    480 tgcaacatcc tggggacctg tgcgcttcct gcccatgcca ggcctgctcc acgagcccca    540
agaccaagca ggattcctgc ccccagagcc cccagatgtg ggctcctctg accccctgag    600
catggtagag cctttacagg gccgaagccc cagctatgcg tcctgactct tcctgaatc     659

<210> SEQ ID NO 7
<211> LENGTH: 210
<212> TYPE: PRT
<213> ORGANISM: Homo sapien

<400> SEQUENCE: 7
```

-continued

```
Met Glu Trp Met Arg Ser Arg Val Gly Thr Leu Gly Leu Trp Val Arg
 1               5                  10                  15

Leu Leu Leu Ala Val Phe Leu Leu Gly Val Tyr Gln Ala Tyr Pro Ile
             20                  25                  30

Pro Asp Ser Ser Pro Leu Leu Gln Phe Gly Gly Gln Val Arg Gln Arg
         35                  40                  45

Tyr Leu Tyr Thr Asp Asp Gln Asp Thr Glu Ala His Leu Glu Ile
 50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                 85                  90                  95

Val Lys Ala Ser Arg Phe Leu Cys Gln Gln Pro Asp Gly Ala Leu Tyr
             100                 105                 110

Gly Ser Pro His Phe Asp Pro Glu Ala Cys Ser Phe Arg Glu Leu Leu
             115                 120                 125

Leu Glu Asp Gly Tyr Asn Val Tyr Gln Ser Glu Ala His Gly Leu Pro
             130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                 165                 170                 175

Asp Gln Ala Gly Phe Leu Pro Glu Pro Pro Asp Val Gly Ser Ser
             180                 185                 190

Asp Pro Leu Ser Met Val Glu Pro Leu Gln Gly Arg Ser Pro Ser Tyr
             195                 200                 205

Ala Ser
    210

<210> SEQ ID NO 8
<211> LENGTH: 5974
<212> TYPE: DNA
<213> ORGANISM: Homo sapien

<400> SEQUENCE: 8
aaaacttgcg gccgcggaat tcgactcta ggccattgca tacgttgtat ctatatcata      60
atatgtacat ttatattggc tcatgtccaa tatgaccgcc atgttgacat tgattattga    120
ctagttatta atagtaatca attacggggt cattagttca tagcccatat atggagttcc    180
gcgttacata acttacggta atggcccgc ctggctgacc gcccaacgac ccccgcccat    240
tgacgtcaat aatgacgtat gttcccatag taacgccaat agggactttc cattgacgtc    300
aatgggtgga gtatttacgg taaactgccc acttggcagt acatcaagtg tatcatatgc    360
caagtccgcc ccctattgac gtcaatgacg gtaaatggcc cgcctggcat tatgcccagt    420
acatgacctt acgggacttt cctacttggc agtacatcta cgtattagtc atcgctatta    480
ccatggtgat gcggttttgg cagtacacca tgggcgtgg atagcggttt gactcacggg    540
gatttccaag tctccacccc attgacgtca atgggagttt gttttggcac caaaatcaac    600
gggactttcc aaaatgtcgt aataaccccg cccgttgac gcaaatgggc ggtaggcgtg    660
tacggtggga ggtctatata agcagagctc gtttagtgaa ccgtcagatc gcctggagac    720
gccatccacg ctgttttgac ctccatagaa gacaccggga ccgatccagc ctccgcggcc    780
gggaacggtg cattggaacg cggattcccc gtgccaagag tgacgtaagt accgcctata    840
gactctatag gcacaccct ttggctctta tgcatgctat actgtttttg gcttggggcc    900
```

-continued

```
tatacacccc cgctccttat gctataggtg atggtatagc ttagcctata ggtgtgggtt      960
attgaccatt attgaccact cccctattgg tgacgatact ttccattact aatccataac     1020
atggctcttt gccacaacta tctctattgg ctatatgcca atactctgtc cttcagagac     1080
tgacacggac tctgtatttt tacaggatgg ggtccattta ttatttacaa attcacatat     1140
acaacaacgc cgtcccccgt gcccgcagtt tttattaaac atagcgtggg atctccgaca     1200
tctcgggtac gtgttccgga catgggctct tctccggtag cggcggagct tccacatccg     1260
agccctggtc ccatccgtcc agcggctcat ggtcgctcgg cagctccttg ctcctaacag     1320
tggaggccag acttaggcac agcacaatgc ccaccaccac cagtgtgccg cacaaggccg     1380
tggcggtagg gtatgtgtct gaaaatgagc tcggagattg ggctcgcacc tggacgcaga     1440
tggaagactt aaggcagcgg cagaagaaga tgcaggcagc tgagttgttg tattctgata     1500
agagtcagag gtaactcccg ttgcggtgct gttaacggtg gagggcagtg tagtctgagc     1560
agtactcgtt gctgccgcgc gcgccaccag acataatagc tgacagacta acagactgtt     1620
cctttccatg ggtcttttct gcagtcaccg tcgtcgacct aagaattcag gtatggctgc     1680
tggttctatc actaccctgc cagctctgcc agaagacggt ggttctggtg ccttcccacc     1740
aggtcacttc aaagacccaa aacgtctgta ctgcaaaaac ggtggtttct tcctgcgcat     1800 ccacccccgac ggccgagtgg acgggtccg cgagaagagc gacccacaca tcaaactaca     1860
acttcaagca aagagagag gggttgtgtc tatcaaagga gtgtgtgcaa accgttacct     1920
tgctatgaaa aagatggaa gattactagc ttctaaatgt gttacagacg agtgtttctt     1980
ttttgaacga ttggagtcta ataactacaa tacttaccgg tcaaggaaat acaccagttg     2040
gtatgtggca ctgaaacgaa ctgggcagta taaacttgga tccaaaacag gacctgggca     2100
gaaagctata cttttttcttc caatgtctgc taagagctga tcttaatggc agcatctgat     2160
ctcattttac atgaagcttc ctaggtatcg atctcgagca agtctagaaa gccatggata     2220
tcggatccac tacgcgttag agctcgctga tcagcctcga ctgtgccttc tagttgccag     2280
ccatctgttg tttgccccctc ccccgtgcct tccttgaccc tggaaggtgc cactcccact     2340
gtcctttcct aataaaatga ggaaattgca tcgcattgtc tgagtaggtg tcattctatt     2400
ctggggggtg gggtggggca ggacagcaag ggggaggatt gggaagacaa tagcaggggg     2460
gtgggcgaag aactccagca tgagatcccc gcgctggagg atcatccagc tagcaagtcc     2520
catcagtgat ggagttggcc actccctctc tgcgcgctcg ctcgctcact gaggccgggc     2580
gaccaaaggt cgcccgacgc ccgggctttg cccgggcggc ctcagtgagc gagcgagcgc     2640
gccagcgatt ctcttgtttg ctccagactc tcaggcaatg acctgatagc ctttgtagag     2700
acctctcaaa aatagctacc ctctccggca tgaatttatc agctagaacg gttgaatatc     2760
atattgatgg tgatttgact gtctccggcc tttctcaccc gtttgaatct ttacctacac     2820
attactcagg cattgcattt aaaatatatg agggttctaa aaattttat ccttgcgttg     2880 aaataaaggc ttctcccgca aaagtattac agggtcataa tgttttttggt caaccgatt     2940 tagctttatg ctctgaggct ttattgctta atttgctaa ttctttgcct tgcctgtatg     3000
atttattgga tgtggaatt cctgatgcgg tattttctcc ttacgcatct gtgcggtatt     3060
tcacaccgca tatggtgcac tctcagtaca atctgctctg atgccgcata gttaagccag     3120
ccccgacacc cgccaacacc cgctgacgcg ccctgacggg cttgtctgct cccggcatcc     3180
gcttacagac aagctgtgac cgtctccggg agctgcatgt gtcagaggtt ttcaccgtca     3240
```

-continued

```
tcaccgaaac gcgcgagacg aaagggcctc gtgatacgcc tatttttata ggttaatgtc    3300
atgataataa tggtttctta gacgtcaggt ggcacttttc ggggaaatgt gcgcggaacc    3360
cctatttgtt tattttctta aatacattca aatatgtatc cgctcatgag acaataaccc    3420
tgataaatgc ttcaataatg tacccgtcaa gaaggcgata gaaggcgatg cgctgcgaat    3480
cgggagcggc gataccgtaa agcacgagga agcggtcagc ccattcgctt cagcaatatc    3540
acgggtagcc aacgctatgt cctgatagcg gtccgccaca cccagccggc cacagtcgat    3600
gaatccagaa aagcggccat tttccaccat gatattcggc aagcaggcat cgccatgggt    3660
cacgacgaga tcctcgccgt cgggcatgcg cgccttgagc ctggcgaaca gttcggctgg    3720
cgcgagcccc tgatgctctt cgtccagatc atcctgatcg acaagaccgg cttccatccg    3780
agtacgtgct cgctcgatgc gatgtttcgc ttggtggtcg aatgggcagg tagccggatc    3840
aagcgtatgc agccgccgca ttgcatcagc catgatggat actttctcgg caggagcaag    3900
gtgagatgac aggagatcct gccccggcac ttcgcccaat agcagccagt cccttcccgc    3960
ttcagtgaca acgtcgagca cagctgcgca aggaacgccc gtcgtggcca gccacgatag    4020
ccgcgctgcc tcgtcctgca gttcattcag ggcaccggac aggtcggtct tgacaaaaag    4080
aaccgggcgc ccctgcgctg acagccggaa cacggcggca tcagagcagc cgattgtctg    4140
ttgtgcccag tcatagccga atagcctctc cacccaagcg gccggagaac ctgcgtgcaa    4200
tccatcttgt tcaatcatgc gaaacgatcc tcatcctgtc tcttgatcag atcttgatcc    4260
cctgcgccat cagatccttg gcggcaagaa agccatccag tttactttgc agggcttccc    4320
aaccttacca gagggcgccc cagctggcaa ttccggttcg cttgctgtcc ataaaaccgc    4380
ccagtctagc tatcgccatg taagcccact gcaagctacc tgctttctct ttgcgcttgc    4440
gttttccctt gtccagatag cccagtagct gacattcatc cggggtcagc accgtttctg    4500
cggactggct ttctacgtgt tccgcttcct ttagcagccc ttgcgccctg agtgcttgcg    4560
gcagcgtgaa gctgtcaatt ccgcgttaaa tttttgttaa atcagctcat tttttaacca    4620
ataggccgaa atcggcaaaa tcccttataa atcaaaagaa tagcccgaga tagggttgag    4680
tgttgttcca gtttggaaca agagtccact attaaagaac gtggactcca acgtcaaagg    4740
gcgaaaaacc gtctatcagg gcgatggcgg atcagcttat gcggtgtgaa ataccgcaca    4800
gatgcgtaag gagaaaatac cgcatcaggc gctcttccgc ttcctcgctc actgactcgc    4860
tgcgctcggt cgttcggctg cggcgagcgg tatcagctca ctcaaaggcg gtaatacggt    4920
tatccacaga atcaggggat aacgcaggaa agaacatgcg cgcgccaca tgtgagcaaa    4980 aggccagcaa aaggccagga accgtaaaaa ggccgcgttg ctggcgtttt tccataggct    5040
ccgcccccct gacgagcatc acaaaaatcg acgctcaagt cagaggtggc gaaacccgac    5100
aggactataa agataccagg cgtttccccc tggaagctcc ctcgtgcgct ctcctgttcc    5160
gaccctgccg cttaccggat acctgtccgc ctttctccct tcgggaagcg tggcgctttc    5220
tcatagctca cgctgtaggt atctcagttc ggtgtaggtc gttcgctcca agctgggctg    5280
tgtgcacgaa ccccccgttc agcccgaccg ctgcgcctta ccggtaact atcgtcttga    5340 gtccaacccg gtaagacacg acttatcgcc actggcagca gccactggta acaggattag    5400
cagagcgagg tatgtaggcg gtgctacaga gttcttgaag tggtggccta actacggcta    5460
cactagaagg acagtatttg gtatctgcgc tctgctgaag ccagttacct tcggaaaaag    5520
agttggtagc tcttgatccg gcaaacaaac caccgctggt agcggcggtt ttttgtttgc    5580
aagcagcaga ttacgcgcag aaaaaaagga tctcaagaag atcctttgat cttttcttac    5640
```

-continued

| | |
|---|---|
| tgaacggtga tccccaccgg aattgcggcc catgttcttt cctgcgttat cccctgattc | 5700 |
| tgtggataac cgtattaccg cctttgagtg agctgatacc gctcgccgca gccgaacgac | 5760 |
| cgagcgcagc gagtcagtga gcgaggaagc ggaagagcgc ccaatacgca aaccgcctct | 5820 |
| ccccgcgcgt tggccgattc attaatgcag ctggcgcgct cgctcgctca ctgaggccgc | 5880 |
| ccgggcaaag cccgggcgtc gggcgacctt tggtcgcccg gcctcagtga gcgagcgagc | 5940 |
| gcgcagagag ggagtggcca actccatcac tgat | 5974 |

<210> SEQ ID NO 9
<211> LENGTH: 41
<212> TYPE: DNA
<213> ORGANISM: Artificial Sequence
<220> FEATURE:
<223> OTHER INFORMATION: Oligonucleotide used for PCR amplification

<400> SEQUENCE: 9
ggtatttaaa acttgcggcc gcggaatttc gactctaggc c        41

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide used for PCR amplification

<400> SEQUENCE: 10
gctgcccggg acttgctagc tggatgatcc tccagcgcgg ggatctcatg        50

<210> SEQ ID NO 11
<211> LENGTH: 42
<212> TYPE: DNA
<213> ORGANISM: Artificial Sequence
<220> FEATURE:
<223> OTHER INFORMATION: PCR primer

<400> SEQUENCE: 11
agatataagc ttaccatggg tgaaaagcgt ctcgccccca aa        42

<210> SEQ ID NO 12
<211> LENGTH: 42
<212> TYPE: DNA
<213> ORGANISM: Artificial Sequence
<220> FEATURE:
<223> OTHER INFORMATION: PCR primer

<400> SEQUENCE: 12
cgcgcgctcg agaccatgag gaatattatc caaagcgaaa ct        42